(12) United States Patent
Gordon

(10) Patent No.: US 10,813,718 B2
(45) Date of Patent: *Oct. 27, 2020

(54) ERGONOMIC DENTAL TOOLS

(71) Applicant: Manuel Barry Gordon, New York, NY (US)

(72) Inventor: Manuel Barry Gordon, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/927,560

(22) Filed: Jun. 26, 2013

(65) Prior Publication Data

US 2013/0288196 A1 Oct. 31, 2013

Related U.S. Application Data

(63) Continuation-in-part of application No. 13/624,257, filed on Sep. 21, 2012, which is a continuation of application No. 12/405,751, filed on Mar. 17, 2009, now Pat. No. 8,297,972.

(51) Int. Cl.

| A61C 1/12 | (2006.01) |
|---|---|
| A61C 17/06 | (2006.01) |
| A61C 17/08 | (2006.01) |
| A61B 13/00 | (2006.01) |
| A61C 3/00 | (2006.01) |

(52) U.S. Cl.
CPC ............... *A61C 1/12* (2013.01); *A61B 13/00* (2013.01); *A61C 3/00* (2013.01); *A61C 17/04* (2013.01); *A61C 17/08* (2019.05)

(58) Field of Classification Search
CPC ......... A61B 13/00; A61B 1/24; A61B 17/224; A46B 15/0081; A61C 1/12; A61C 3/00; A61C 17/04; A61C 17/043

USPC ......... 433/140–141, 143–144; 600/239–243; D24/136

See application file for complete search history.

(56) References Cited

U.S. PATENT DOCUMENTS

| 637,970 A | 11/1899 | Nyman | |
|---|---|---|---|
| 1,009,551 A * | 11/1911 | Nations | 600/242 |
| 1,497,749 A | 5/1922 | Diack | |
| 1,465,259 A * | 8/1923 | Friedman | 600/227 |

(Continued)

FOREIGN PATENT DOCUMENTS

| CN | 201091589 | 7/2008 |
|---|---|---|
| CN | 201091589 Y | 7/2008 |

OTHER PUBLICATIONS

International Search Report and Written Opinion of the International Searching Authority for PCT/US2014/37077 dated Sep. 26, 2014.

(Continued)

*Primary Examiner* — Edward Moran
(74) *Attorney, Agent, or Firm* — Bressler, Amery & Ross PC; Pierre R. Yanney

(57) ABSTRACT

A dental tool is disclosed that includes an operational unit, a neck region and a handle region, in which the neck region is S-shaped. The operational unit can further include a tongue retractor, a flap retractor or a combination thereof. A suction mechanism may be added for eliminating fluids. The neck region may further contain a lateral bend, a rotation of the working end or both. The proximal end of the handle region, opposite the operational unit, may further include any useful apparatus, such as a periosteal elevator or periosteal retractor.

23 Claims, 57 Drawing Sheets

(56) References Cited

U.S. PATENT DOCUMENTS

| | | | |
|---|---|---|---|
| 1,605,321 A * | 11/1926 | Bates | A61C 3/00 433/143 |
| 2,436,040 A | 2/1948 | Friedman | |
| 2,603,870 A | 7/1952 | Harald | |
| 2,723,661 A | 5/1954 | Hull | |
| 2,831,480 A * | 4/1958 | Milano | 600/242 |
| 3,090,122 A | 5/1963 | Erickson | |
| 3,863,627 A | 2/1975 | Bouffard | |
| D235,549 S | 6/1975 | Funderburk | |
| 4,270,902 A * | 6/1981 | Wiland | A61C 3/10 433/143 |
| 4,356,585 A * | 11/1982 | Protell | A46B 9/04 15/111 |
| 4,463,470 A * | 8/1984 | Willis | A46B 9/04 132/325 |
| 4,586,900 A | 5/1986 | Hymanson et al. | |
| D291,001 S | 7/1987 | Gaskins | |
| 4,883,426 A | 11/1989 | Ferrer | |
| 5,078,602 A | 1/1992 | Honoshofsky | |
| 5,282,814 A * | 2/1994 | Srivastava | A61B 17/244 606/161 |
| D359,122 S * | 6/1995 | Kountis | D24/152 |
| 5,463,792 A | 11/1995 | Hogan et al. | |
| 5,676,544 A * | 10/1997 | Urban | A61C 3/00 433/147 |
| D391,370 S | 2/1998 | Cho | |
| 5,730,597 A | 3/1998 | Luttrell et al. | |
| 5,816,806 A * | 10/1998 | Herbst | A61C 3/00 433/141 |
| 5,846,192 A | 12/1998 | Teixido | |
| 6,045,499 A | 4/2000 | Pitesky | |
| 6,102,701 A * | 8/2000 | Engeron | A61C 5/90 433/140 |
| 6,174,162 B1 | 1/2001 | Pozzi | |
| 6,219,874 B1 * | 4/2001 | van Gelder | A46B 5/0025 15/167.1 |
| 6,241,658 B1 | 6/2001 | Goodrich | |
| 6,299,617 B1 * | 10/2001 | Stamler | A61B 17/0231 600/236 |
| 6,575,749 B1 | 6/2003 | Greenwald | |
| 6,901,928 B2 * | 6/2005 | Loubser | A61B 1/00103 128/200.26 |
| D509,590 S | 9/2005 | Cho | |
| 7,238,023 B1 | 7/2007 | Enos | |
| 8,784,101 B1 * | 7/2014 | Engeron | A61C 5/90 433/140 |
| 2001/0034474 A1 | 10/2001 | Ryan | |
| 2002/0128673 A1 | 9/2002 | Ripich et al. | |
| 2004/0086828 A1 | 5/2004 | Torres | |
| 2005/0197665 A1 * | 9/2005 | Teed | A61B 17/244 606/161 |
| 2005/0228233 A1 | 10/2005 | Ritland | |
| 2010/0021863 A1 | 1/2010 | Braman | |
| 2010/0240005 A1 | 9/2010 | Gordon et al. | |
| 2012/0157787 A1 | 6/2012 | Weinstein et al. | |

OTHER PUBLICATIONS

Instruments—Retractors, Misch Spoon and Minesota Retractor, Salvin Dental Supply Catalog, 2011, p. 114.
Instruments—Miscellaneous, Knives/Spatulas/Retractors, Sullivan-Schein Dental Supply Catalog, 2007, p. 584.
Extended European Search Report dated Nov. 24, 2016 in European Patent Application No. 14816780.2.

* cited by examiner

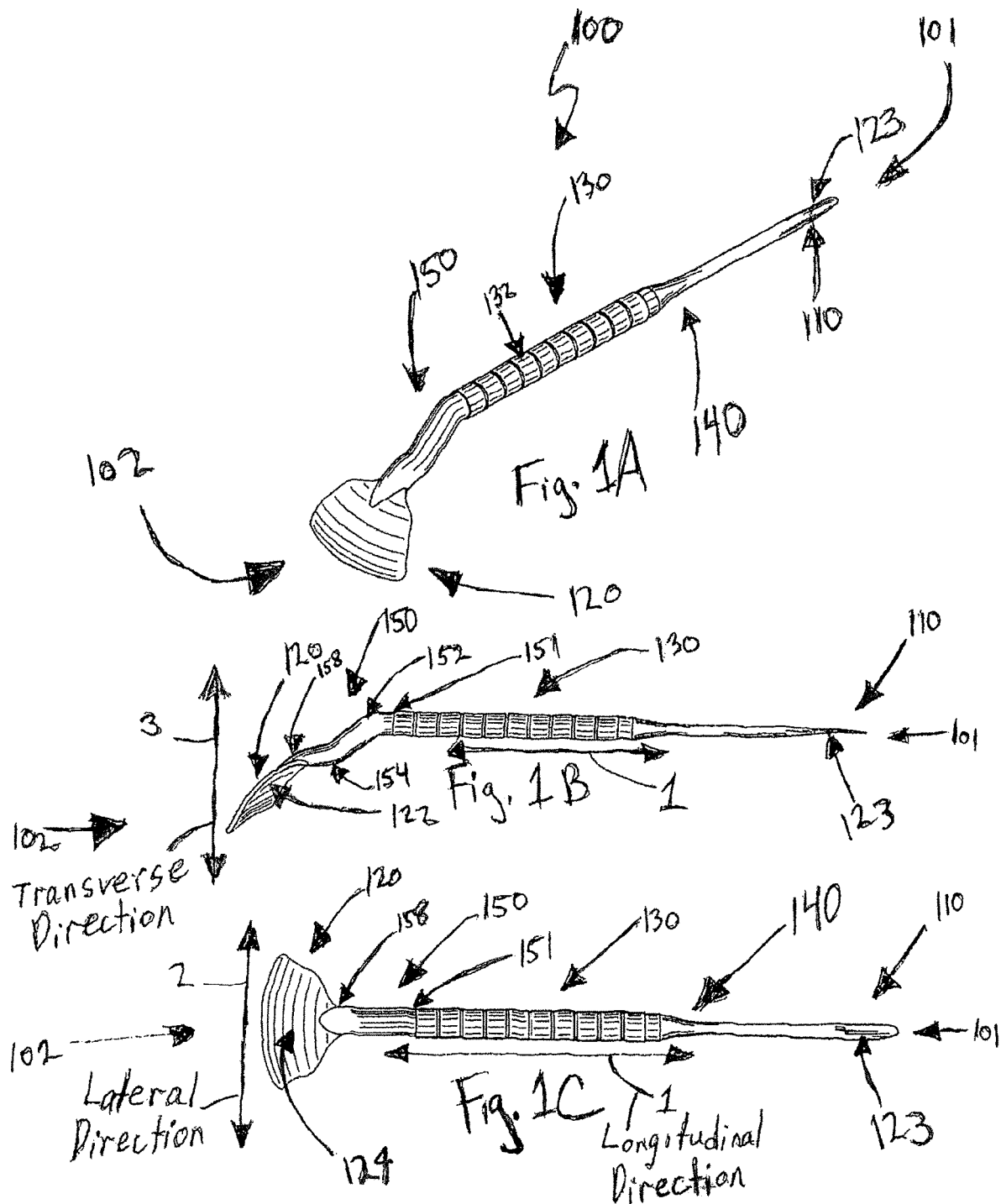

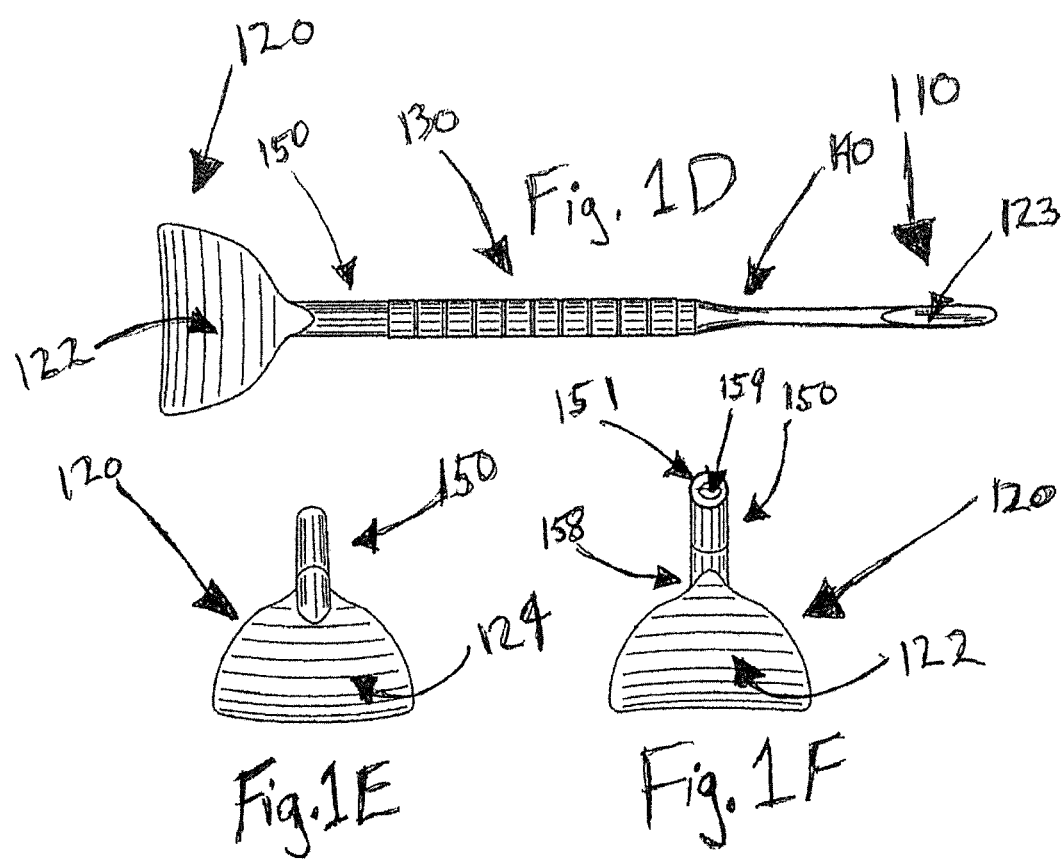

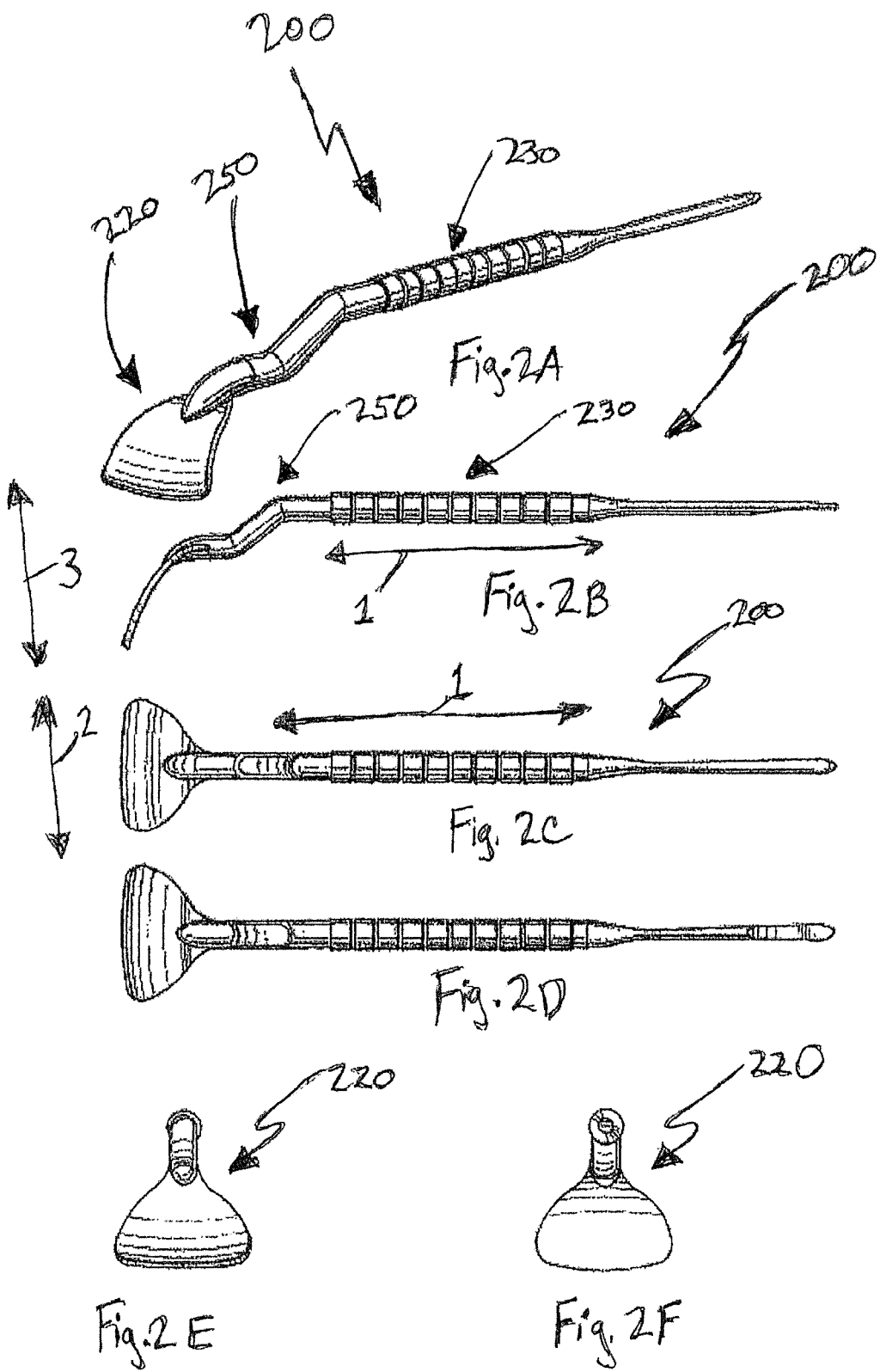

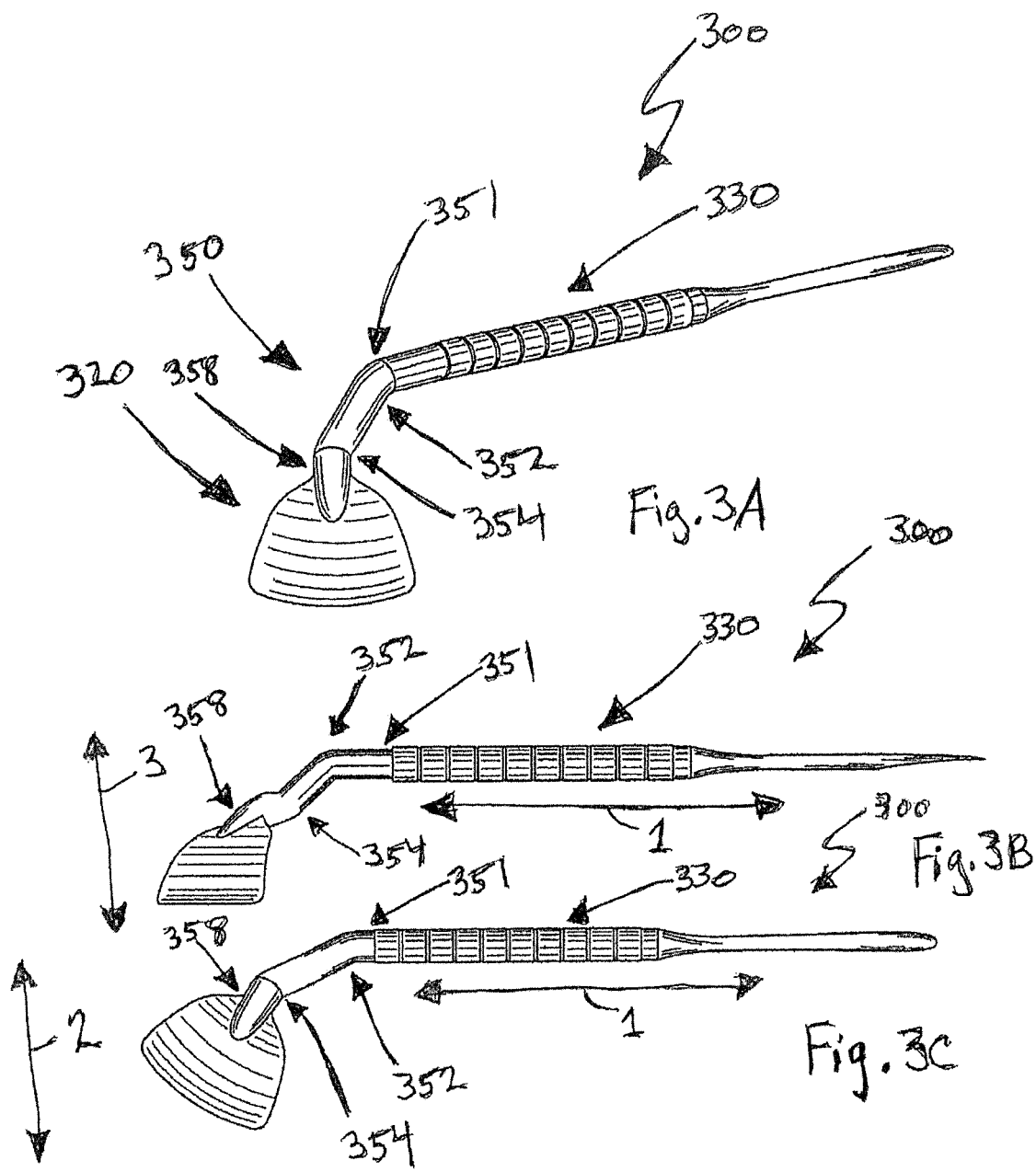

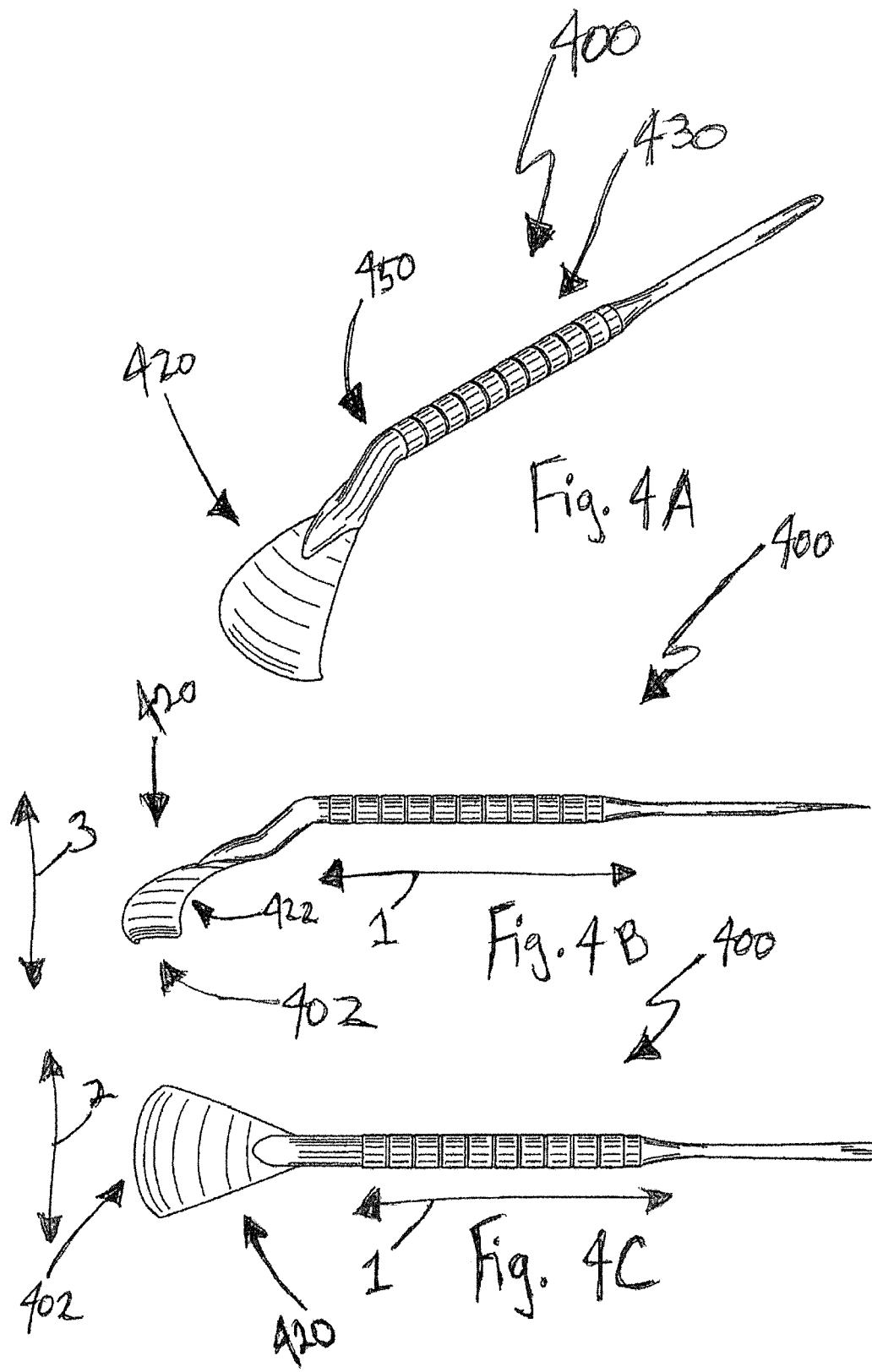

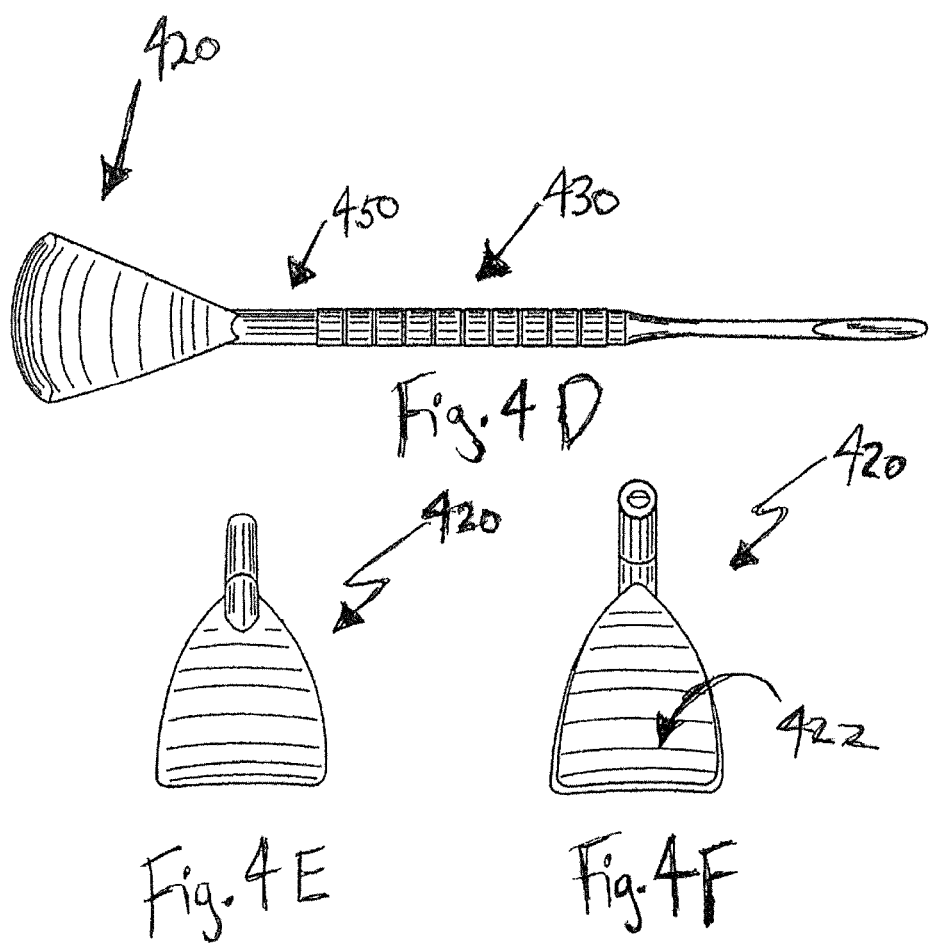

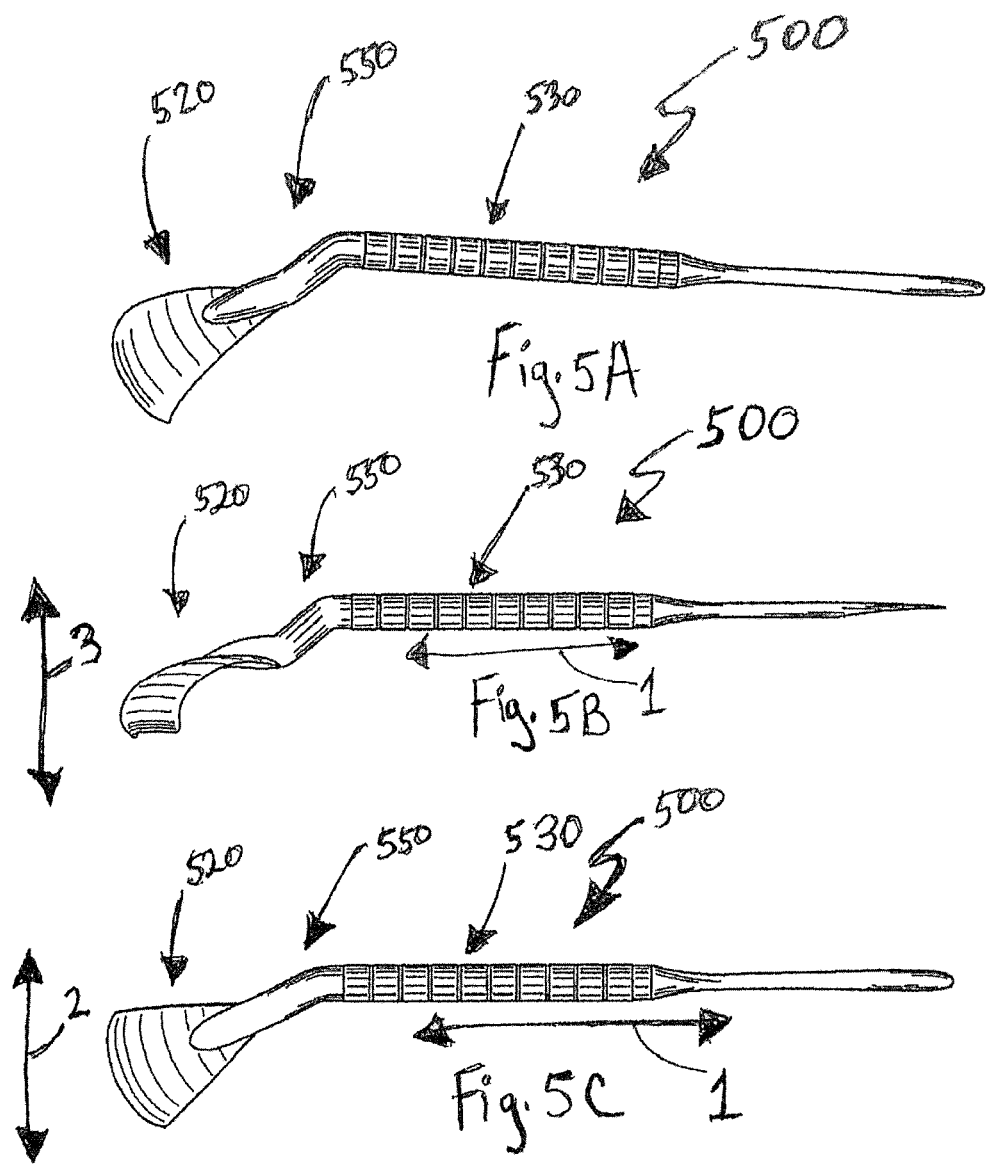

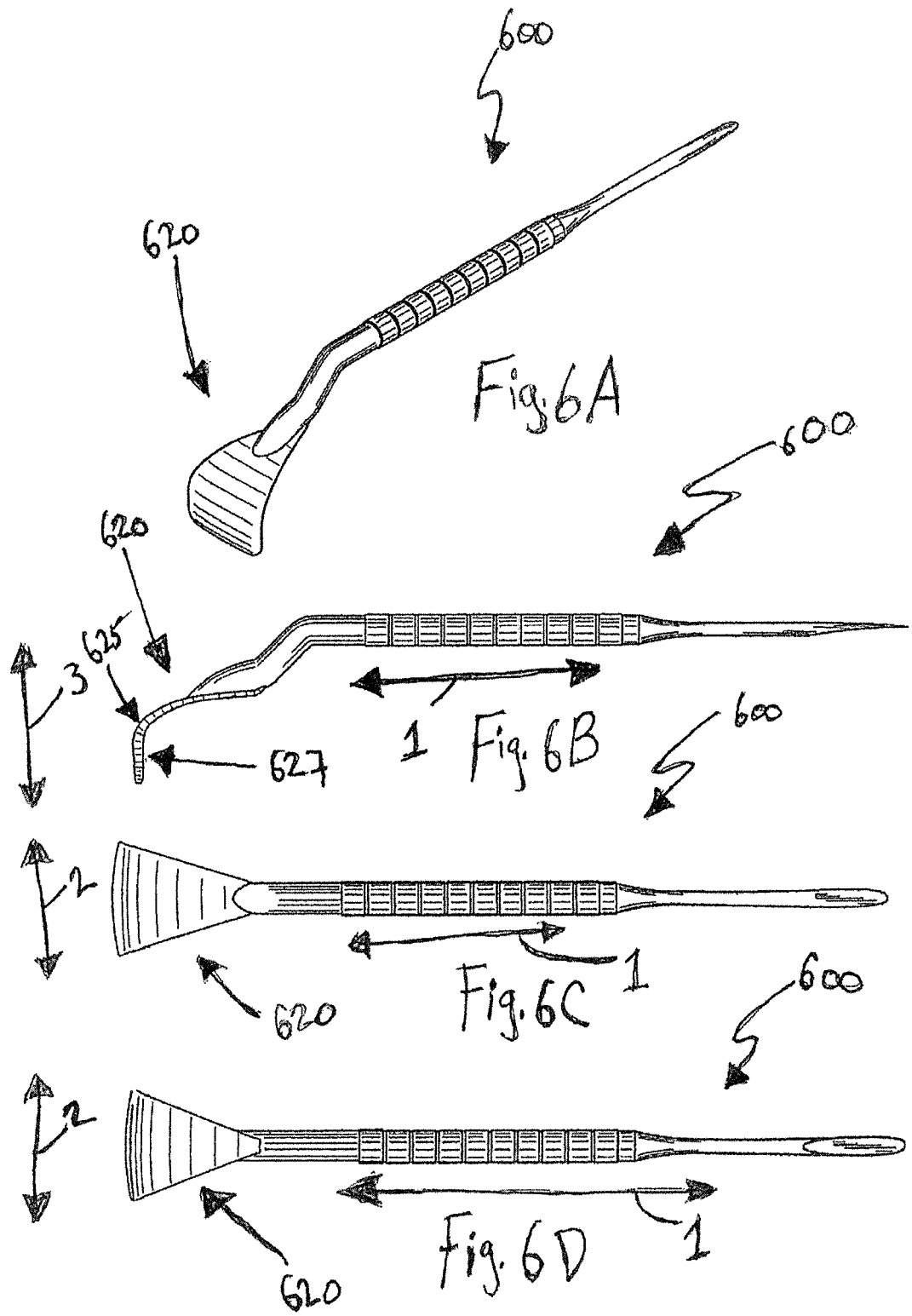

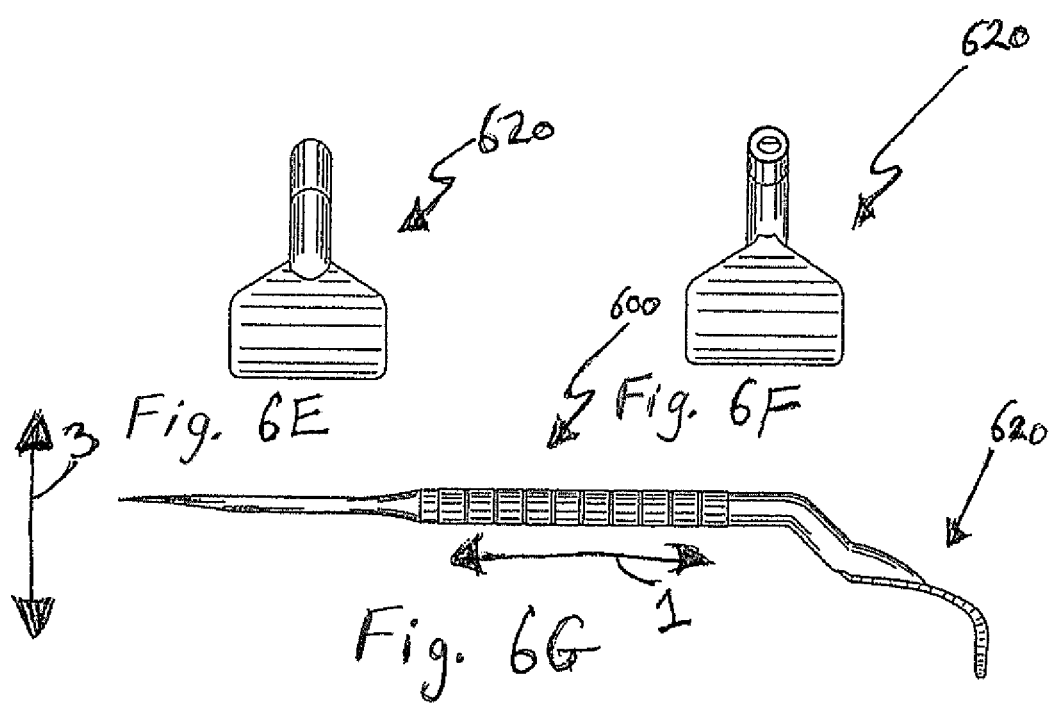

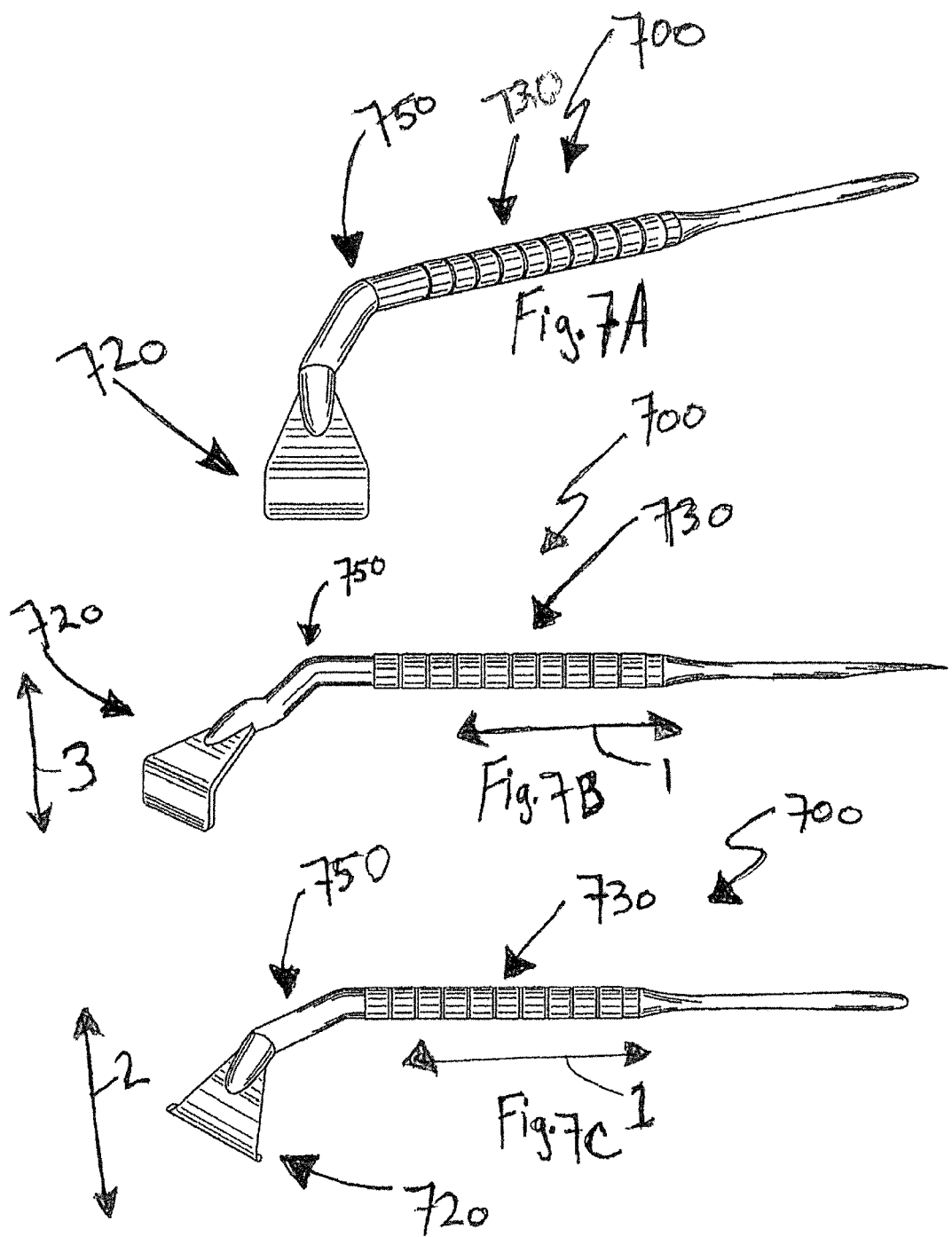

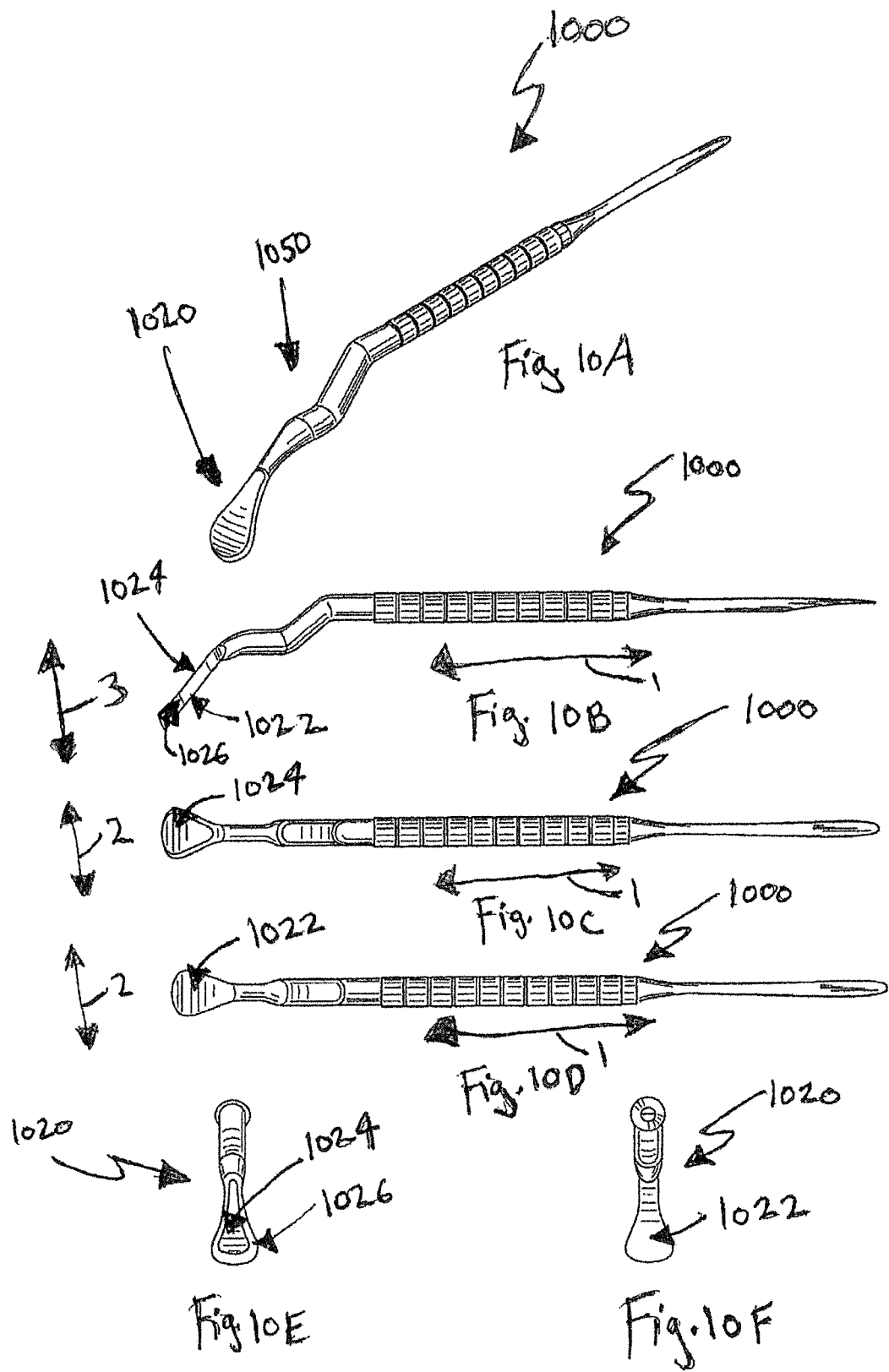

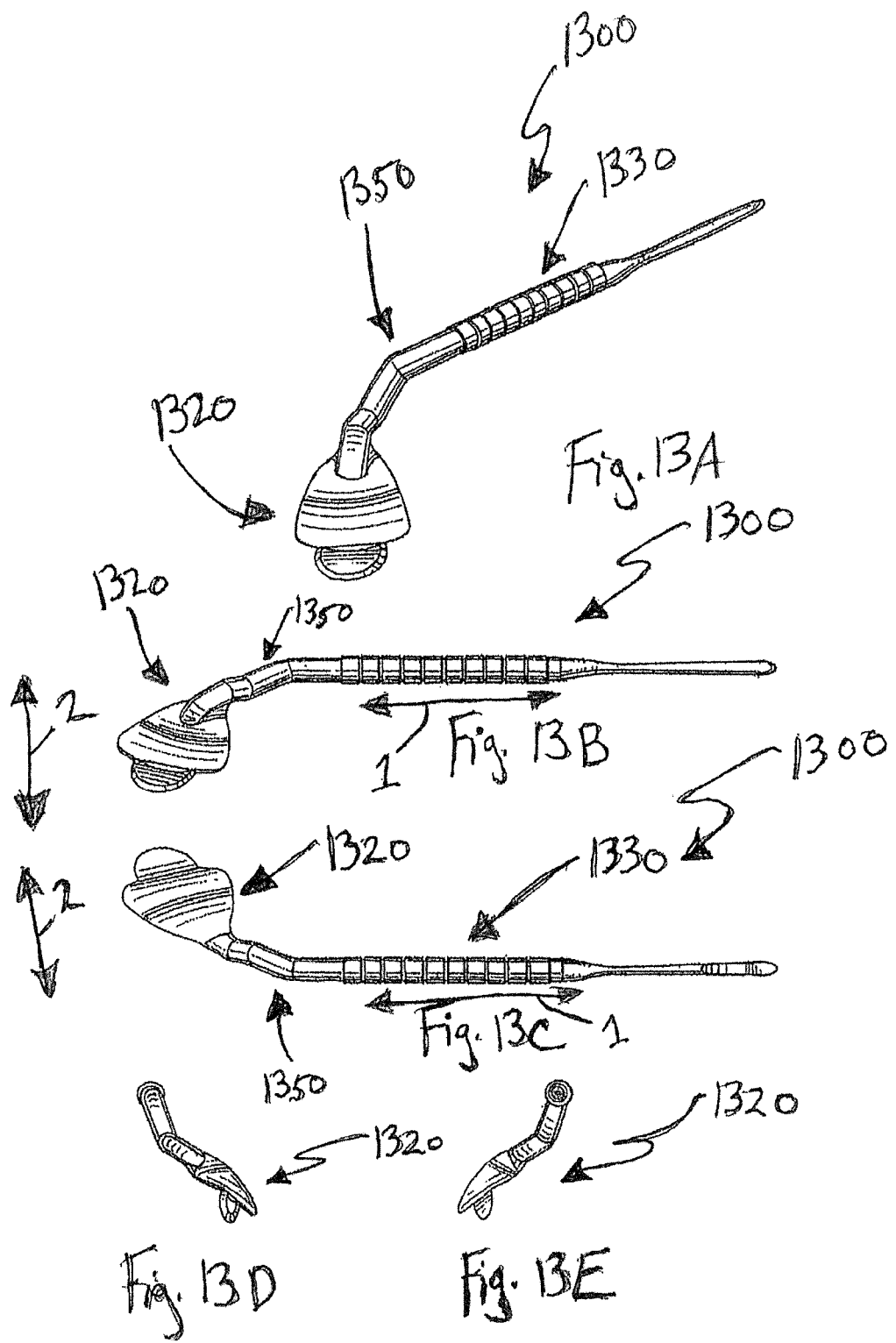

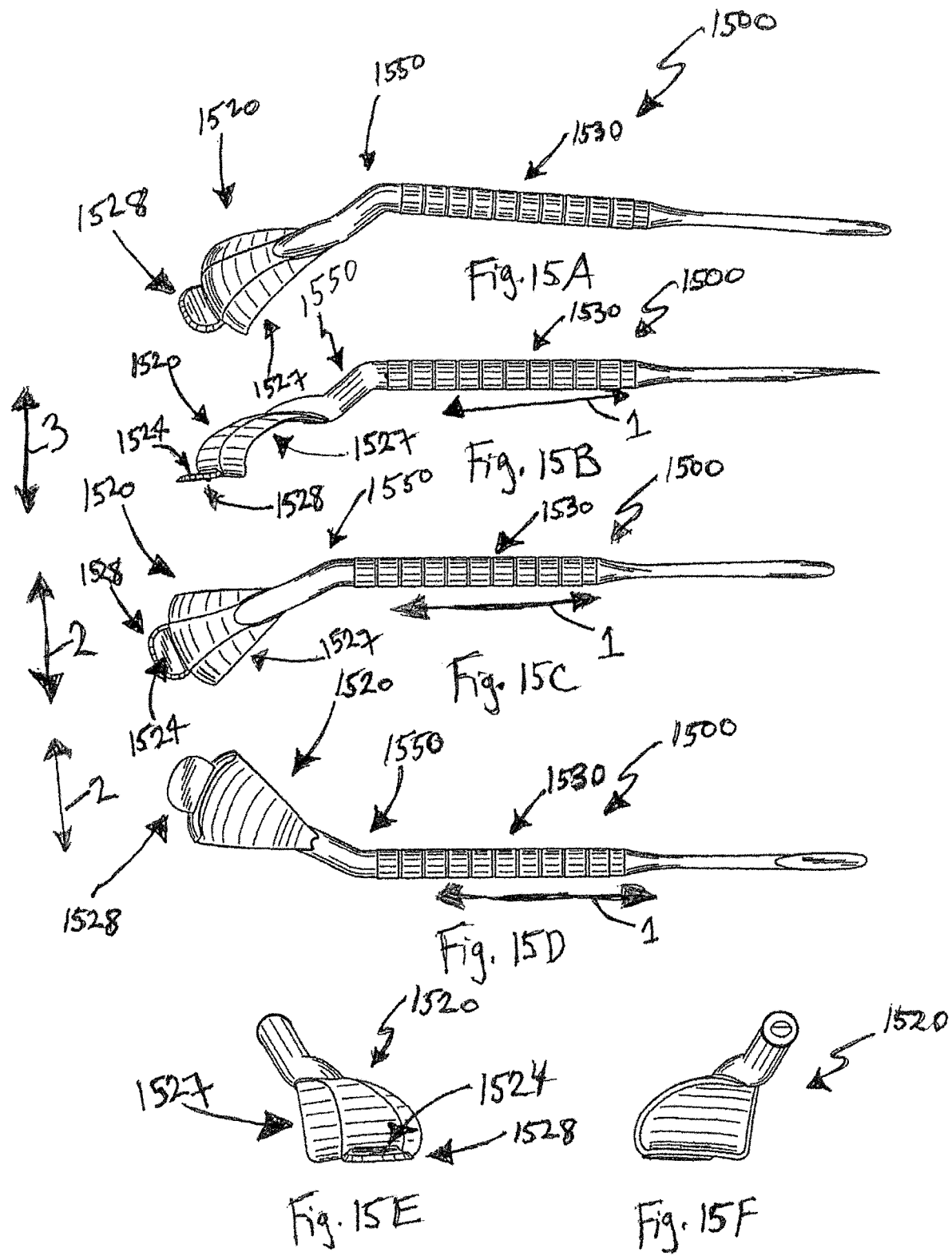

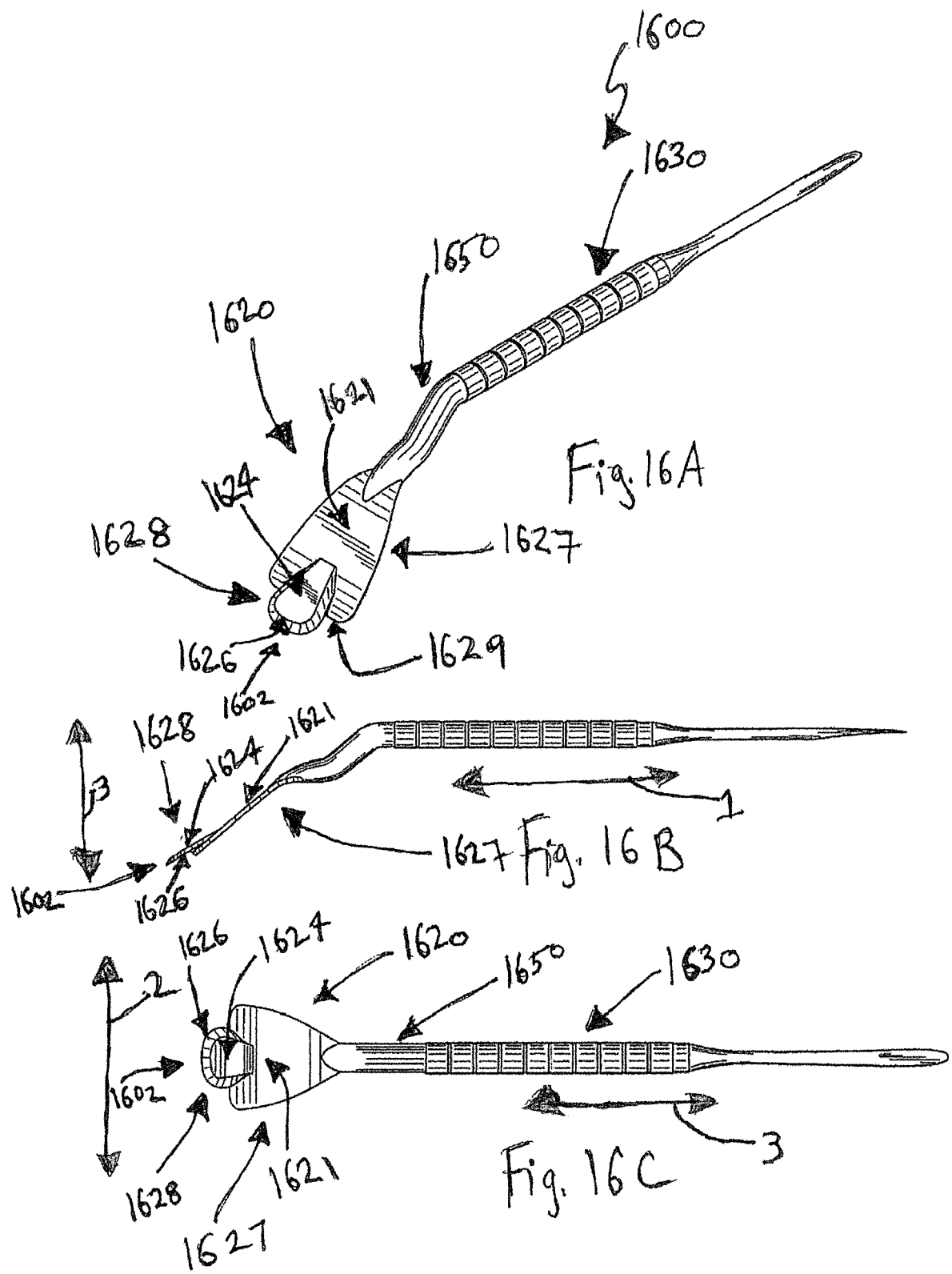

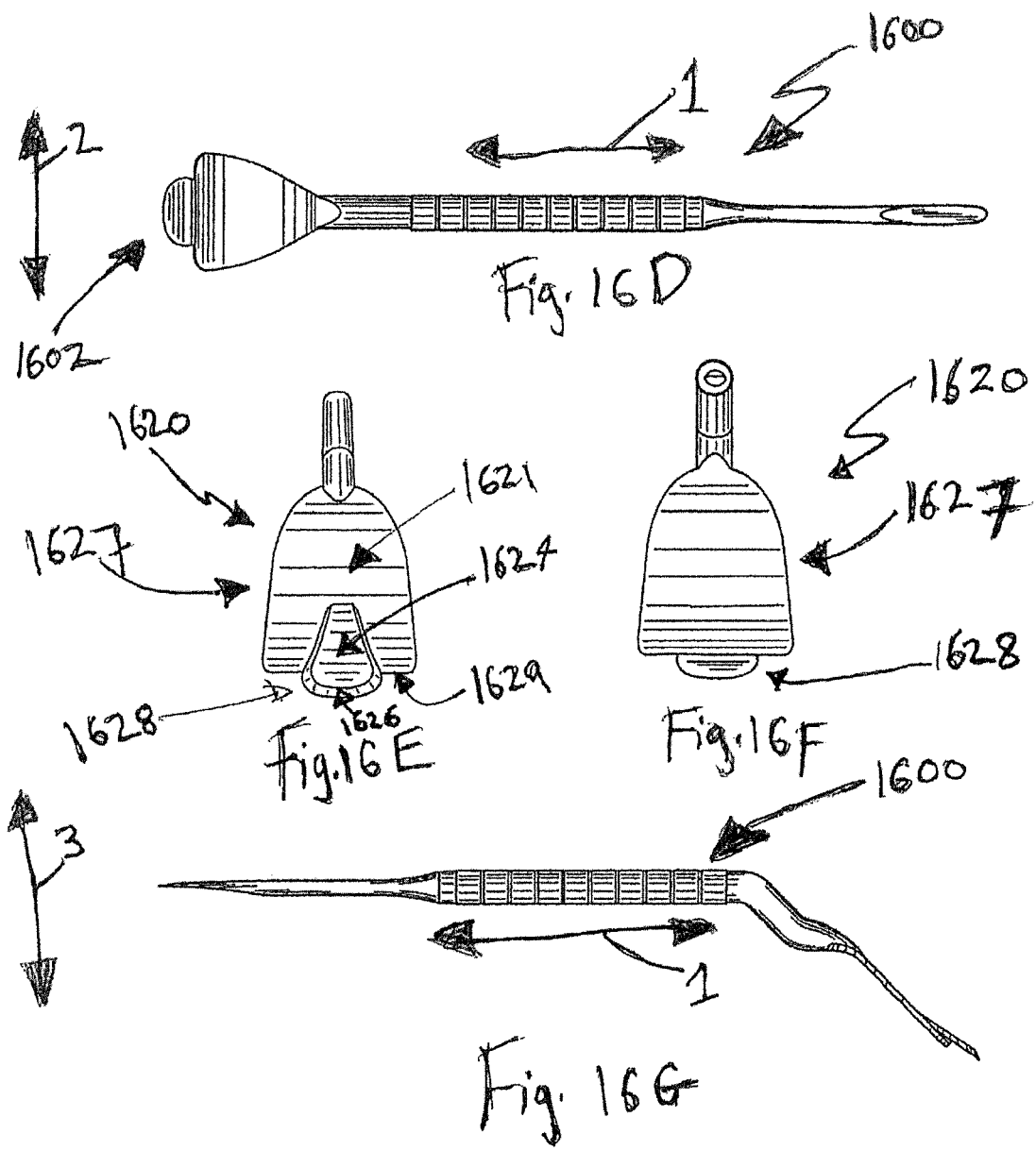

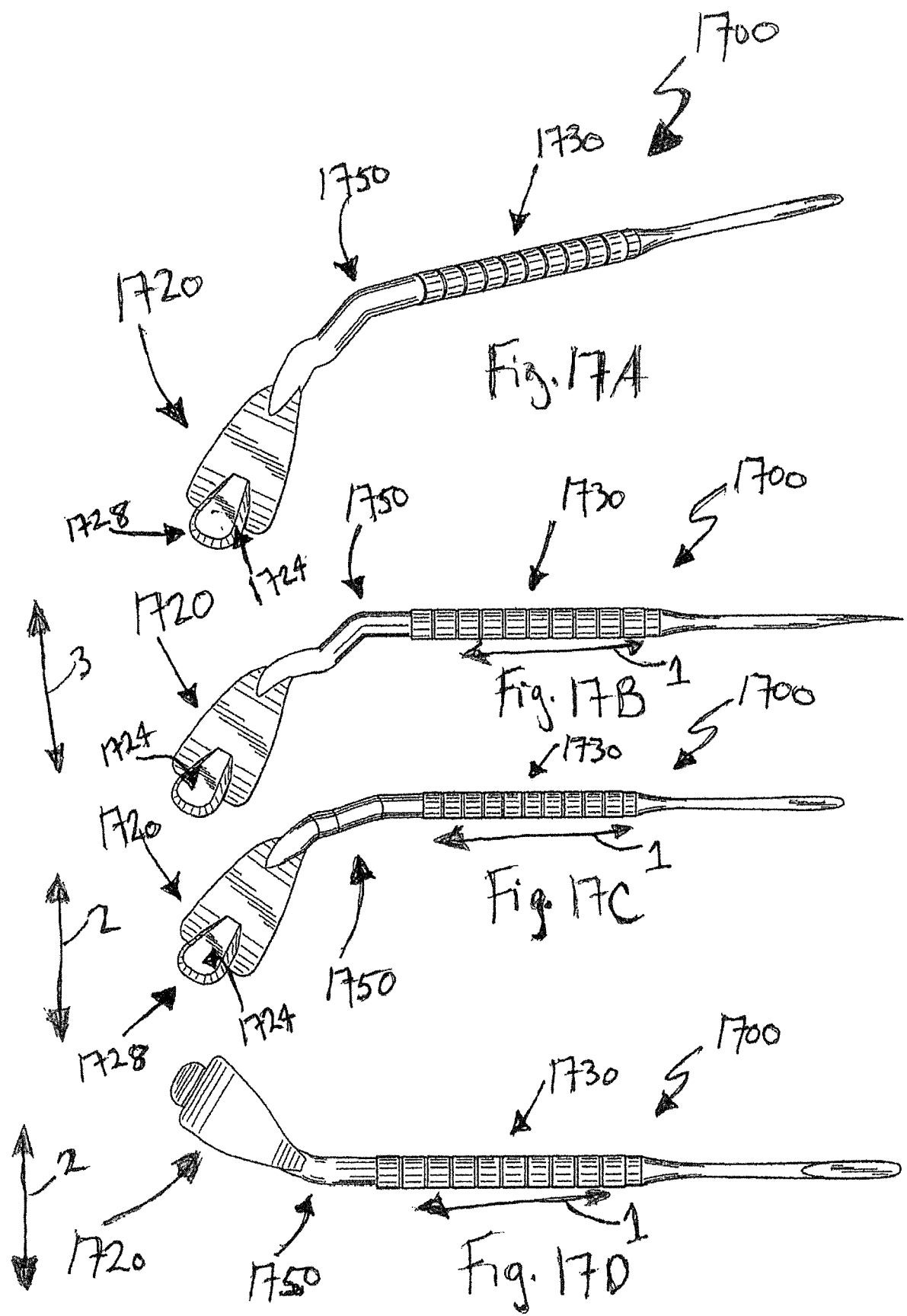

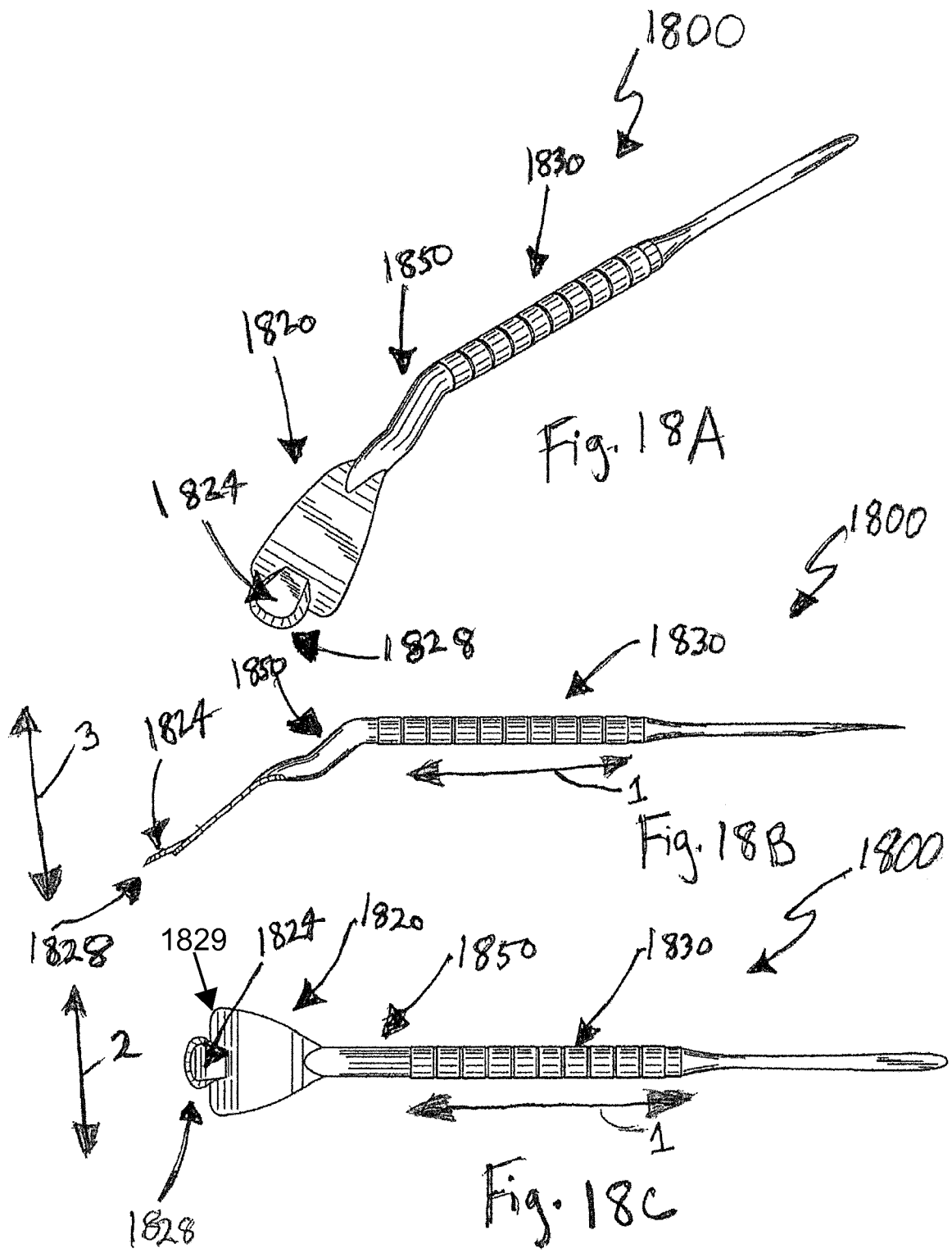

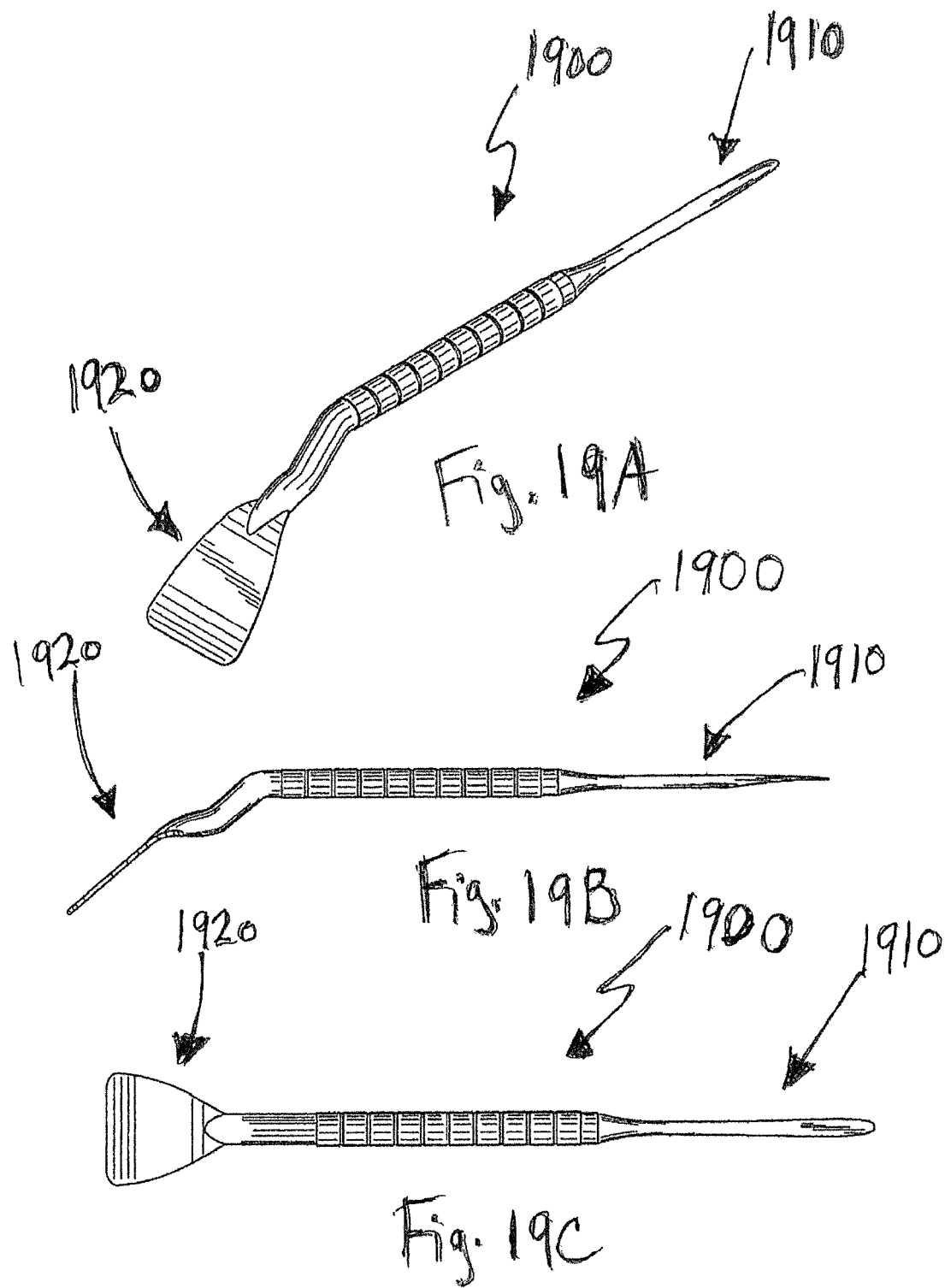

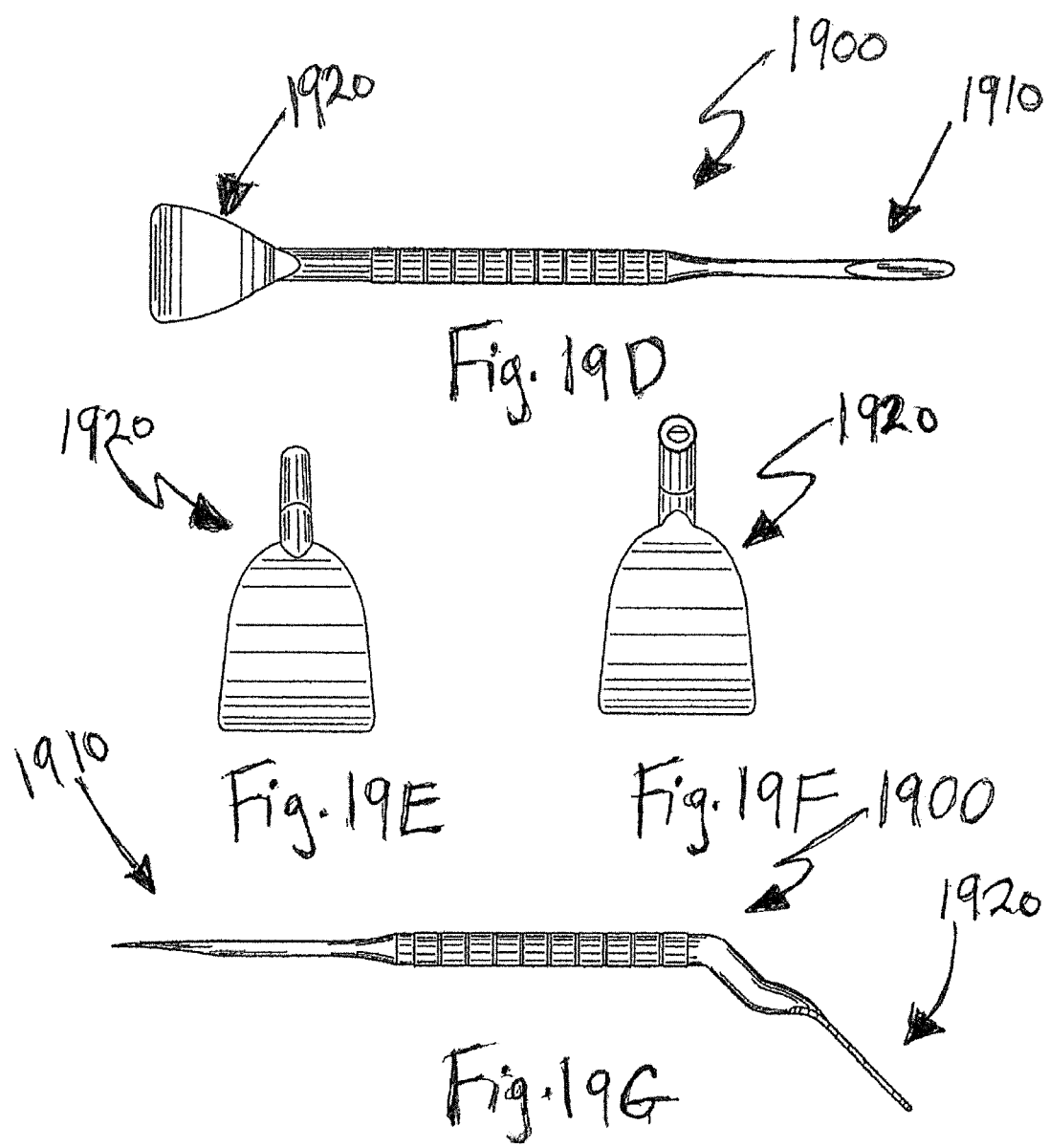

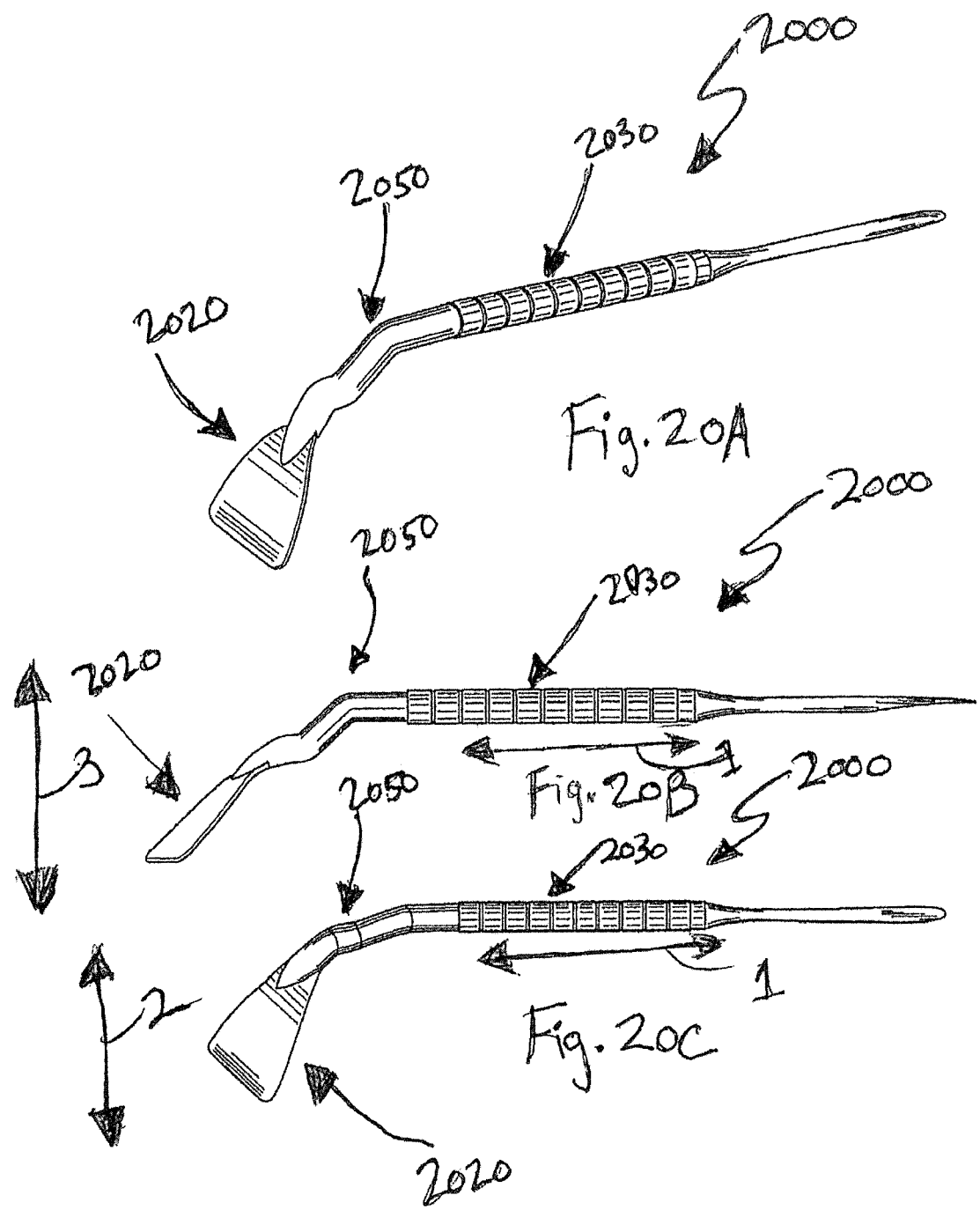

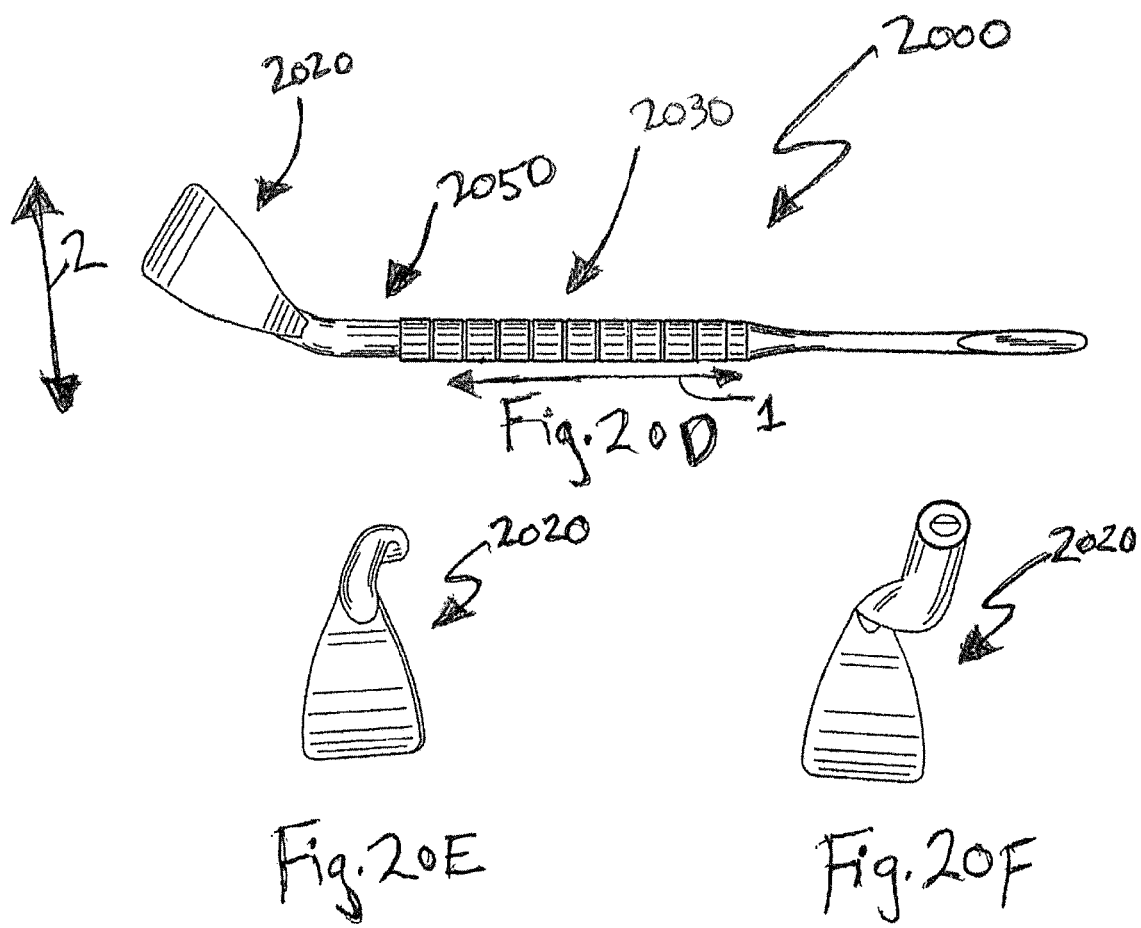

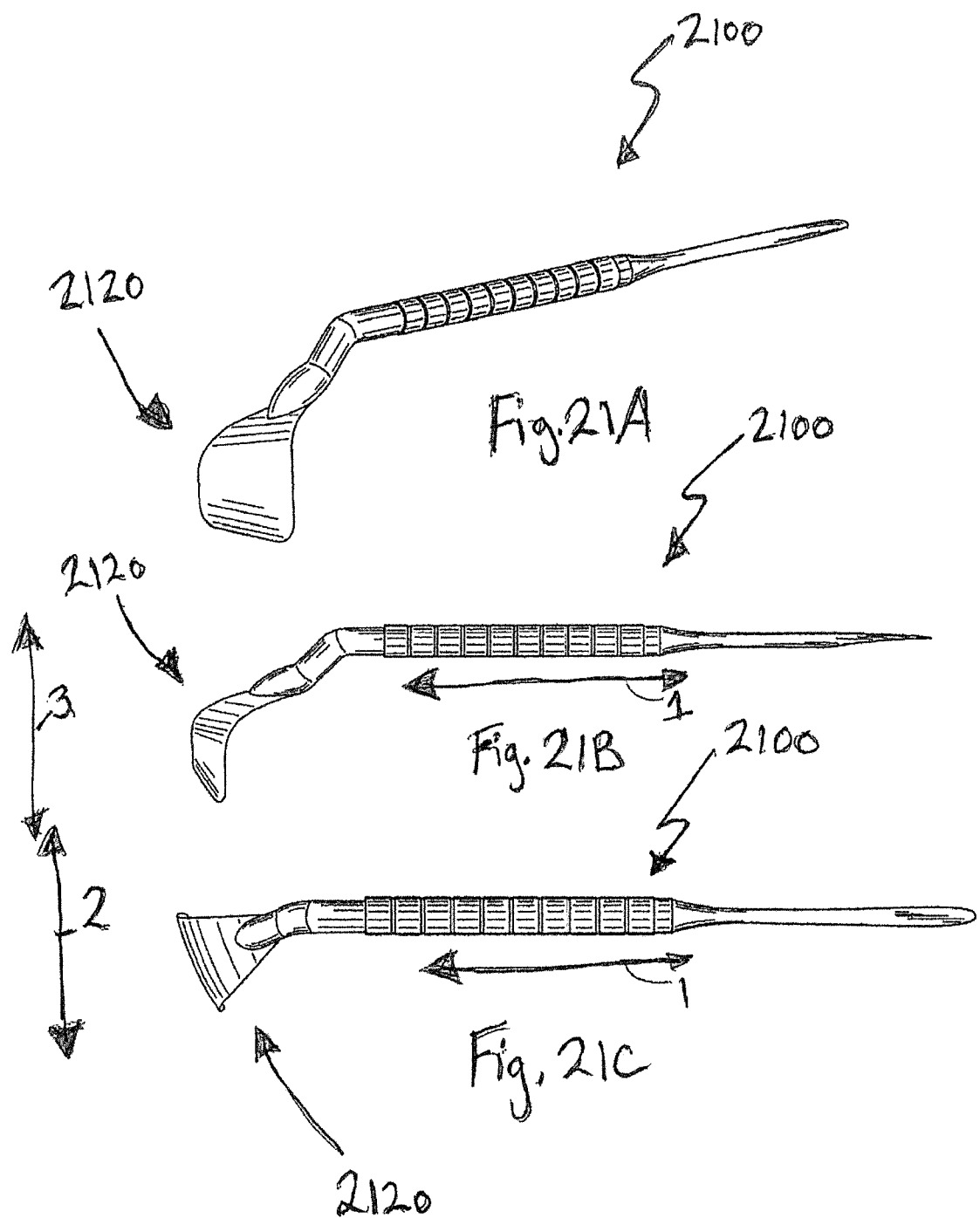

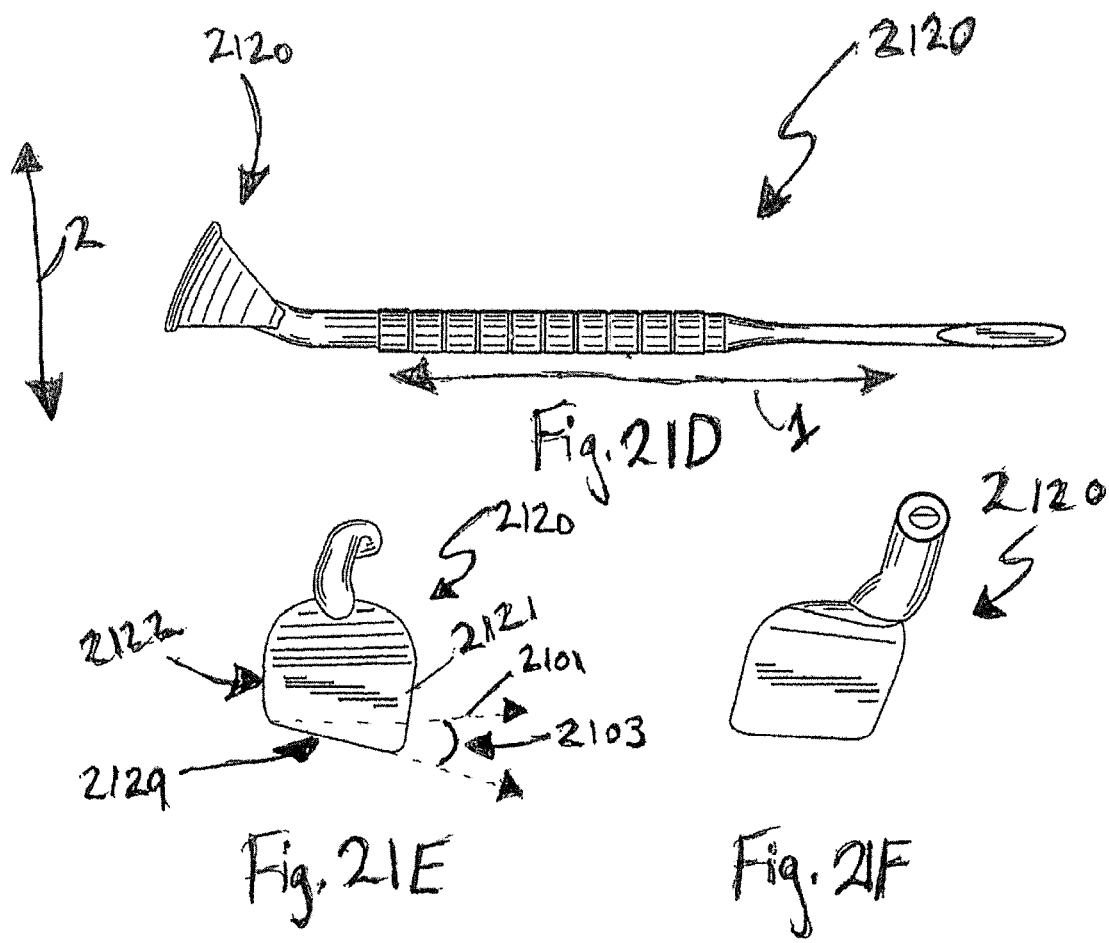

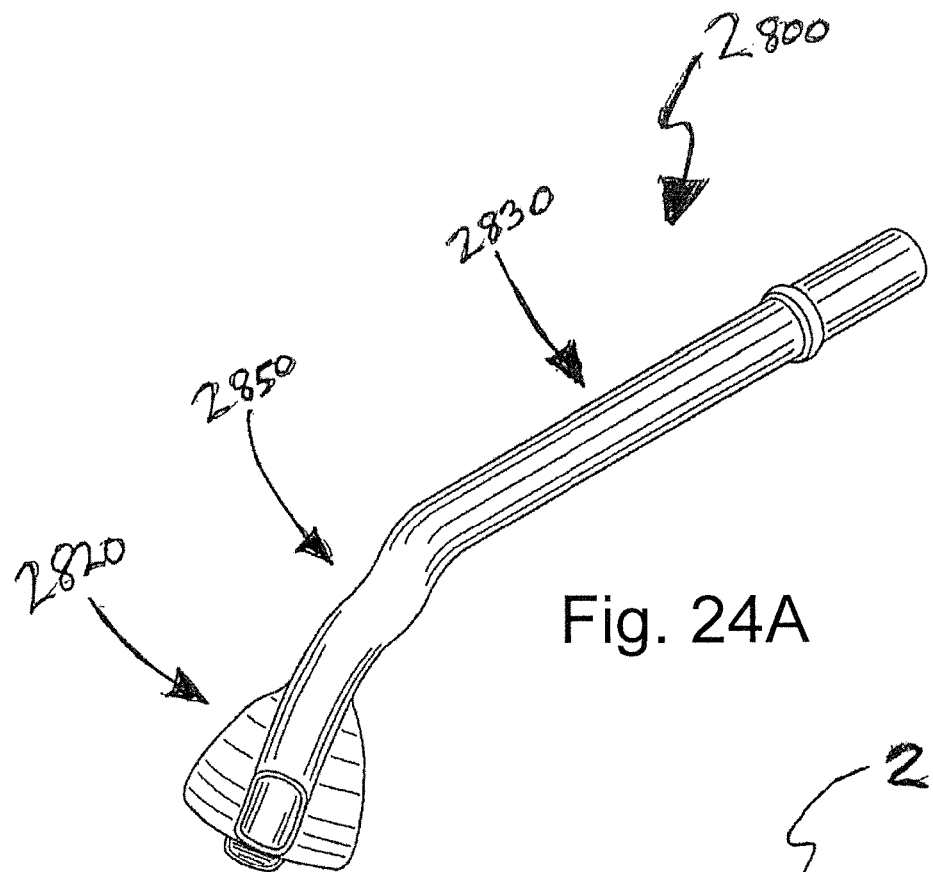
Fig. 24A
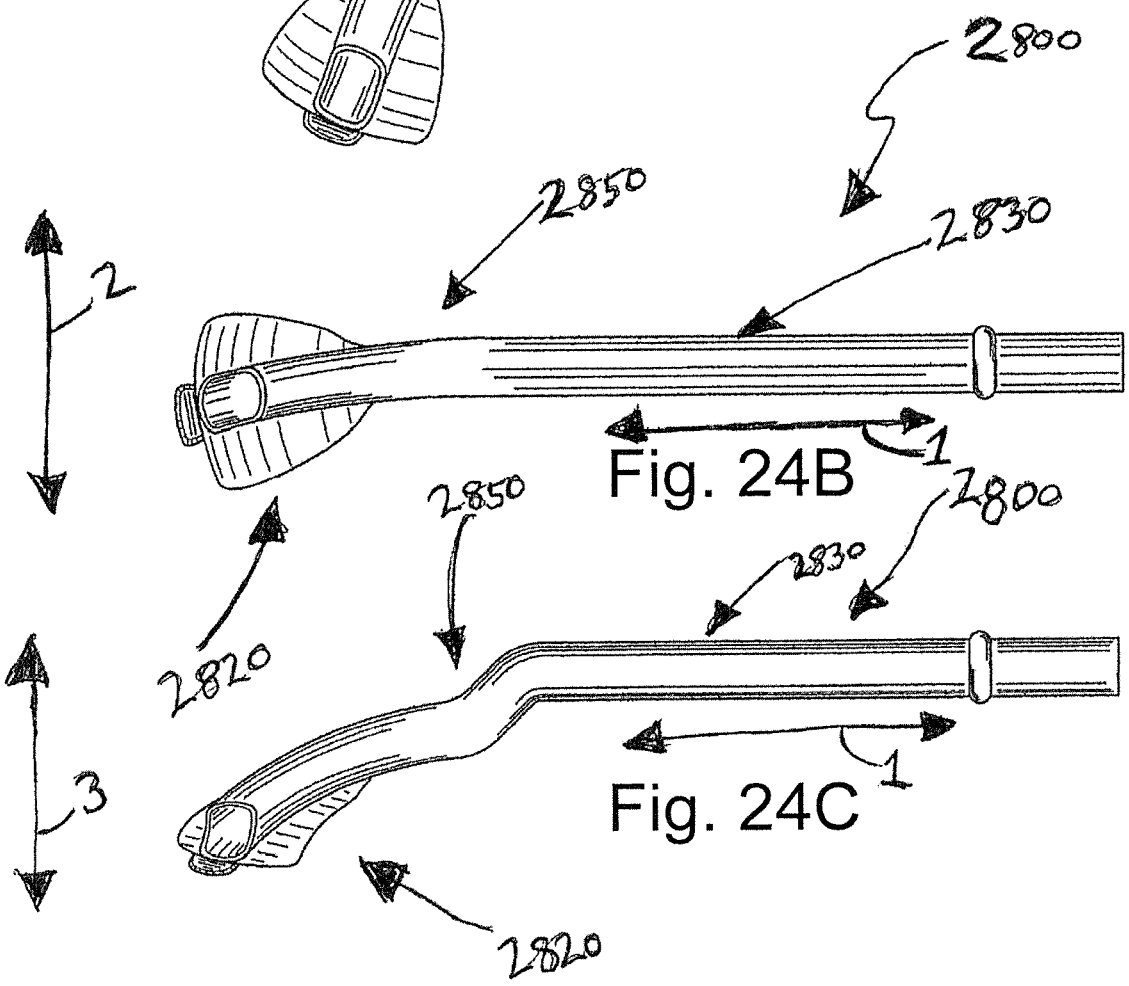
Fig. 24B
Fig. 24C

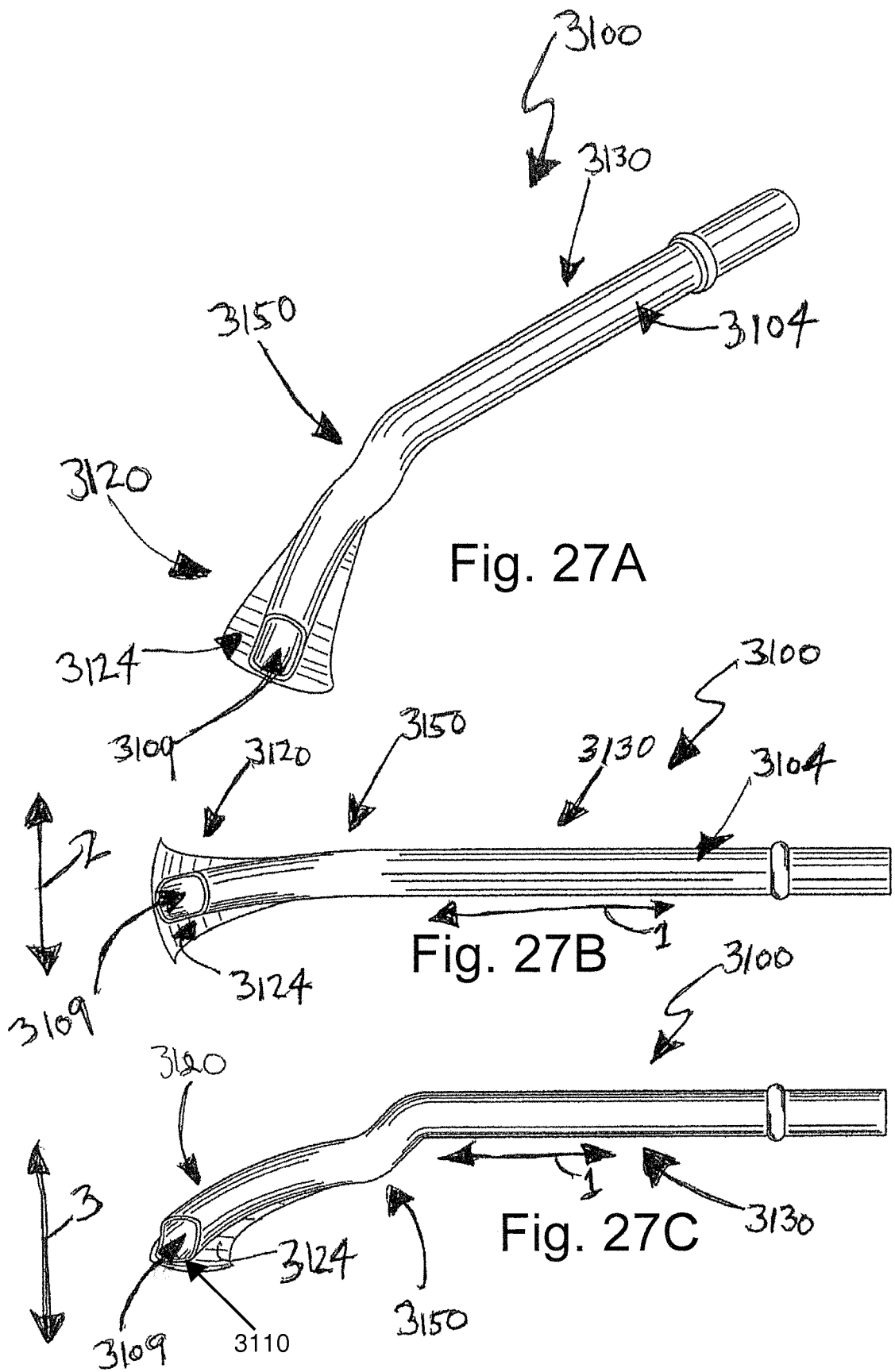

ERGONOMIC DENTAL TOOLS

CROSS-REFERENCE TO RELATED APPLICATIONS

This application is a continuation-in-part of U.S. patent application Ser. No. 13/624,257, filed on Sep. 21, 2012, with is a continuation of U.S. patent application Ser. No. 12/405,751, filed on Mar. 17, 2009, the contents of both of which are incorporated herein by reference in their entirety.

BACKGROUND OF THE INVENTION

1. Field of the Invention

The present invention generally relates to the fields of general dentistry, oral surgery and periodontal surgery and to surgical instrumentation used therein. More specifically, the invention relates to tongue and flap retractors, as well as suction tools, used in general dental procedures, periodontal and oral surgery.

2. Description of the Related Art

Many dental procedures require the precise use of surgical instruments within a small and restricted area of operation. Furthermore, it is usually desirable to selectively supply air or water to a treatment area, drill in a treatment area, or to manipulate soft tissue. To do so, Dentists have conventionally used various instruments to manipulate tissue, suction liquids or retract the tongue while performing the desired procedure. By way of example, a primary method used to retract tongue involves using a standard dental mirror. However, the size of the mirror and lack of proper physics and ergonomics makes this procedure needlessly difficult.

Hence, conventional methods frequently present various problems. For example, because of the restricted area, it is undesirable and usually impractical to crowd the oral cavity with multiple instruments. When two or three different instruments are placed in a patient's oral cavity, the practitioner is unable to clearly see the area of operation. Furthermore, because of the tight quarters, the instruments become limited in their range of motion. Thus, the degree of difficulty is unnecessarily increased for even the simplest of procedures.

The use of multiple instruments is impractical as it severely limits the ability of the general dentist, periodontal surgeon, oral surgeon or assistant (herein, "Dentist") to properly perform the required procedures. For instance if a Dentist uses one hand to retract the tongue and another to hold a surgical flap away from the treatment area, then he will need to ask for an assistant to reach for another instrument, or the assistant must hold an instrument and retract either the tongue or flap while he/she is simultaneously suctioning or performing a different task. The only other option would be to perform the operation in segments or go back and forth between instruments until the procedure is complete. This unnecessary complexity lengthens the time of operation, reduces the efficiency of the procedure and increases patient discomfort.

Finally, a common problem in the field is that Dentists regularly complain of neck, back and shoulder pain, as well as pain related to carpal tunnel syndrome. In fact, a comprehensive literature search indicates dental care providers are at a high risk for suffering workplace musculoskeletal disorders (WMSD) and neuromuscular disorders, e.g. disc herniation. Studies have reported that Dentists who suffer a WMSD injury have a lost work day average of 93 days per incident. In fact, sixty-two percent of dental hygienists have complained of neck problems and eighty-one percent have complained of shoulder pain in one or both shoulders. Studies have also shown that between six and seven percent of all dental hygienists report being diagnosed with carpal tunnel syndrome and that fifty-nine percent of dentists have reported musculoskeletal pain. A survey of a U.S. Army dental clinic reported that over seventy-five percent of all dental workers complained of one or more carpal tunnel syndrome symptoms, over fifty percent complained of back and shoulder pain, and eleven percent were diagnosed as having carpal tunnel syndrome. These disorders and others can be addressed with proper emphasis on ergonomics and posture, and by shortening the length of the dental procedure.

Thus, missing from the art is an invention that allows greater control, while affording the Dentist an opportunity to practice with better posture. Moreover, an invention that reduces the time of operation would have several benefits for both patients and Dentists by: (i) reducing strain on the neck, back, shoulders and hands of Dentists, (ii) reducing the amount of discomfort experienced by patients during procedures in which they remain awake, and (iii) reducing the adverse risks to the patient associated with the use of general anesthesia in situations where patients are anesthetized for a procedure.

SUMMARY OF THE INVENTION

One embodiment of the invention is directed to a combination tongue and surgical flap retractor. The combination retractor may include an operational unit, a neck region and a handle region. The operational unit further includes a tongue retractor and a flap retractor. The tongue retractor may be formed with a concave shape, a flat shape, or with an increased overall thickness of the operational unit. The flap retractor may be formed with a tapered extended edge or tab, which can be made in various lengths. Furthermore, the flap retractor may also include a beveled edge. The combination retractor may be formed in a way such that the tongue retractor is disposed on a different plane than the flap retractor. The retractor may also include a suction mechanism for eliminating fluids such as saliva, water, and blood from the oral cavity.

The present invention is also directed to improved ergonomics in the neck region of the operational unit. In one embodiment, the neck region contains an S-shaped design for better ergonomics. In embodiments, the neck region extends in a downward and distal direction continuously from its proximal end to its distal end with respect to the axis of the handle. Furthermore, the neck region may also include a lateral bend positioned at the proximal end of the operational unit, so as to position the operational unit either to the right or the left with respect to the central axis of the handle. Also, a rotational offset may be incorporated in the working end in order to further help to accommodate the tool to the anatomy of the mandible and the position of the patient's mouth during a procedure. Therefore, this facilitates specific use on a respective side of the mouth based on the direction of the lateral bend.

Finally, the present invention is directed to improvements in the handle region of the combination retractor. In one embodiment, the handle region includes a grip portion having various widths so that the Dentist can choose a pen grasp or a palm grasp depending on the individual preferences of the Dentist. The proximal end of the handle region may further include a dental pick, a dental probe, a dental hook, a periosteal elevator, or a periosteal retractor or any other dental instrument.

Other features and advantages of the present invention will become more fully apparent and understood with reference to the following description, the accompanying drawings and the appended claims.

BRIEF DESCRIPTION OF THE DRAWINGS

The various aspects and embodiments disclosed herein will be better understood when read in conjunction with the appended drawings, wherein like reference numerals refer to like components. For the purposes of illustrating aspects of the present application, there are shown in the drawings certain preferred embodiments. It should be understood, however, that the application is not limited to the precise arrangement, structures, features, embodiments, aspects, and devices shown, and the arrangements, structures, features, embodiments, aspects and devices shown may be used singularly or in combination with other arrangements, structures, features, embodiments, aspects and devices. The drawings are not necessarily drawn to scale and are not in any way intended to limit the scope of this invention, but are merely presented to clarify illustrated embodiments of the invention. In these drawings:

FIG. 1A is a perspective view of a first embodiment dental tool.

FIG. 1B is a side view of the dental tool of FIG. 1A.

FIG. 1C is a top view of the dental tool of FIG. 1A.

FIG. 1D is a bottom view of the dental tool of FIG. 1A.

FIG. 1E is a top detailed view of a tongue retractor portion of the dental tool shown in FIG. 1A.

FIG. 1F is a bottom detailed view of a tongue refractor portion of the dental tool shown in FIG. 1A.

FIG. 2A is a perspective view of a second embodiment dental tool.

FIG. 2B is a side view of the dental tool of FIG. 2A.

FIG. 2C is a top view of the dental tool of FIG. 2A.

FIG. 2D is a bottom view of the dental tool of FIG. 2A.

FIG. 2E is a top detailed view of a tongue refractor portion of the dental tool shown in FIG. 2A.

FIG. 2F is a bottom detailed view of a tongue refractor portion of the dental tool shown in FIG. 2A.

FIG. 3A is a perspective view of a third embodiment dental tool.

FIG. 3B is a side view of the dental tool of FIG. 3A.

FIG. 3C is a top view of the dental tool of FIG. 3A.

FIG. 4A is a perspective view of a fourth embodiment dental tool.

FIG. 4B is a side view of the dental tool of FIG. 4A.

FIG. 4C is a top view of the dental tool of FIG. 4A.

FIG. 4D is a bottom view of the dental tool of FIG. 4A.

FIG. 4E is a top detailed view of a tongue retractor portion of the dental tool shown in FIG. 4A.

FIG. 4F is a bottom detailed view of a tongue refractor portion of the dental tool shown in FIG. 4A.

FIG. 5A is a perspective view of a fifth embodiment dental tool.

FIG. 5B is a side view of the dental tool of FIG. 5A.

FIG. 5C is a top view of the dental tool of FIG. 5A.

FIG. 6A is a perspective view of a sixth embodiment dental tool.

FIG. 6B is a left side view of the dental tool of FIG. 6A.

FIG. 6C is a top view of the dental tool of FIG. 6A.

FIG. 6D is a bottom view of the dental tool of FIG. 6A.

FIG. 6E is a top detailed view of a tongue retractor portion of the dental tool shown in FIG. 6A.

FIG. 6F is a bottom detailed view of a tongue refractor portion of the dental tool shown in FIG. 6A.

FIG. 6G is a right side view of the dental tool of FIG. 6A.

FIG. 7A is a perspective view of a seventh embodiment dental tool.

FIG. 7B is a side view of the dental tool of FIG. 7A.

FIG. 7C is a top view of the dental tool of FIG. 7A.

FIG. 10A is a perspective view of a tenth embodiment dental tool.

FIG. 10B is a side view of the dental tool of FIG. 10A.

FIG. 10C is a top view of the dental tool of FIG. 10A.

FIG. 10D is a bottom view of the dental tool of FIG. 10A.

FIG. 10E is a top detailed view of a flap retractor portion of the dental tool shown in FIG. 10A.

FIG. 10F is a bottom detailed view of a flap retractor portion of the dental tool shown in FIG. 10A.

FIG. 13A is a perspective view of a thirteenth embodiment dental tool.

FIG. 13B is a top view of the dental tool of FIG. 13A.

FIG. 13C is a bottom view of the dental tool of FIG. 13A.

FIG. 13D is a top detailed view of a combined tongue and flap retractor portion of the dental tool shown in FIG. 13A.

FIG. 13E is a bottom detailed view of a combined tongue and flap refractor portion of the dental tool shown in FIG. 13A.

FIG. 15A is a perspective view of a fifteenth embodiment dental tool.

FIG. 15B is a side view of the dental tool of FIG. 15A.

FIG. 15C is a top view of the dental tool of FIG. 15A.

FIG. 15D is a bottom view of the dental tool of FIG. 15A.

FIG. 15E is a top detailed view of a combined tongue and flap retractor portion of the dental tool shown in FIG. 15A.

FIG. 15F is a bottom detailed view of a combined tongue and flap retractor portion of the dental tool shown in FIG. 15A.

FIG. 16A is a perspective view of a sixteenth embodiment dental tool.

FIG. 16B is a left side view of the dental tool of FIG. 16A.

FIG. 16C is a top view of the dental tool of FIG. 16A.

FIG. 16D is a bottom view of the dental tool of FIG. 16A.

FIG. 16E is a top detailed view of a combined tongue and flap retractor portion of the dental tool shown in FIG. 16A.

FIG. 16F is a bottom detailed view of a combined tongue and flap retractor portion of the dental tool shown in FIG. 16A.

FIG. 16G is a right side view of the dental tool of FIG. 16A.

FIG. 17A is a perspective view of a seventeenth embodiment dental tool.

FIG. 17B is a side view of the dental tool of FIG. 17A.

FIG. 17C is a top view of the dental tool of FIG. 17A.

FIG. 17D is a bottom view of the dental tool of FIG. 17A.

FIG. 18A is a perspective view of a eighteenth embodiment dental tool.

FIG. 18B is a left side view of the dental tool of FIG. 18A.

FIG. 18C is a top view of the dental tool of FIG. 18A.

FIG. 19A is a perspective view of a nineteenth embodiment dental tool.

FIG. 19B is a left side view of the dental tool of FIG. 19A.

FIG. 19C is a top view of the dental tool of FIG. 19A.

FIG. 19D is a bottom view of the dental tool of FIG. 19A.

FIG. 19E is a top detailed view of a tongue retractor portion of the dental tool shown in FIG. 19A.

FIG. 19F is a bottom detailed view of a tongue retractor portion of the dental tool shown in FIG. 19A.

FIG. 19G is a right side view of the dental tool of FIG. 19A.

FIG. 20A is a perspective view of a twentieth embodiment dental tool.

FIG. 20B is a side view of the dental tool of FIG. 20A.

FIG. 20C is a top view of the dental tool of FIG. 20A.

FIG. 20D is a bottom view of the dental tool of FIG. 20A.

FIG. 20E is a top detailed view of a tongue retractor portion of the dental tool shown in FIG. 20A.

FIG. 20F is a bottom detailed view of a tongue retractor portion of the dental tool shown in FIG. 20A.

FIG. 21A is a perspective view of a twenty-first embodiment dental tool.

FIG. 21B is a side view of the dental tool of FIG. 21A.

FIG. 21C is a top view of the dental tool of FIG. 21A.

FIG. 21D is a bottom view of the dental tool of FIG. 21A.

FIG. 21E is a top detailed view of a tongue retractor portion of the dental tool shown in FIG. 21A.

FIG. 21F is a bottom detailed view of a tongue retractor portion of the dental tool shown in FIG. 21A.

Figure 22A:
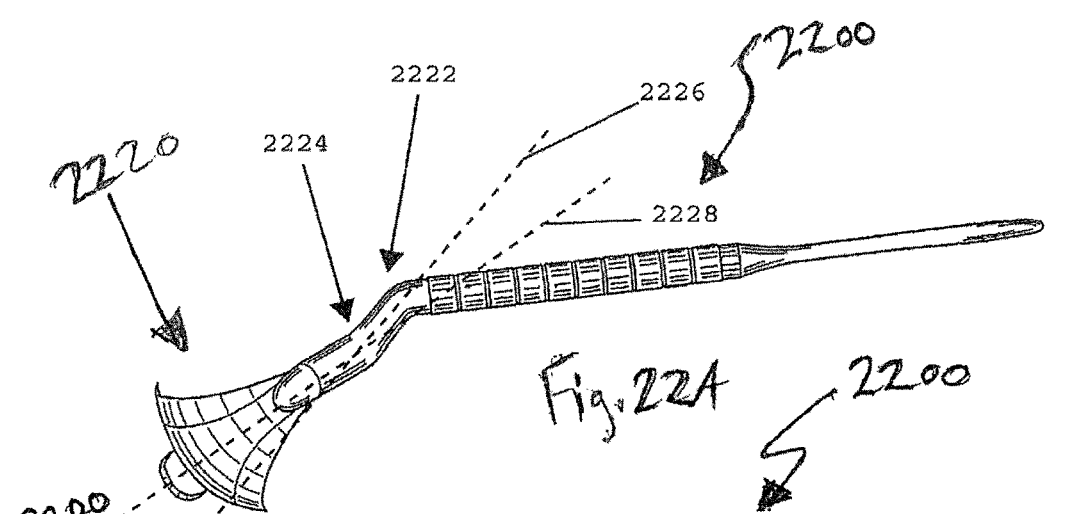

FIG. 22A is a perspective view of a twenty-second embodiment dental tool.

Figure 22B:
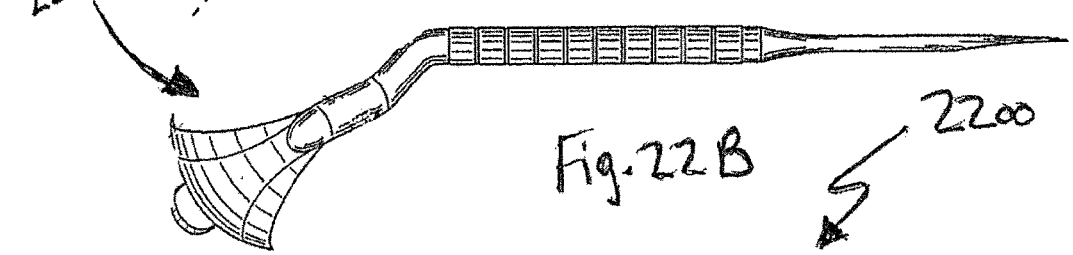

FIG. 22B is a side view of the dental tool of FIG. 22A.

Figure 22C:
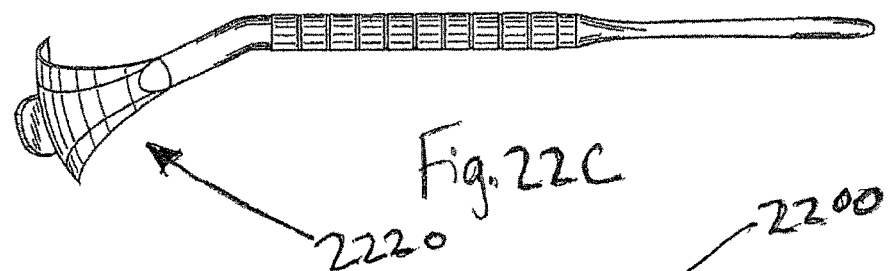

FIG. 22C is a top view of the dental tool of FIG. 22A.

Figure 22D:
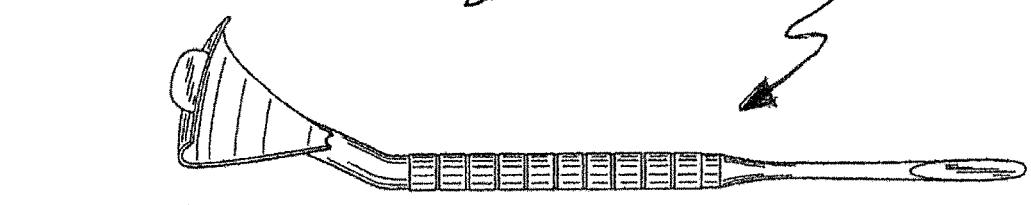

FIG. 22D is a bottom view of the dental tool of FIG. 22A.

Figure 22E:
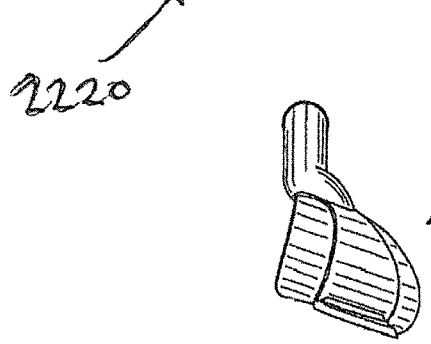

FIG. 22E is a top detailed view of a combined tongue and flap retractor portion of the dental tool shown in FIG. 22A.

Figure 22F:
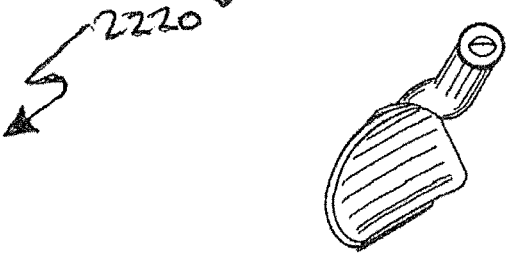

FIG. 22F is a bottom detailed view of a combined tongue and flap retractor portion of the dental tool shown in FIG. 22A.

Figure 23A:
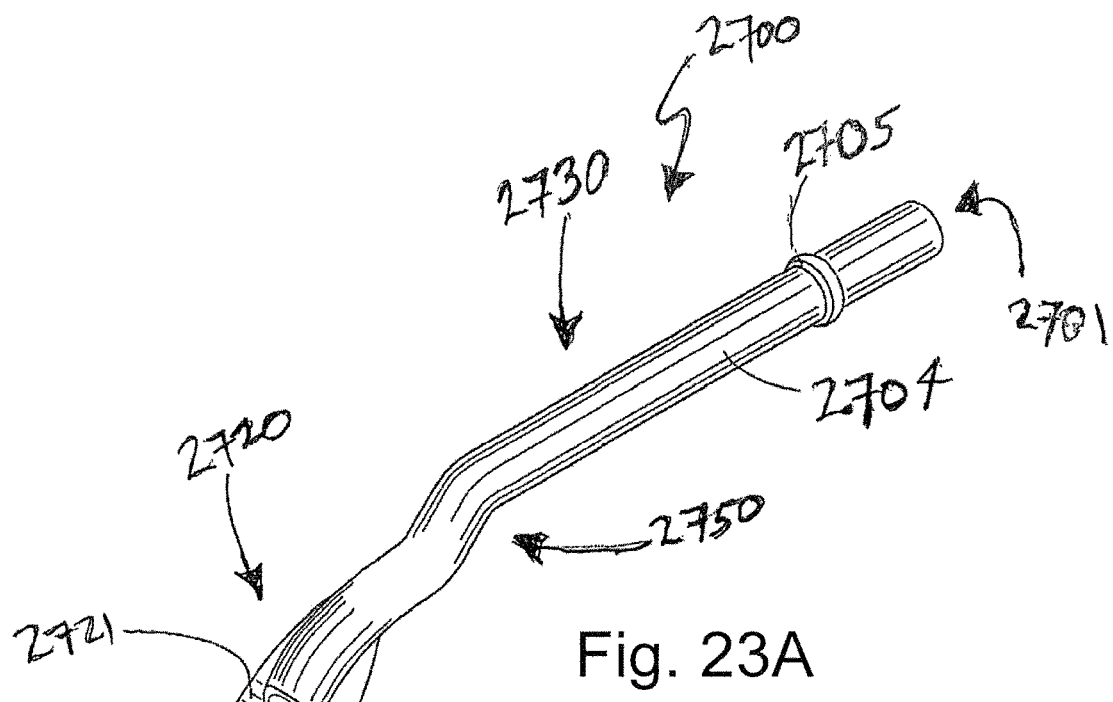

FIG. 23A is a perspective view of a twenty-third embodiment dental tool.

Figure 23B:
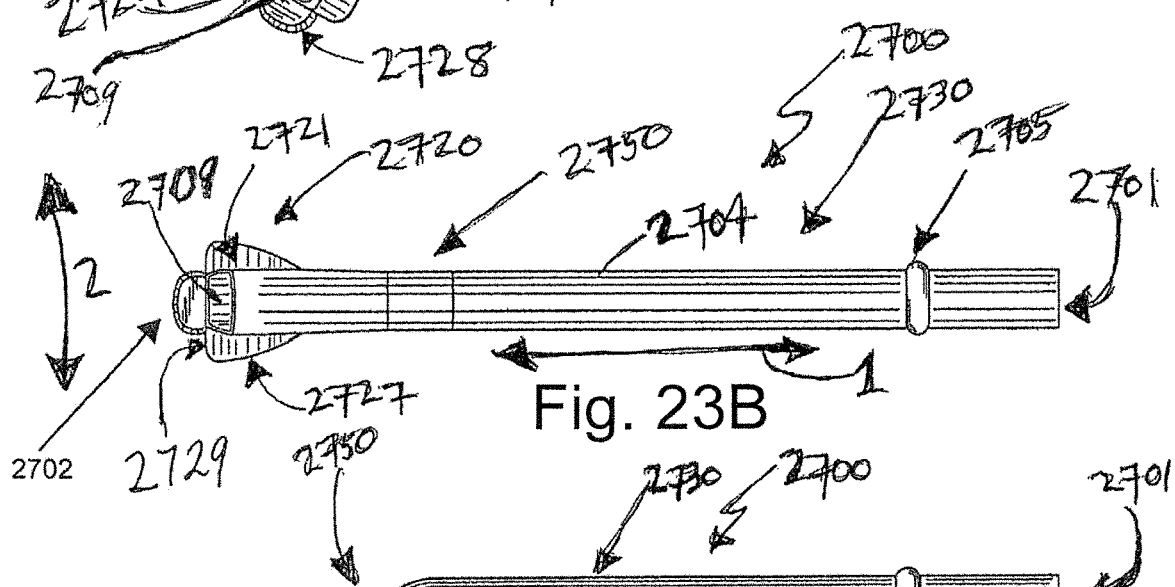

FIG. 23B is a top view of the dental tool of FIG. 23A.

Figure 23C:
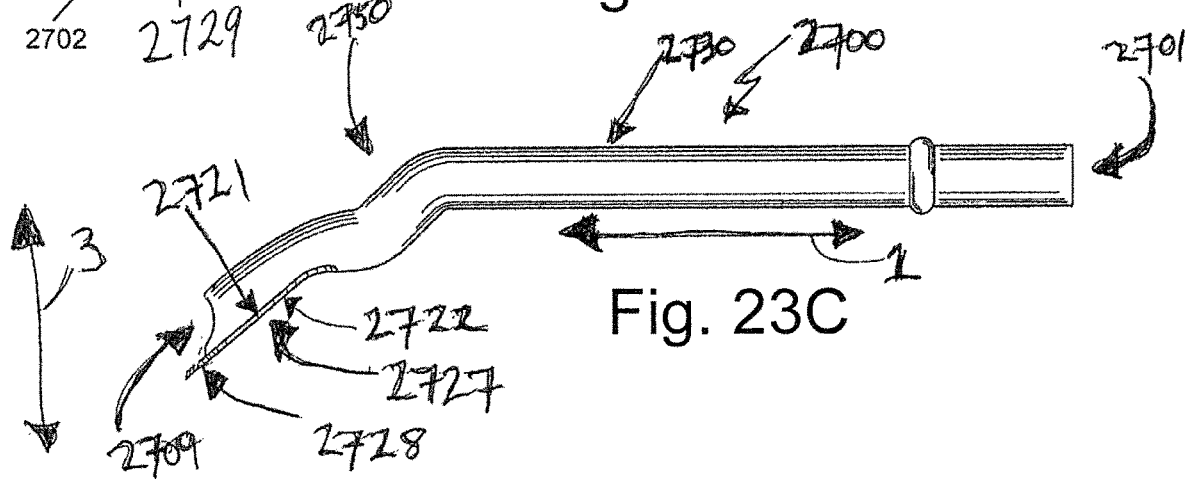

FIG. 23C is a side view of the dental tool of FIG. 23A.

Figure 23D:
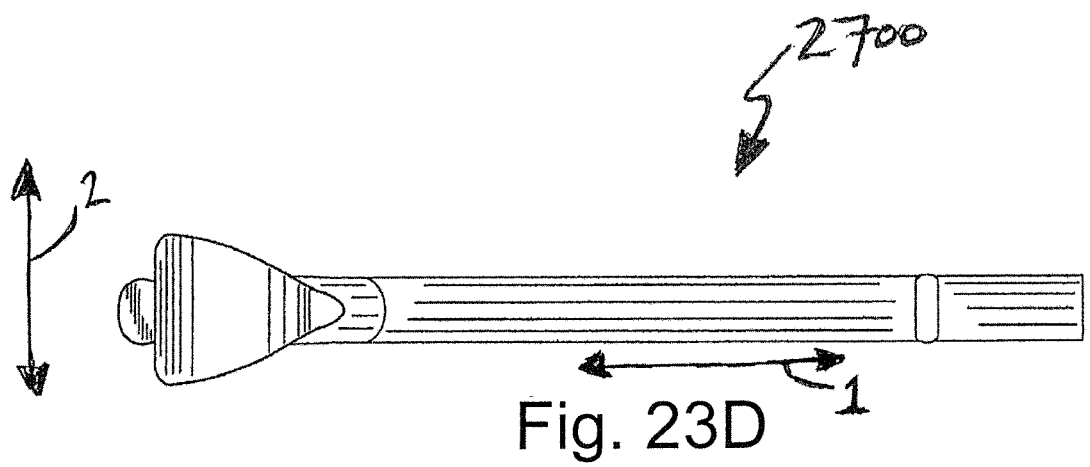

FIG. 23D is a bottom view of the dental tool of FIG. 23A.

Figures 23E, 23F:
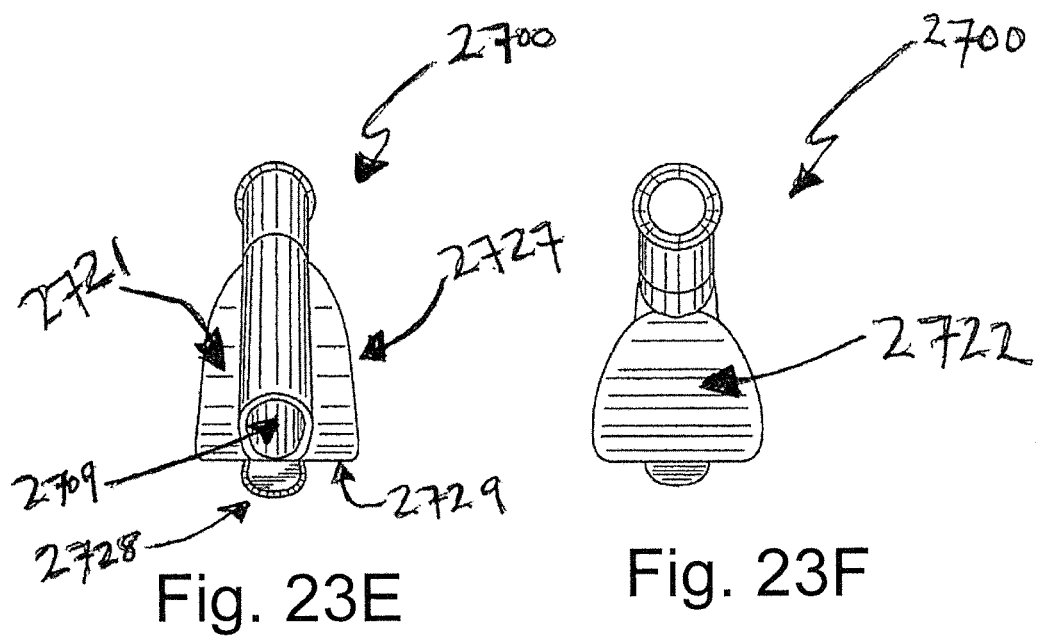

FIG. 23E is a front view of the dental tool shown in FIG. 23A.

FIG. 23F is a back view of the dental tool shown in FIG. 23A.

FIG. 24A is a perspective view of a twenty-fourth embodiment dental tool.

FIG. 24B is a top view of the dental tool of FIG. 24A.

FIG. 24C is a left side view of the dental tool of FIG. 24A.

Figure 24D:
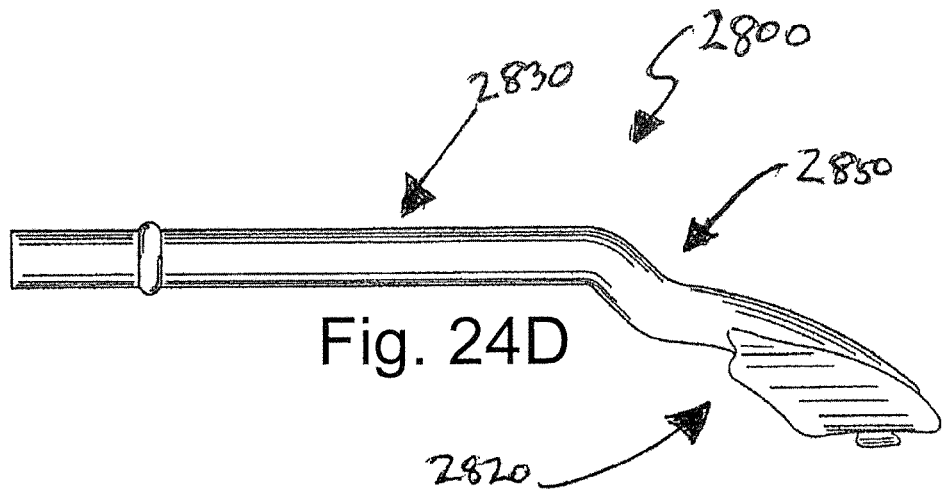

FIG. 24D is a right side view of the dental tool of FIG. 24A.

Figure 24E:
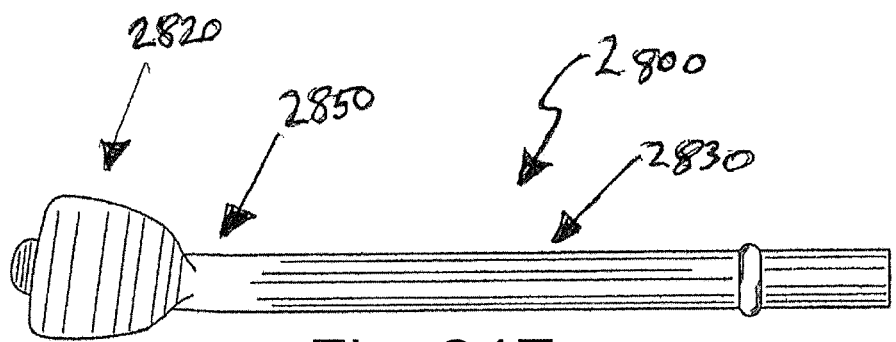

FIG. 24E is a bottom view of the dental tool of FIG. 24A.

Figures 24F, 24G:
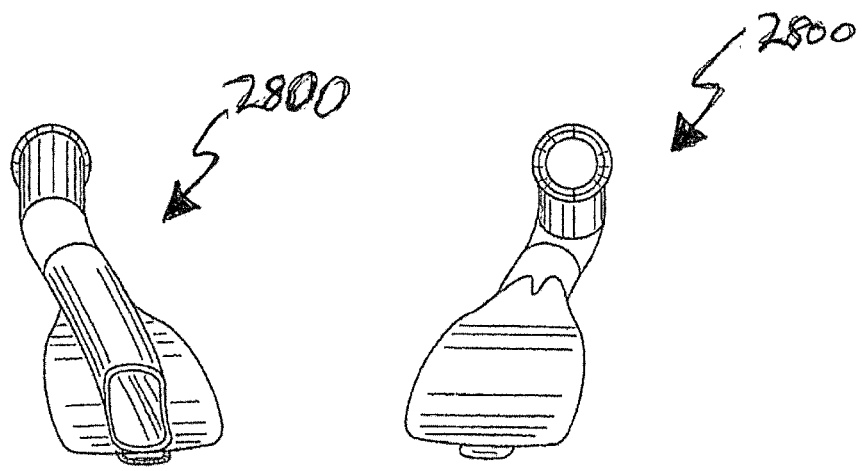

FIG. 24F is a front view of the dental tool shown in FIG. 24A.

FIG. 24G is a back view of the dental tool shown in FIG. 2$A.

Figure 25A:
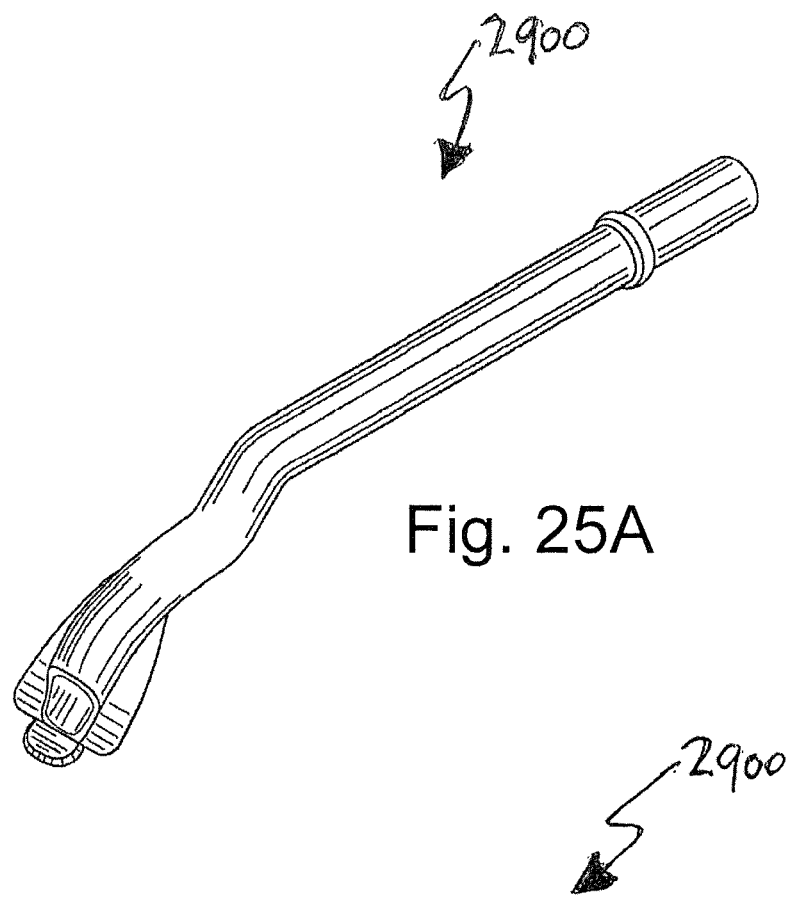

FIG. 25A is a perspective view of a twenty-fifth embodiment dental tool.

Figure 25B:
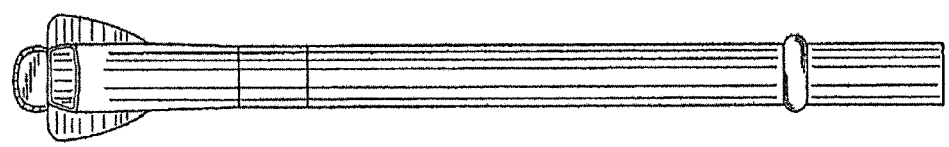

FIG. 25B is a top view of the dental tool of FIG. 25A.

Figure 25C:
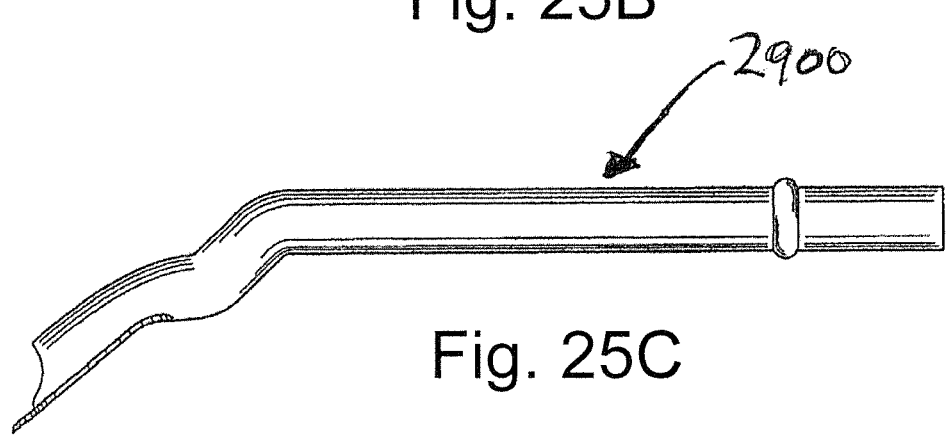

FIG. 25C is a side view of the dental tool of FIG. 25A.

Figure 25D:
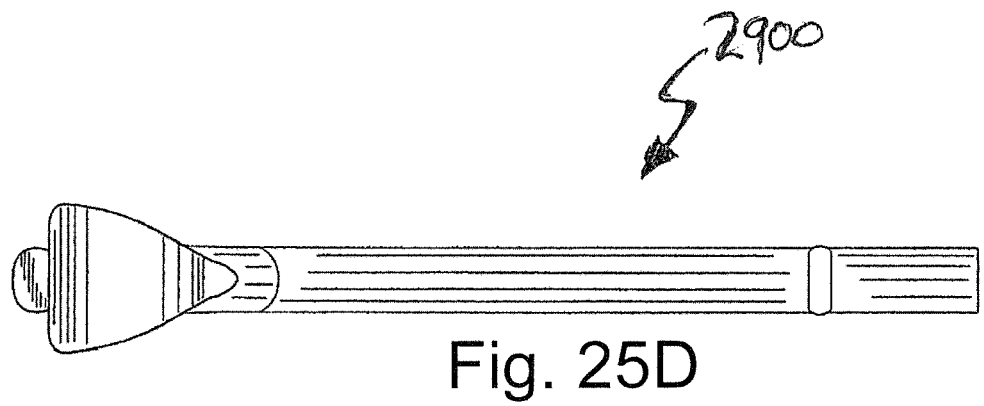

FIG. 25D is a bottom view of the dental tool of FIG. 25A.

Figures 25E, 25F:
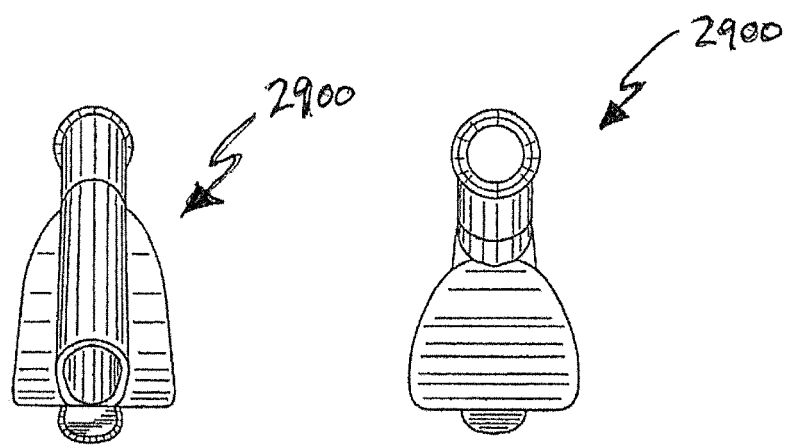

FIG. 25E is a front view of the dental tool shown in FIG. 25A.

FIG. 25F is a back view of the dental tool shown in FIG. 25A.

Figure 26A:
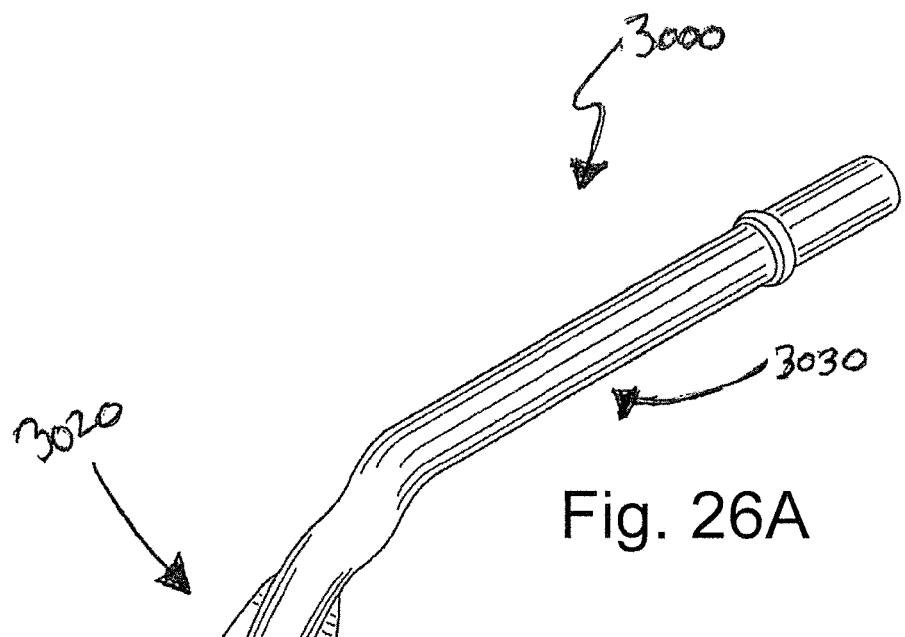

FIG. 26A is a perspective view of a twenty-sixth embodiment dental tool.

Figure 26B:
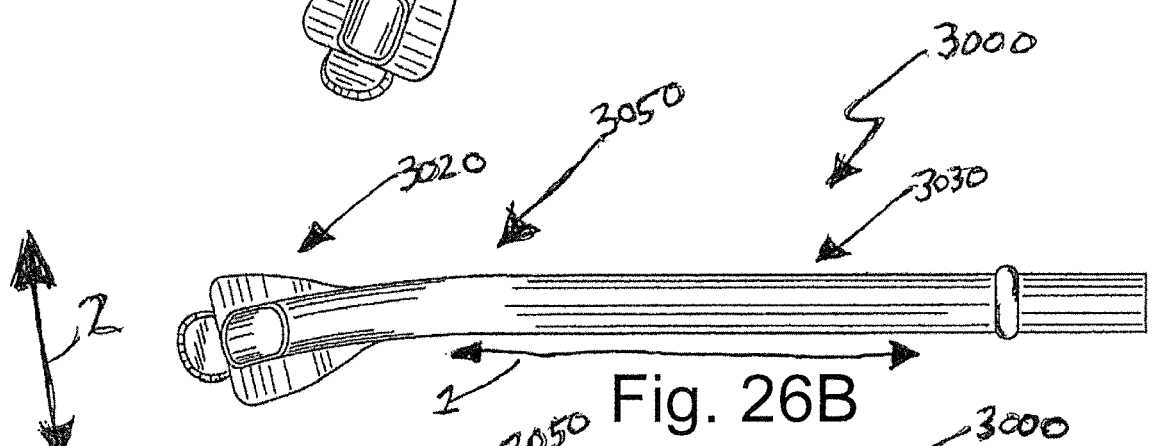

FIG. 26B is a top view of the dental tool of FIG. 26A.

Figure 26C:
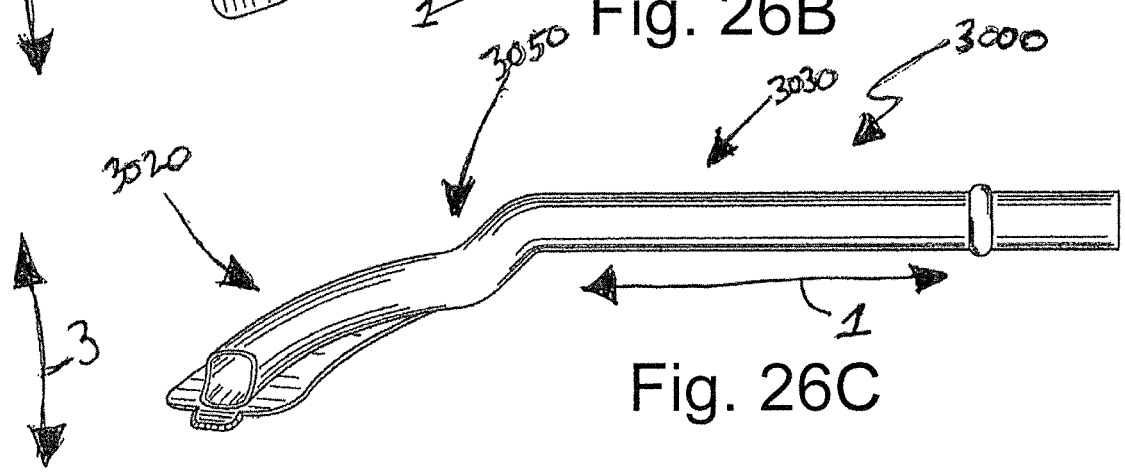

FIG. 26C is a left side view of the dental tool of FIG. 26A.

Figure 26D:
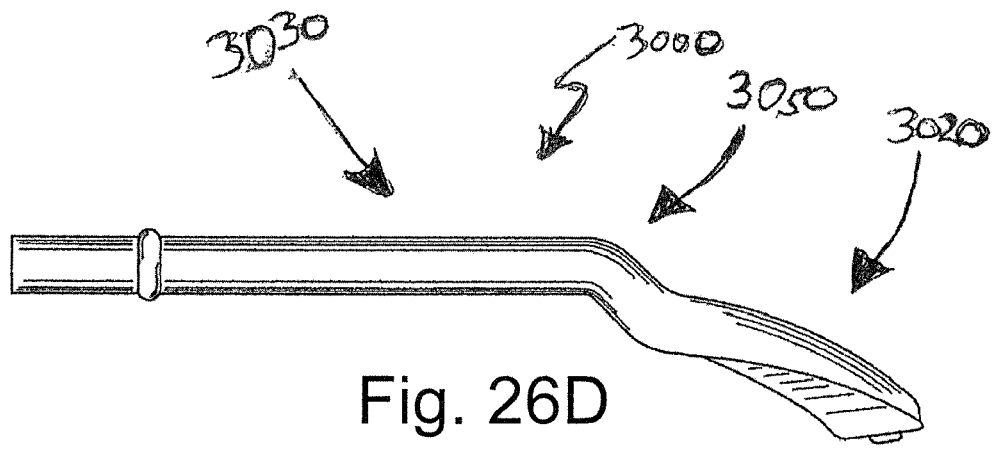

FIG. 26D is a right side view of the dental tool of FIG. 26A.

Figure 26E:
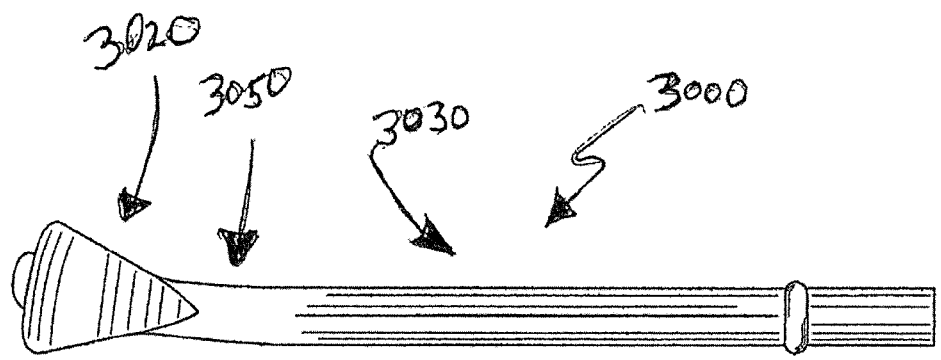

FIG. 26E is a bottom view of the dental tool of FIG. 26A.

Figures 26F, 26G:
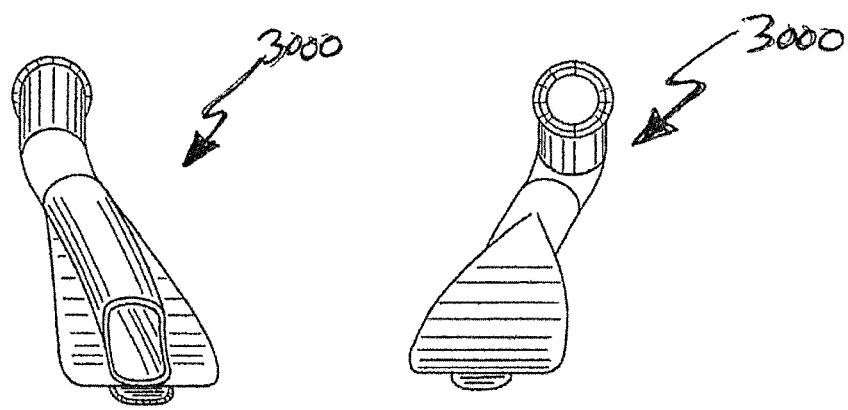

FIG. 26F is a front view of the dental tool shown in FIG. 26A.

FIG. 26G is a back view of the dental tool shown in FIG. 26A.

FIG. 27A is a perspective view of a twenty-seventh embodiment dental tool.

FIG. 27B is a top view of the dental tool of FIG. 27A.

FIG. 27C is a left side view of the dental tool of FIG. 27A.

Figure 27D:
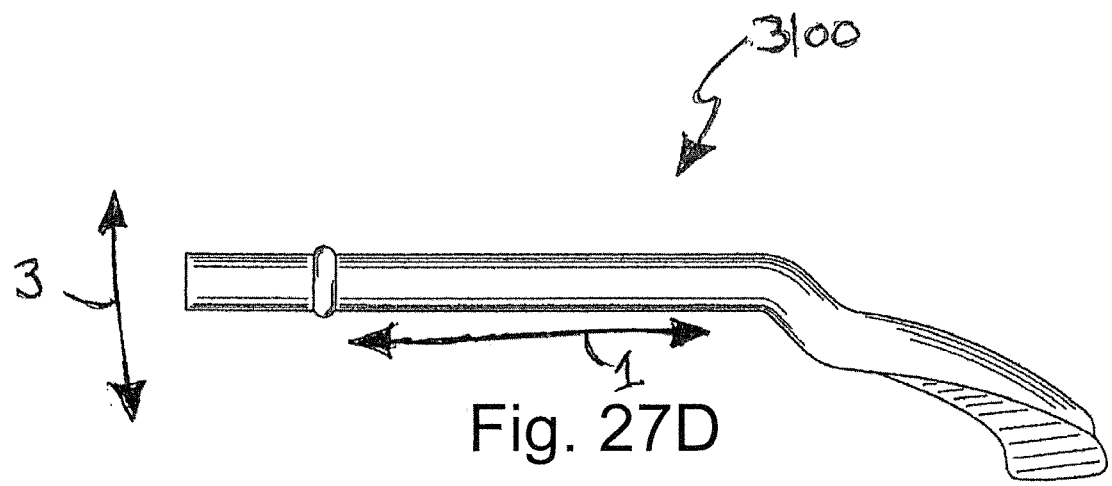

FIG. 27D is a right side view of the dental tool of FIG. 27A.

Figure 27E:
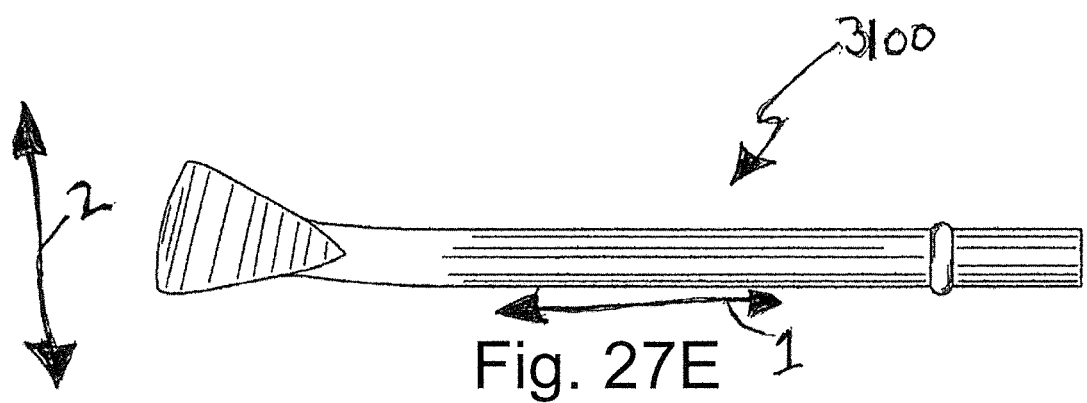

FIG. 27E is a bottom view of the dental tool of FIG. 27A.

FIG. 26F is a front view of the dental tool shown in FIG. 27A.

Figures 27F, 27G:
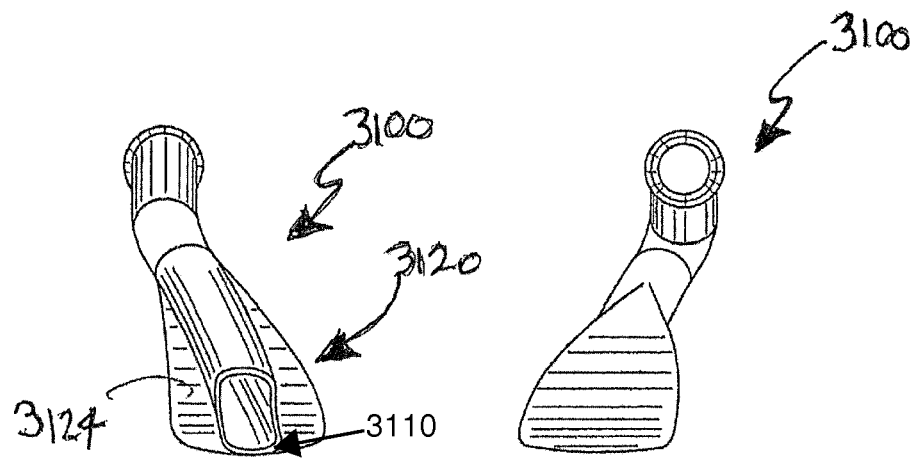

FIG. 27G is a back view of the dental tool shown in FIG. 27A.

Figure 28A:
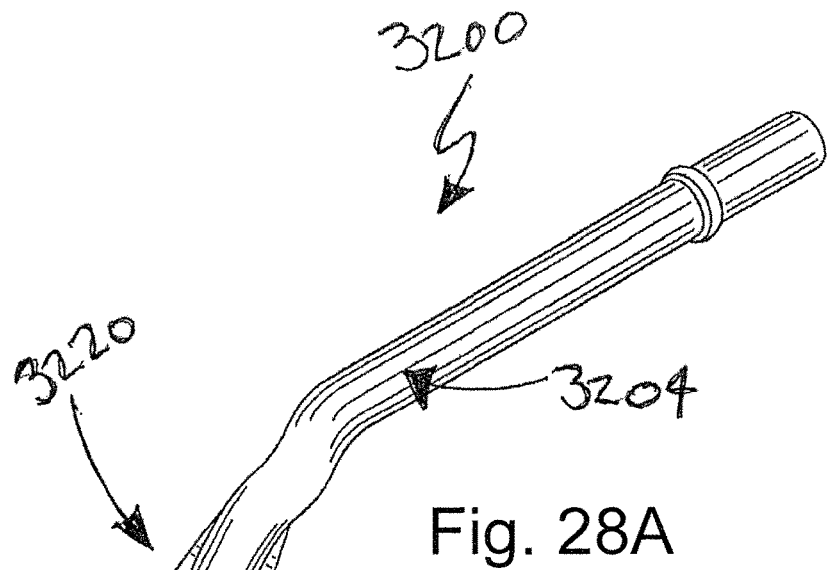

FIG. 28A is a perspective view of a twenty-eighth embodiment dental tool.

Figure 28B:
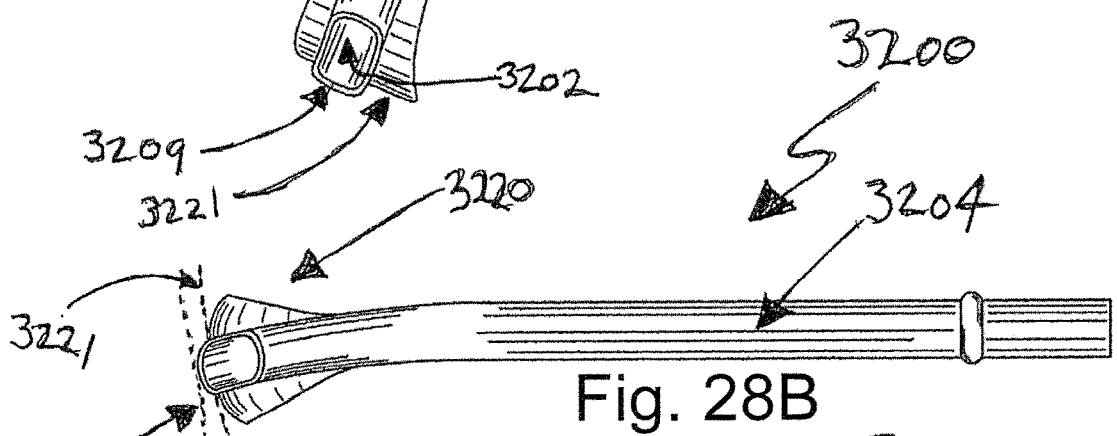

FIG. 28B is a top view of the dental tool of FIG. 28A.

Figure 28C:
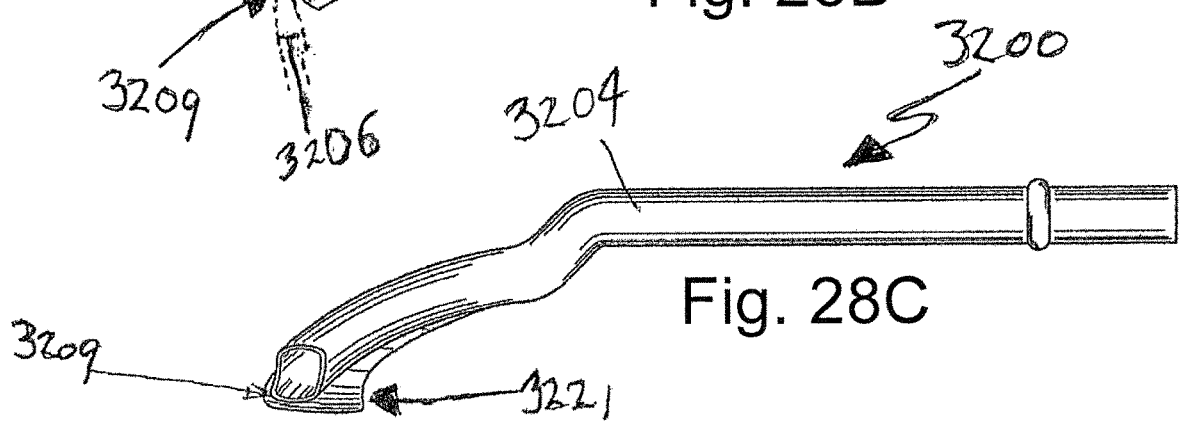

FIG. 28C is a left side view of the dental tool of FIG. 28A.

Figure 28D:
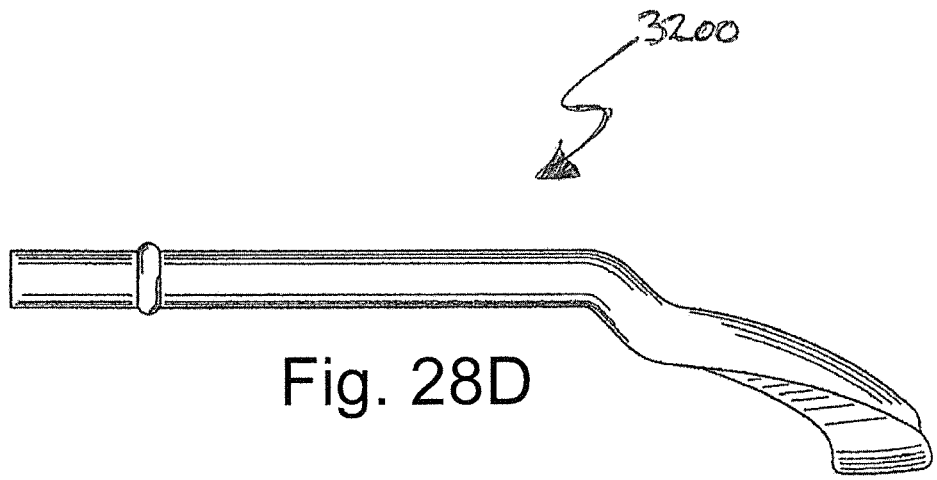

FIG. 28D is a right side view of the dental tool of FIG. 28A.

Figure 28E:
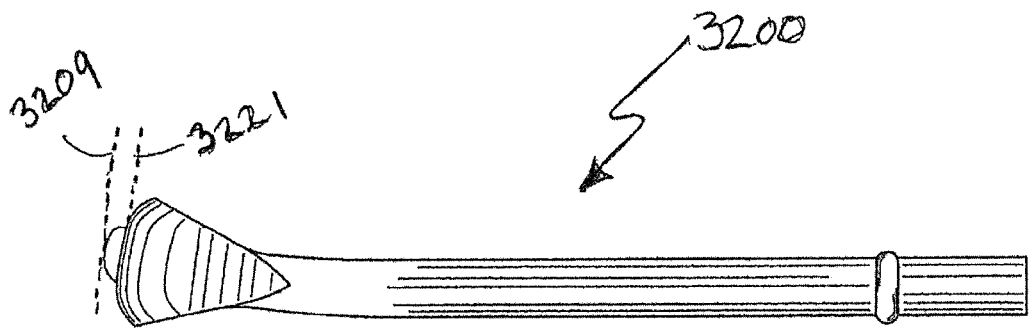

FIG. 28E is a bottom view of the dental tool of FIG. 28A.

Figures 28F, 28G:
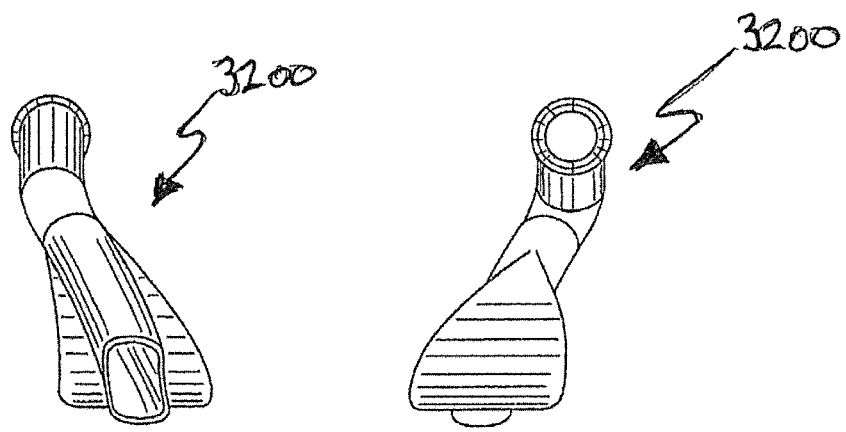

FIG. 28F is a front view of the dental tool shown in FIG. 28A.

FIG. 28G is a back view of the dental tool shown in FIG. 28A.

Figure 29A:
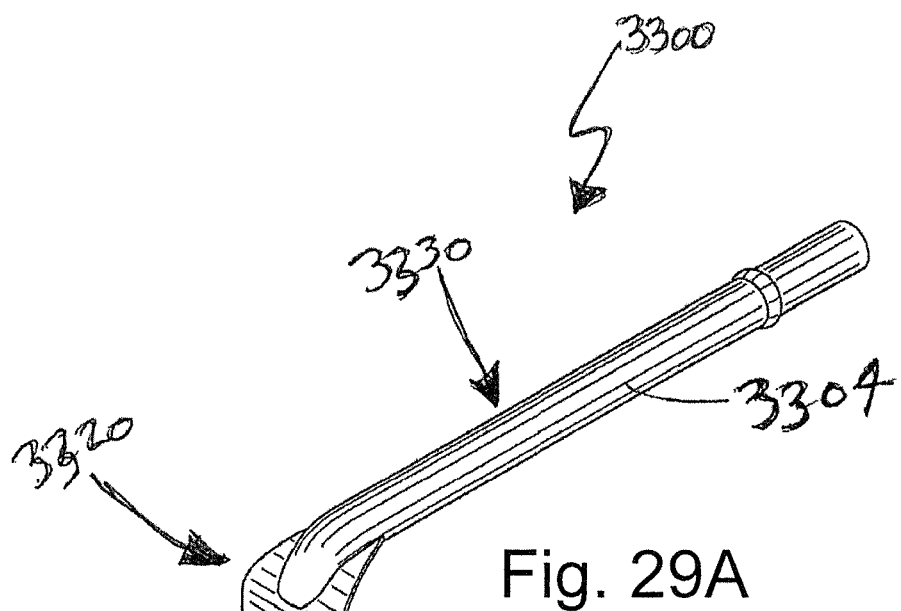

FIG. 29A is a perspective view of a twenty-ninth embodiment dental tool.

Figure 29B:
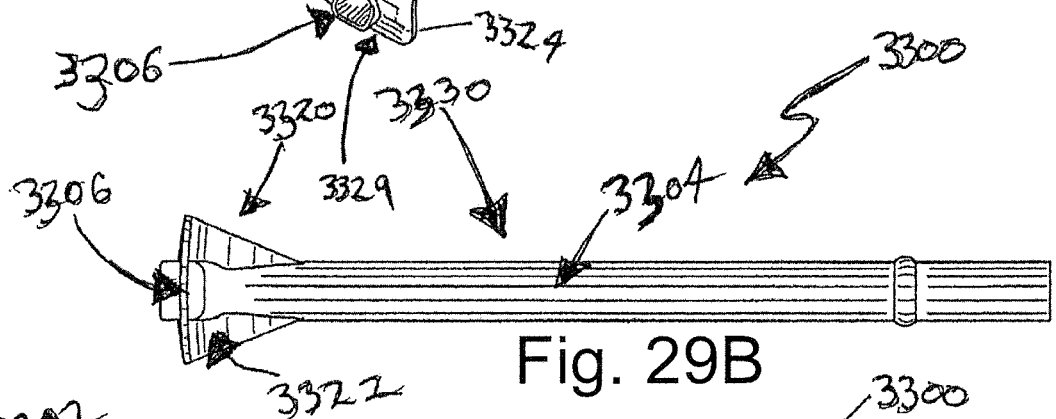

FIG. 29B is a bottom view of the dental tool of FIG. 29A.

Figure 29C:
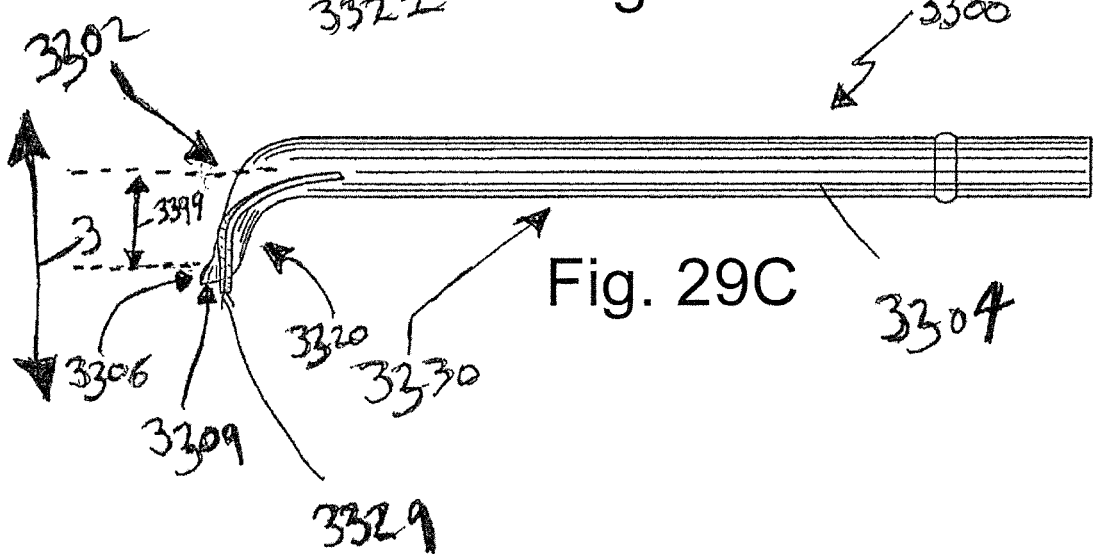

FIG. 29C is a side view of the dental tool of FIG. 29A.

Figure 29D:
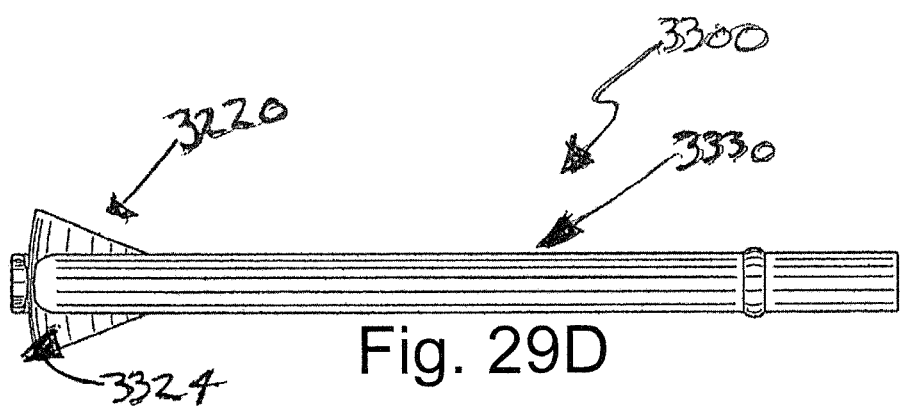

FIG. 29D is a top view of the dental tool of FIG. 29A.

Figures 29E, 29F:
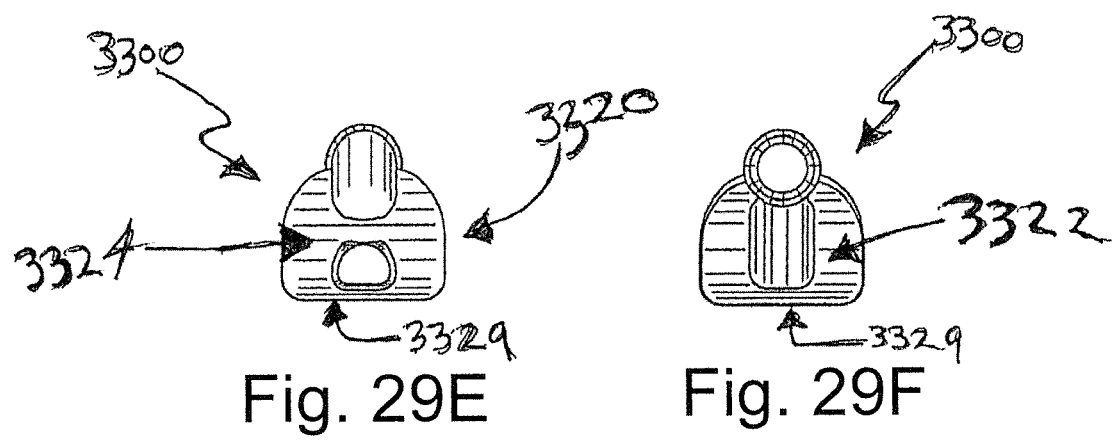

FIG. 29E is a front view of the dental tool shown in FIG. 29A.

FIG. 29F is a back view of the dental tool shown in FIG. 29A.

Figures 30A, 30B, 30C:
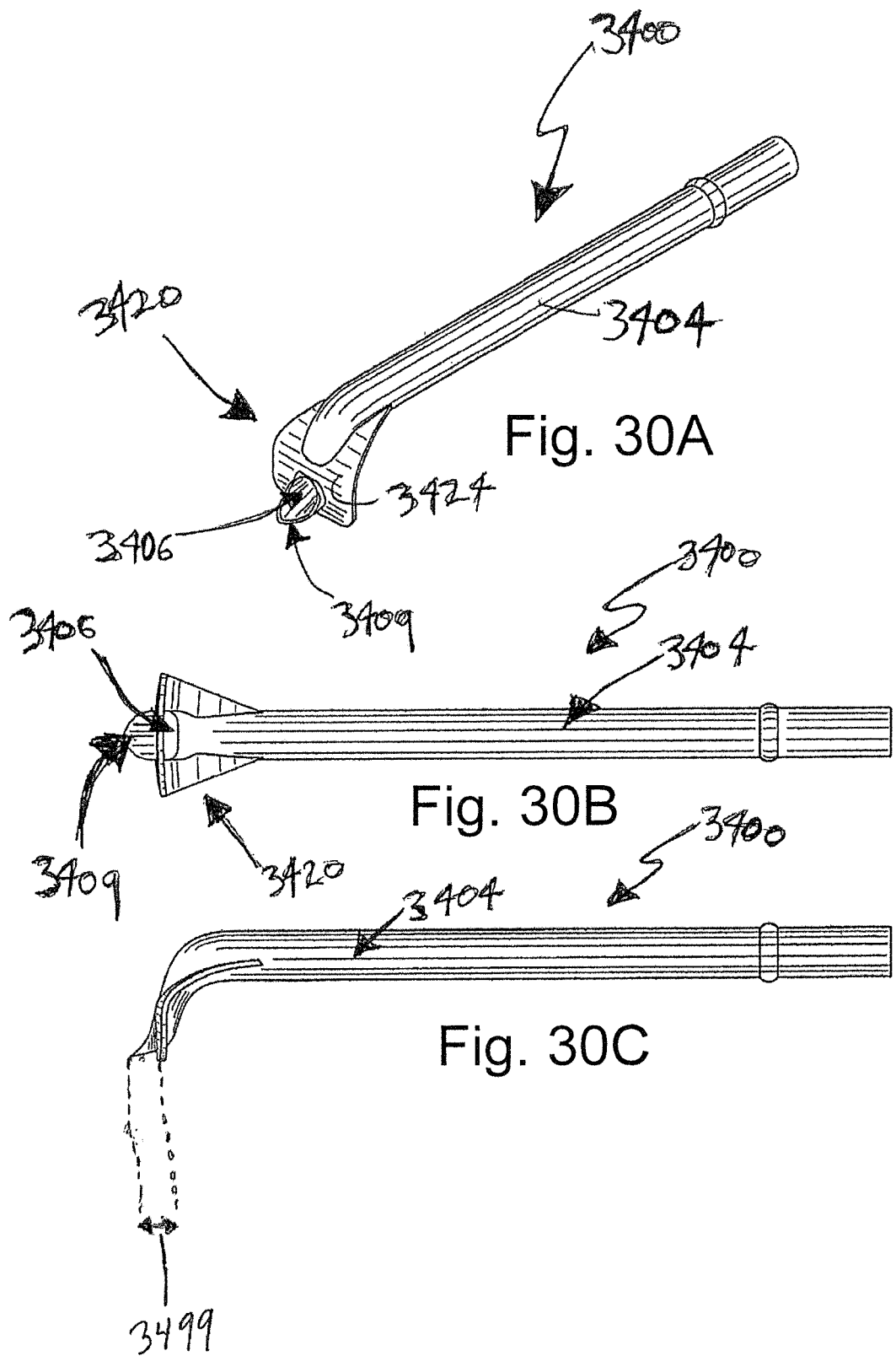

FIG. 30A is a perspective view of a thirtieth embodiment dental tool.

FIG. 30B is a bottom view of the dental tool of FIG. 30A.

FIG. 30C is a side view of the dental tool of FIG. 30A.

Figure 30D:
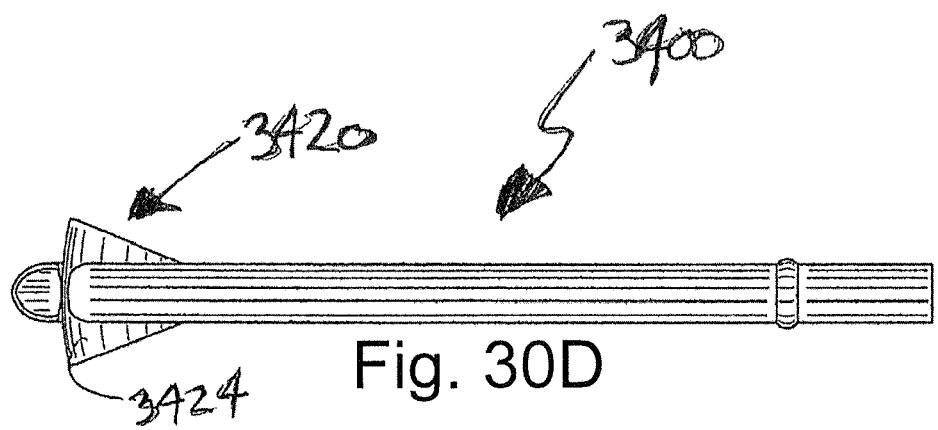

FIG. 30D is a top view of the dental tool of FIG. 30A.

Figures 30E, 30F:
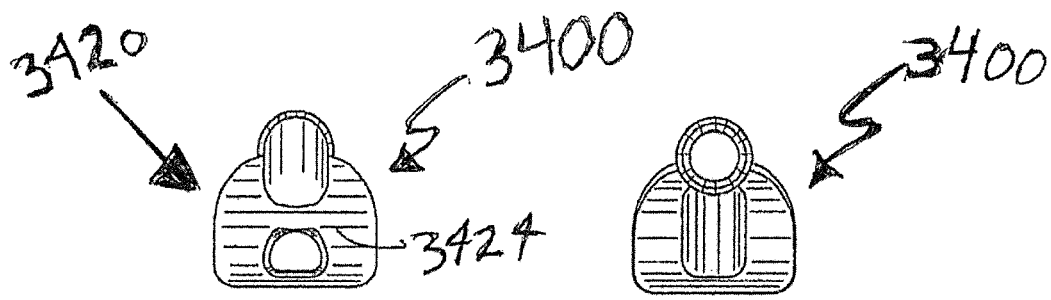

FIG. 30E is a front view of the dental tool shown in FIG. 30A.

FIG. 30F is a back view of the dental tool shown in FIG. 30A.

Figure 31A:
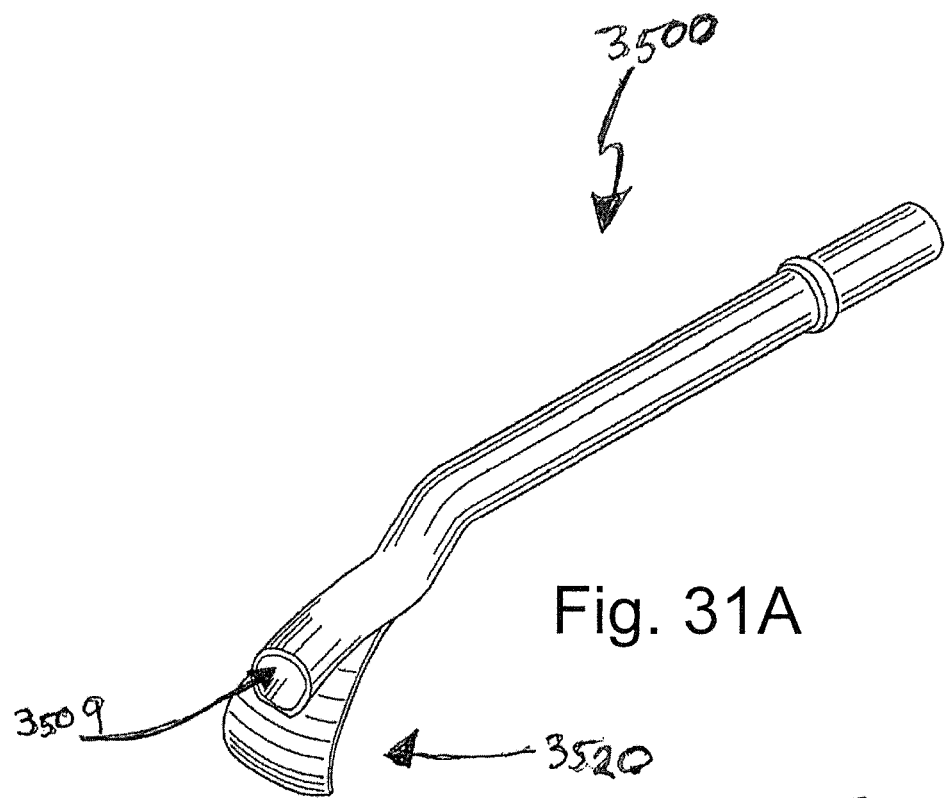

FIG. 31A is a perspective view of a thirty-first embodiment dental tool.

Figure 31B:
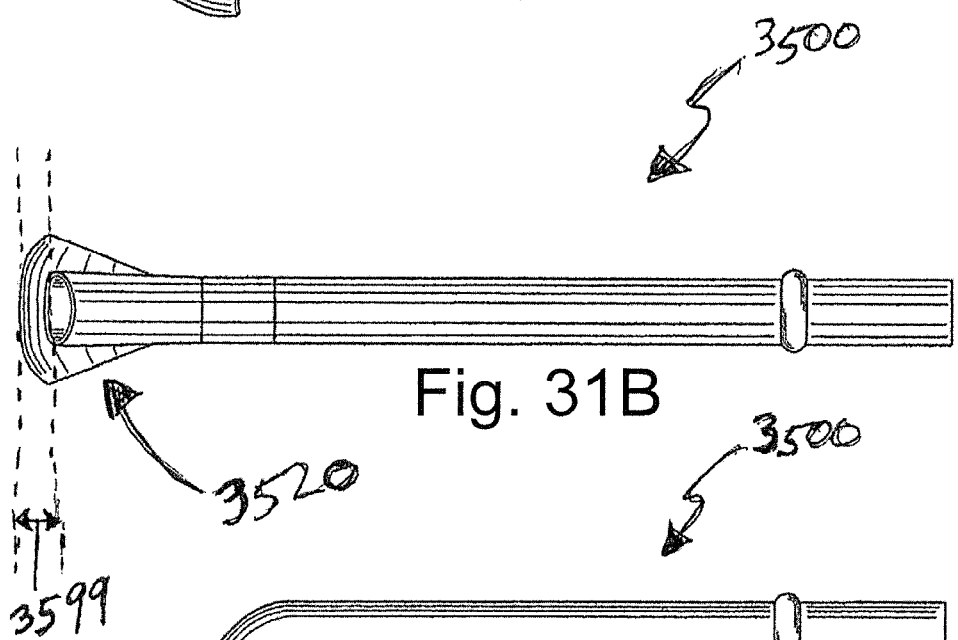

FIG. 31B is a top view of the dental tool of FIG. 31A.

Figure 31C:
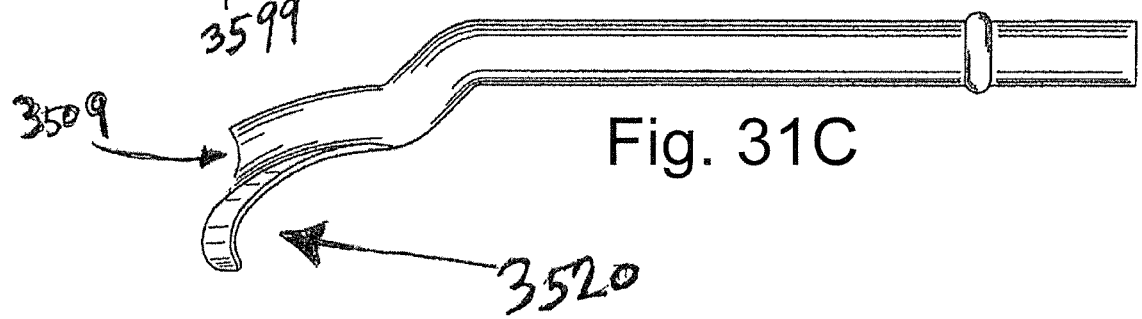

FIG. 31C is a side view of the dental tool of FIG. 31A.

Figure 31D:
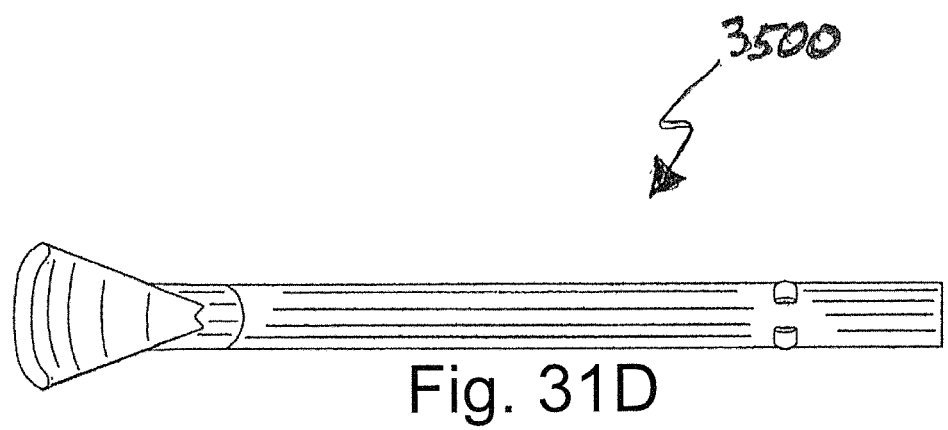

FIG. 31D is a bottom view of the dental tool of FIG. 31A.

Figures 31E, 31F:
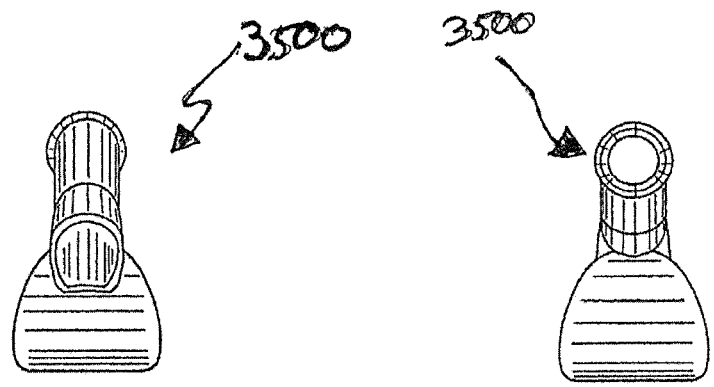

FIG. 31E is a front view of the dental tool shown in FIG. 31A.

FIG. 31F is a back view of the dental tool shown in FIG. 31A.

Figure 32A:
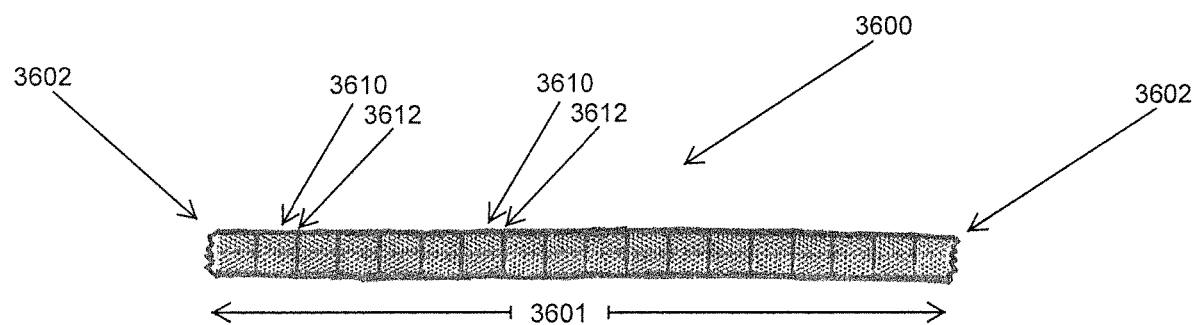
Figure 32B:
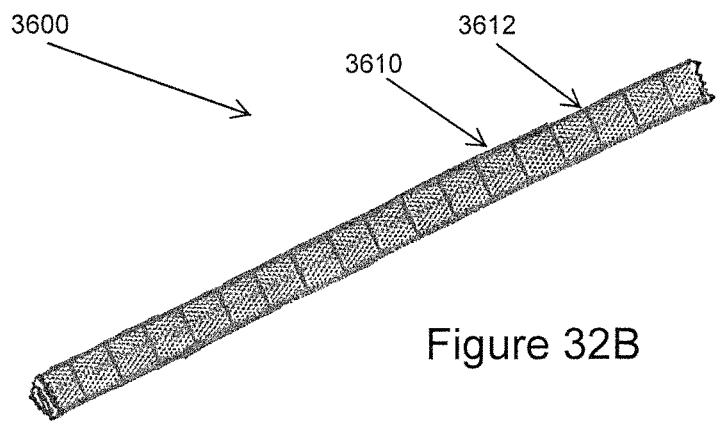
Figure 32C:
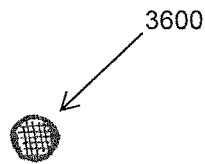

FIGS. 32A-32C are side, perspective and end views of an embodiment handle, respectively.

DETAILED DESCRIPTION OF THE PREFERRED EMBODIMENTS

Referring now to the drawings, FIGS. 1A-1F show an embodiment tool 100. The tool 100 has a generally longitudinal shape with a first, proximal end 101 and a second, distal end 102. The tool 100 may be formed of stainless steel, carbide, plastic or resin, or any other suitable material known in the art, and may include a first operational unit 110 disposed on the proximal end 101 and a second operational unit 120 disposed on the distal end 102. Further, the densities of the materials used may be varied as well, so as to provide heavier or lighter instruments as may be desirable for the end user. For example, denser grades of stainless steel may be used to create a relatively heavier product. The embodiment tool 100 may also be disposable. The tool 100 further includes a handle region 130, a first neck region 140 disposed between the first operational unit 110 and the handle region 130, and a second neck region 150 disposed between the second operational unit 120 and the handle region 130. The handle region 130 may be thick, narrow, round, flat or have various combinations thereof.

The tool 100 may be integrally formed as a unitary structure, or, more preferably, is formed by separate units that are releasably mechanically linked together. Any suitable mechanical connection as known in the art may be used to releasably connect the various components together to form the tool 100. For example, the first operational unit 110 and first neck region 140 may be integrally formed as a single unit that mechanically couples, such as by a threaded section on the distal end of first neck region 140, to the handle region 130; the handle region 130 may also be integrally formed as a single unit having a corresponding threaded section on its proximal end to accept the mating threaded section of the first neck region 140. Similarly, the distal end of handle region 130 may also have a threaded section to accept a corresponding mating threaded section on the proximal end of the second neck region 150, in which the second neck region 150 is integrally formed with the second operational unit 120. Many variations are contemplated and are within the scope of the present invention. For example, the handle region 130, first neck region 140 and first operational unit 110 may all be integrally formed as a single unit, which is threadedly or otherwise mechanically attached to the second neck region 150 and second operational unit 120, which portions 120, 150 may again be integrally formed as a single unit. For example, as illustrated in FIGS. 1E and 1F, the second neck region 150 and second operational unit 120 may be integrally formed as a single unit. A proximal end 151 of the second neck region 150 may include a threaded section 159, such as a threaded protrusion or a threaded aperture, to correspondingly mate with a threaded section on the distal end of the handle region 130.

The handle region 130 is used as a gripping region by the Dentist in the manipulation of the tool 100 and may be generally circular, hexagonal, octagonal, flat or the like in cross-section perpendicular to its length; the handle region 130 preferably has knurls 132 or other surface texturing to improve the Dentist's grip upon the handle region 130. Alternatively, the handle region 130 may include an exterior grip material made of plastic, rubber or any other suitable material. A particularly preferred embodiment handle region is discussed later, which may be employed in any of the embodiment tools discussed in the following. Portions of the tool 100 may be formed so as to be hollow or solid in construction. Additionally, it will be appreciated that the cross-sectional shape of the various portions 110, 140, 130, 150, 120 of the tool 100 may be in different shapes, and preferably may vary in a substantially continuous manner from the proximal end 101 to the distal end 102.

As shown in FIGS. 1B and 1C, the longitudinal length of the handle region 130 may define a longitudinal direction 1.

A lateral direction 2, corresponding to side-to-side motion of the ends 101, 102, is perpendicular to the longitudinal direction 1, while a transverse direction 3 is perpendicular to both the longitudinal direction 1 and the lateral direction 2, corresponding to up-and-down motion of the ends 101, 102. These directions (longitudinal, lateral and transverse) are used throughout the following to describe features of the various embodiments.

In the embodiment tool 100, the second operational unit 120 includes a concave tongue retractor 120. The concave tongue retractor 120 is used to retract the tongue away from the treatment area where the Dentist is working. The concave tongue retractor 120 is used to retract and/or isolate the tongue during a procedure. As can be appreciated from FIGS. 1A-1F, the concave tongue retractor 120 is preferably shaped to provide for a natural area to encapsulate a portion of the tongue, thereby removing it from the treatment area. In cross-section along the transverse plane (i.e., in the plane defined by directions 1 and 3 and best illustrated in FIG. 1B), the tongue retractor 120 has a circular, or more preferably a semi-circular, shape to provide a concave ventral surface 122 and a corresponding convex dorsal surface 124, in which the ventral surface 122 is the working surface that is designed to come into direct contact with the patient's tongue. The curve may extend through approximately 30 degrees to 160 degrees of arc, more preferably through about 70 degrees to 100 degrees of arc, more preferably still through about 80 to 90 degrees of arc. Preferably, as a semi-circular arc in cross-section within the transverse plane, the major axis of the tongue retractor 120 is more closely aligned along the transverse direction 3 (or along the distal extents of the retractor 120) while the minor axis is more closely aligned along the longitudinal direction 1 (or perpendicular to the distal extents—i.e., perpendicular to the bottom surface 122); the major axis of the tongue retractor may be, for example, at least 50% greater than its minor axis. Similarly, the tongue refractor 120 also has a curved shape, preferably circular, in cross-section along the lateral plane (i.e., the plane defined by directions 1 and 2 and best illustrated in FIG. 1C), which further increases the concave nature of ventral surface 122 and the convex nature of dorsal surface 124. The tongue retractor 120 preferable extends through 5 to 90 degrees of arc, more preferably still through 10 to 45 degrees of arc, more preferably still through about 20 to 30 degrees of arc, in the cross-section of the lateral plane. The distal end 102 of the tongue retractor 120 may have extents along the lateral direction 2 from about 10 mm to 40 mm, and preferably of about 25 mm, providing a curved length along the lateral direction 2 that is slightly greater than this depending upon the desired amount of curvature. The tongue retractor 120 may have extents along the longitudinal direction 1 from about 19 mm to about 51 mm, and preferably about 32 mm, which may similarly provide for a slightly greater curved length. The lateral extents 2 of the distal end 102 may range from about 15 mm to about 40, more preferably about 26 mm.

For purposes of the following, a dorsal direction is a direction along the transverse direction 3 towards which the dorsal surface 124 faces (i.e., an "upward" direction), whereas a ventral direction is the direction along the transverse direction 3 that is opposite to the dorsal direction—i.e., in the direction which the ventral surface 122 faces, the "downward" direction. In this embodiment 100, the first neck region 140 may be straight and thus extend along and parallel to the longitudinal direction 1. In contrast, the second neck region 150 is straight in the lateral plane (the plane defined by longitudinal direction 1 and lateral direction 2), as shown in FIG. 1C, but is bent in the transverse plane (the plane defined by longitudinal direction 1 and transverse direction 3), as shown in FIG. 1B. The second neck region 150 includes a first angle or bend 152 that angles ventrally in the transverse direction 3, and then a more distal second angle or bend 154 that angles dorsally in the transverse direction 3. The angles of the bends 152, 154 may be substantially equal so that the distal end of the second neck 150 terminates in a direction that is substantially parallel to the distal end of handle region 130 but merely offset ventrally by a transverse distance. Or, more preferably, the distal upward bend 154 may be less than the initial proximal bend 152 so that the distal end 102 of the second neck region 150 points slightly ventrally in the transverse direction with respect to the distal end 102 of the handle region 130.

The ventral, transverse offset is advantageously designed to more easily navigate the anatomy of the patient to reach the working area; more particularly, the second operational unit 120 is disposed ventrally towards the patient with respect to the handle region 130, which makes it easier to navigate around the anatomy of the patient when approaching, for example, from the contralateral side. This ventral offset provides the unexpected benefit of reducing strain upon the Dentist when retracting tissue or anatomy, such as a patient's tongue. In particular, this ventral offset, and optional ventral angle, of the second operation unit 120 permits the second operational unit 120 to be more easily manipulated with handle region 130, as second neck region 150 more conveniently clears the teeth and jaw of the patient. In preferred embodiments the ventral distance between the proximal end 151 of the second neck region 150 and the distal end 158 of the second neck region 150 in the transverse direction 3 is from about 5 mm to 32 mm, more preferably from 10 mm to 26 mm, more preferably still from about 15 mm to 20 mm. The combination of the first bend 152 and the second bend 154 gives the second neck region 150 a generally S-shaped or stepped appearance, and for purposes of this disclosure are termed "S-shaped" bends. The first bend 152 may pass through from 10 to 90 degrees of arc, more preferably through from 30 to 60 degrees of arc, more preferably still through about 45 degrees of arc, and extend in a related direction for from 7 to 30 mm, more preferably from 10 to 20 mm, more preferably still from 13 to 17 mm. The second bend 154 may pass through from 5 to 90 degrees of arc, more preferably through from 15 to 60 degrees of arc, more preferably still through about 30 degrees of arc, and extend in a related direction of from 7 to 30 mm, more preferably from 10 to 20 mm, more preferably still from 13 to 17 mm. The second bend 154 provides a surface onto which the second operational unit 120 is mounted. For example, the dorsal surface 124 of second operational unit 120 may be bonded to a ventral surface of the second bend 154. Or, the second operational unit 120 may be embedded within the second bend 154, so that portions of the second bend 154 extend over both the ventral surface 122 and the dorsal surface 124 of the operational unit 120.

The S-shaped neck region 150 creates a ventral, transverse spatial displacement of the operational unit 120, and optionally a ventral, transverse angular displacement of the operational unit 120 as well. For example, the lateral plane of the operational unit 120 (which may be defined, for example, by the lateral and longitudinal extents of the operational unit 120) may be angled in a ventral, transverse direction 3 with respect to the lateral plane of the tool 100 (which may be defined, for example, by the longitudinal direction 1 and the lateral direction 2). These transverse displacements, both angular and spatial, help to position the tool with respect to the location of the mandible, which is typically inferior to the position of the Dentist, and consequently provide a more ergonomic design that requires less force and thus results in less fatigue for the Dentist, and also help the handle region 130 to more easily clear the teeth and mandible of the patient. In preferred embodiments, the ventral, transverse angular displacement of the operational unit 120 is from 0 degrees to 90 degrees with respect to the longitudinal axis 1 of the handle region 130, more preferably from 15 degrees to 60 degrees, more preferably still from 20 degrees to 30 degrees. It should be appreciated that in some alternative embodiments, the neck region may be smoothly bent across its length to provide the desired curvature and spatial displacements, rather than providing for a discrete number of individual bends as shown in the discussed preferred embodiments; such smoothly bend configurations are also considered "S-shaped bends" for purposes of the following disclosure. In such embodiments, it will be appreciated that they still include substantially first and second bends with corresponding angular and spatial extents as discussed above.

The embodiment tool 100 provides improved ergonomics through the use of S-shaped bends 152, 154. These ergonomic features can be optionally incorporated into each of the other tools and embodiments discussed herein. The ventral, S-shape of the second neck region 150 allows the tool 100, and in particular the tongue retractor 120, to align more optimally within the oral cavity, such that a greatly reduced amount of force is needed in the transverse direction 3. More specifically, the ventral orientation provided by the S-shaped region 150 in effect provides the ventral (i.e., downward) motion typically needed to retract a tongue, and as a result greatly reduces the effort required by a Dentist to perform such tongue retraction. This dramatically decreases the Dentist's fatigue and discomfort, and avoids prolonged strain on the neck, shoulder, arm, back, and hand, thus reducing the risk of injury to the Dentist.

The first operational unit 110 may optionally be present, or the proximal end 101 of the handle region 130 may terminate in a suitable shape or with a suitable fitting. By way of example, however, the first operational unit 110 may be, for example, screwed onto the proximal end 101 of the handle region 130 to provide additional functionality to the tool 100. For example, the first operational unit 110 may be a periosteal elevator 123. Furthermore, as can be appreciated by those skilled in the art, the proximal end of the handle 120 may instead include a dental probe, a dental hook, or other useful apparatus. In other embodiments, the entire tool may be integrally formed so that the handle region, neck region and operational unit are all formed together as a single unit.

In the following, various embodiment tools are discussed. It will be appreciated that features from the embodiment tool 100, or indeed from any other embodiment tool discussed herein, may be used within the other respective embodiments discussed. Specifically, the S-shaped neck region 150, with its related angular and spatial parameters, may be successfully employed. For the sake of brevity, only specific features of a particular embodiment that have not been previously introduced are discussed in that embodiment, and it will be appreciated that it may be possible to then incorporate such features into other embodiments, such as specific angular offsets or spatial extents.

FIGS. 2A-2F illustrate another embodiment tool 200 having an S-shaped second neck region 250 coupling a second embodiment tongue retractor 220 to a handle region 230. Compared to the first embodiment tongue retractor 120, the embodiment tongue retractor 220 has increased extents along the lateral direction 2—i.e., is wider. This may accommodate, for example, a patient with a larger mouth or tongue, and thus provide tools tailored to the specific anatomy of the patient. In preferred embodiments the tongue retractor 220 extends along the lateral direction 2 by about 15 mm to 45 mm, more preferably from 20 mm to 35 mm, more preferably still about 28 mm. The tongue retractor 220 may extend through 15 to 180 degrees of arc along the lateral direction 2, more preferably from 30 to 100 degrees of arc, more preferably still from 40 to 60 degrees of arc.

Figure 3D:
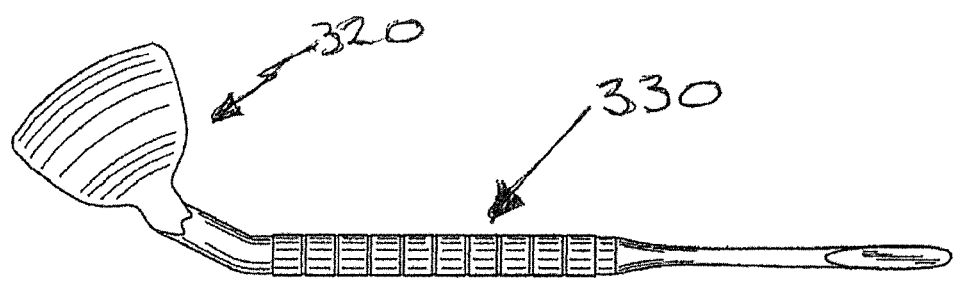
FIG. 3D is a bottom view of the dental tool of FIG. 3A.
Figure 3E:
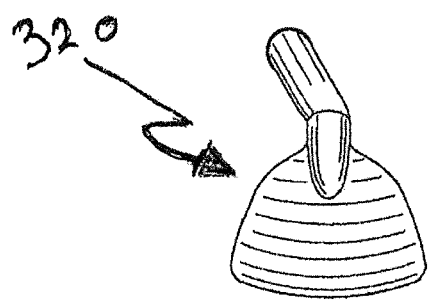
FIG. 3E is a top detailed view of a tongue retractor portion of the dental tool shown in FIG. 3A.
Figure 3F:
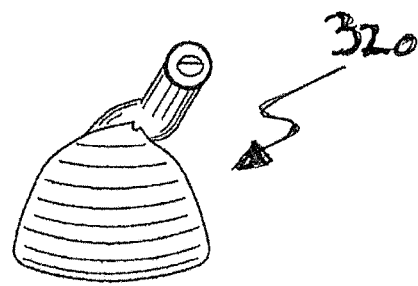
FIG. 3F is a bottom detailed view of a tongue refractor portion of the dental tool shown in FIG. 3A.
Figure 5D:
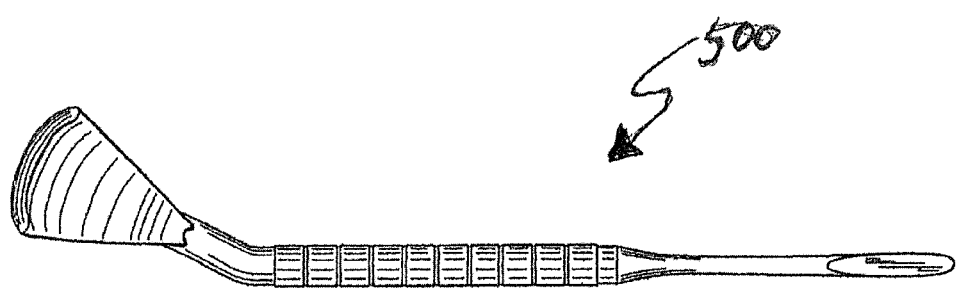
FIG. 5D is a bottom view of the dental tool of FIG. 5A.
Figure 5E:
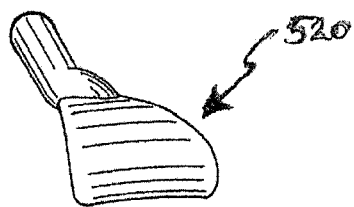
FIG. 5E is a top detailed view of a tongue retractor portion of the dental tool shown in FIG. 5A.
Figure 5F:
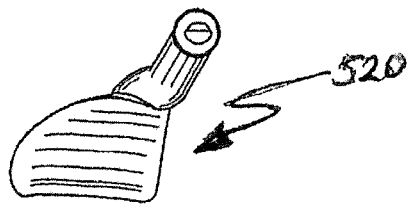
FIG. 5F is a bottom detailed view of a tongue refractor portion of the dental tool shown in FIG. 5A.

FIGS. 3A-3F illustrate another embodiment tool 300 having an S-shaped second neck region 350 coupling an operational unit 320, such as a tongue retractor 320 similar to the tongue retractor 120, to a handle region 330. In this embodiment the S-shaped second neck region 350 is bent both in the transverse plane (i.e., the plane as defined by longitudinal direction 1 and the transverse direction 3, best shown in FIG. 3B), and is also bent within the lateral plane (i.e., the plane as defined by longitudinal direction 1 and the lateral direction 2, best shown in FIG. 3C). Such lateral bending or offsets may accommodate the curvature of the mandible, which can be significant when working on the left or right side of the mandible, by using a correspondingly curved tool. Hence, it will be appreciated that tools herein may be provided that have predetermined bends to the right or left in the lateral direction 2 as needed based upon the intended working location in the mandible. The neck region 350 may include a first bend 352 and a second bend 354 (or a smoothly curved structure which functionally approximates such bends), and at least one of the bends 352 or 354 makes an angular offset in the lateral direction 2 so that the centerline of the operational unit 320 is laterally offset, both spatially and angularly, from the centerline of the handle region 330. In preferred embodiments, the second bend 354 (i.e., most distal bend) provides all of the lateral angling of the operational unit of the tool. The ventral, transverse displacement 3, both spatially and angularly, of the distal end 358 of the neck 350 with respect to the proximal end 351 of the neck 350 may be, for example, as discussed above with reference to the embodiments 100, 200. In addition, however, the distal end 358 of the neck 350 will have also gone through a lateral displacement 2. The spatial lateral displacement 2 of the distal end 358 of the neck 350 with respect to the proximal end 351 of the neck 350 may be, for example, from 5 mm to 30 mm, more preferably from 10 mm to 20 mm, more preferably about 15 mm, providing a corresponding spatial lateral displacement of the operational unit 320 with respect to the handle region 330. The angular lateral displacement of the distal end 358 of the neck 350 with respect to the proximal end 351 of the neck 350 (and thus the longitudinal direction 1 and the handle region 330) may be, for example, from 0 to 90 degrees, more preferably from 20 to 40 degrees, more preferably about 22 or 33 degrees, providing a corresponding angular lateral displacement of the operational unit 320 with respect to the handle region 330. Although in preferred embodiments the most distal bend 354 provides the total angular lateral displacement of the operational unit 320, in other embodiments each bend 352, 354 may provide part of the total angular lateral displacement of the operational unit 320. In such designs the neck region 350 is S-shaped in the transverse plane (as shown in FIG. 3B) but is C-shaped (if both bends 352, 354 have lateral angular displacements) or L-shaped (if only one bend 352, 354 has a lateral angular displacement) in the lateral plane (as shown in FIG. 3C). Such C-shaped or L-shaped curvatures may be considered "concave curvatures" for purposes of this disclosure. Other designs are certainly possible, however, such as designs in which one bend 352 or 354 increases the lateral angular displacement while another bend 354 or 352 reduces the lateral angular displacement, so that the neck 350 is S-shaped in both the transverse and lateral planes.

The embodiment neck design 350 allows the Dentist to utilize the tool 300 in a dramatically less awkward fashion, in particular allowing the Dentist to navigate the tool 300 on one particular side of the mandible. Furthermore, this neck design 350 allows a Dentist to reduce or eliminate the need for twisting or turning of the torso, upper extremities (e.g., the arm and hand), and head and neck in an effort to use the tool 300.

FIGS. 4A-4F illustrate another embodiment tool 400, having an embodiment tongue retractor 420 coupled via a neck region 450 to a handle region 430. The neck region 450 may be, for example, S-shaped in the transverse plane (defined by arrows 1 and 3) but straight in the lateral plane (defined by arrows 1 and 2). The embodiment tongue retractor 420 is similar to the embodiment tongue retractor 120 in terms of spatial extents but further includes an exaggerated concavity towards its distal lip 402. In particular, when viewed in the transverse plane, as in FIG. 4B, the tongue retractor 420 has a curved shape in which the majority of the curvature occurs in the most distal third of the retractor 420, thereby forming a more pronounced concavity for the ventral surface 422 that terminates in lip 402, in which lip 402 is angled from 45 to 170 degrees with respect to the lateral plane, more preferably from 85 to 150 degrees, and more preferably still at about 110 to 130 degrees with respect to the lateral plane, so that, in effect, the tongue retractor 420 curves back upon itself.

FIGS. 5A-5F illustrate another embodiment tool 500, having a tongue retractor 520 similar to the tongue retractor 420 that is coupled via a neck region 550 to a handle region 530. In the embodiment tool 500 the neck region 550 is S-shaped in the transverse plane (defined by arrows 1 and 3) and is L-shaped in the lateral plane (defined by arrows 1 and 2). Hence, the tongue retractor 520 is laterally offset from the handle region 530, both spatially and angularly, such as by about 20 to 45 degrees, more preferably between 22 and 33 degrees, with 22 and 33 degrees being respectively particularly preferred. It will be appreciated that the tool 500 could have lateral bends in directions opposite to those shown herein as, for example, based upon the intended use around the mandible, such as to the right or to the left.

FIGS. 6A-6F illustrate another embodiment tool 600, having an embodiment tongue retractor 620. The embodiment tongue retractor 620 has a substantially straight planar end 627 that creates a surface that is approximately perpendicular to the lateral plane defined by the longitudinal direction 1 and the lateral direction 2. The planar end 627 may be about 15 mm to 45 mm wide in the lateral direction 2, preferably about 25 mm wide, and about 5 mm to 30 mm long in the transverse direction 3, preferably about 15 mm long. A central bend 625 provides the majority of the transverse curvature, thereby forming a predominantly L-shaped cross-section for the tongue retractor 620 in the lateral plane, as best shown in FIG. 6B. In other embodiments the tongue retractor 620 may cover larger spatial extents—i.e., a larger sized tongue retractor. In such embodiments the planar end may be about 35 mm wide in the lateral direction 2, and about 25 mm long in the transverse direction 3.

Figure 7D:
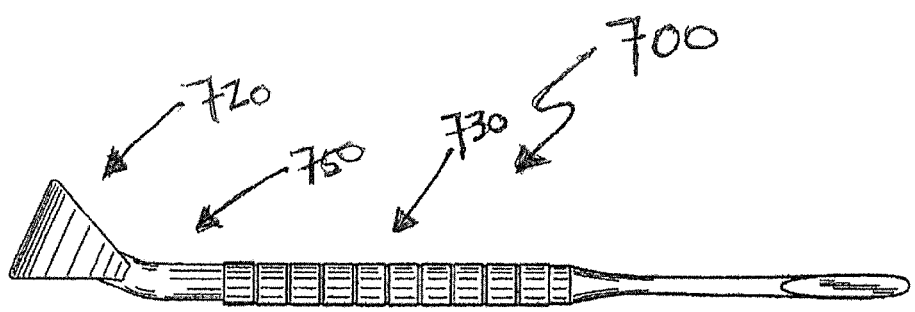
FIG. 7D is a bottom view of the dental tool of FIG. 7A.
Figure 7E:
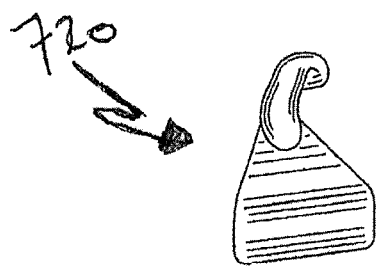
FIG. 7E is a top detailed view of a tongue retractor portion of the dental tool shown in FIG. 7A.
Figure 7F:
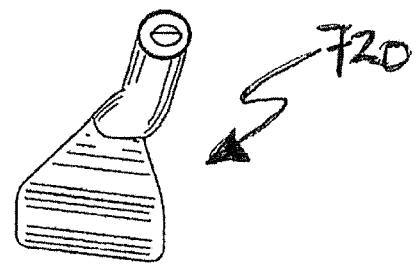
FIG. 7F is a bottom detailed view of a tongue refractor portion of the dental tool shown in FIG. 7A.

FIGS. 7A-7F illustrate another embodiment tool 700, having a tongue retractor 720 similar to the embodiment tongue retractor 620, which is coupled to the handle region 730 by way of a neck region 750 that is S-shaped in the transverse plane (defined by the longitudinal direction 1 and the transverse direction 3, as shown in FIG. 7B), and C-shaped in the lateral plane (defined by the longitudinal direction 1 and the lateral direction 2, as shown in FIG. 7C). The lateral angular and spatial offsets may be similar to those discussed in relation to earlier embodiments, with 22 and 33 degrees being particularly preferred for the lateral angular offset as they align nicely with the anatomy of the mandible, although any angles between 0 and 180 degrees are also contemplated.

Figure 8A:
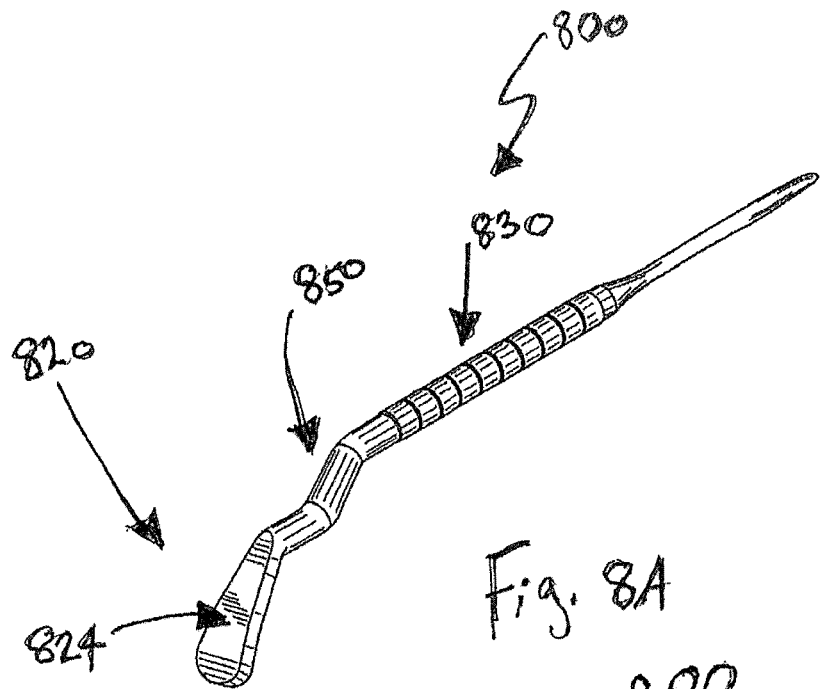
FIG. 8A is a perspective view of an eighth embodiment dental tool.
Figure 8B:
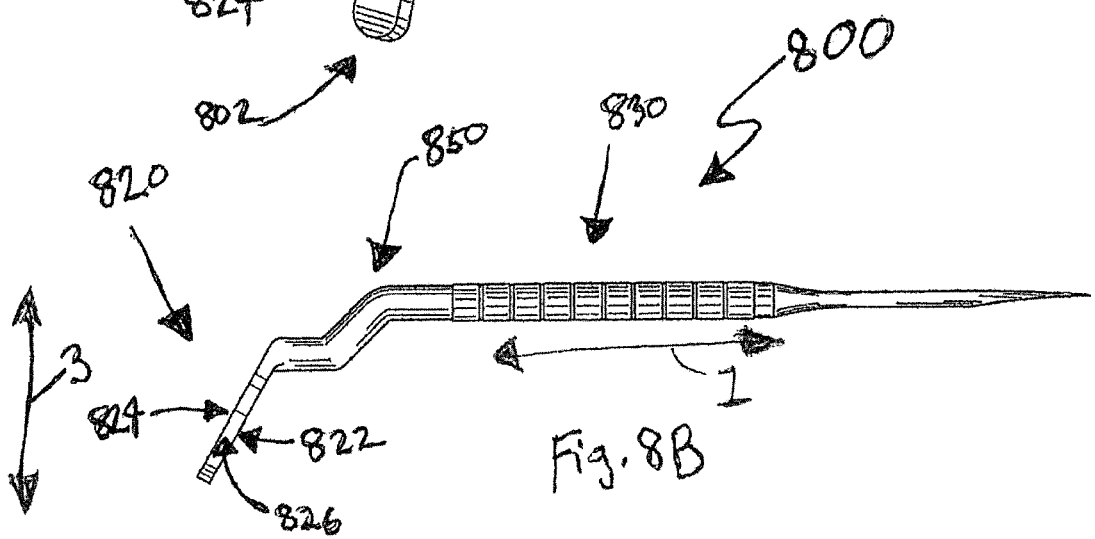
FIG. 8B is a left side view of the dental tool of FIG. 8A.
Figure 8C:
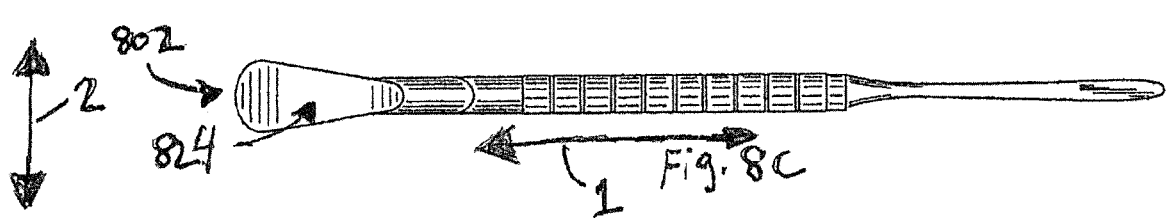
FIG. 8C is a top view of the dental tool of FIG. 8A.
Figure 8D:
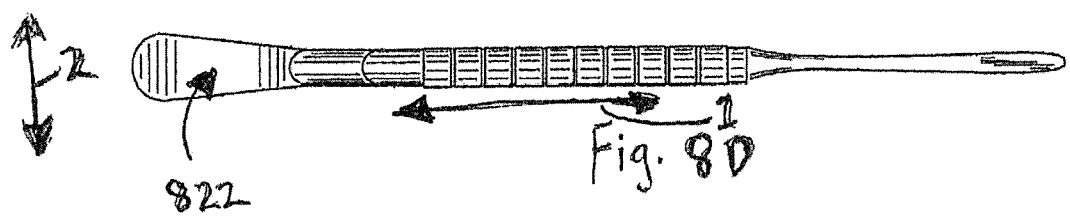
FIG. 8D is a bottom view of the dental tool of FIG. 8A.
Figures 8E, 8F:
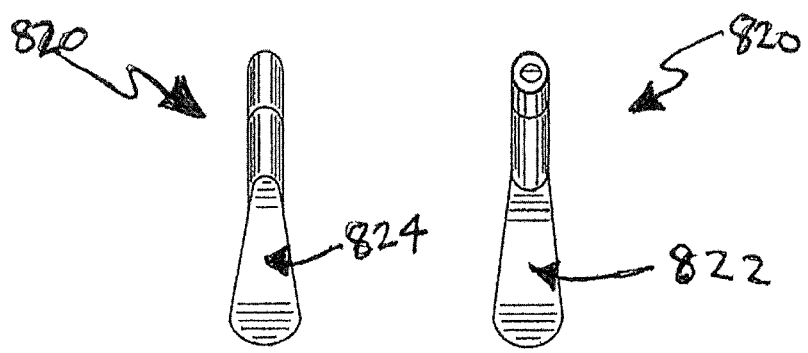
FIG. 8E is a top detailed view of a tongue and flap retractor portion of the dental tool shown in FIG. 8A.
FIG. 8F is a bottom detailed view of a tongue and flap retractor portion of the dental tool shown in FIG. 8A.
Figure 8G:
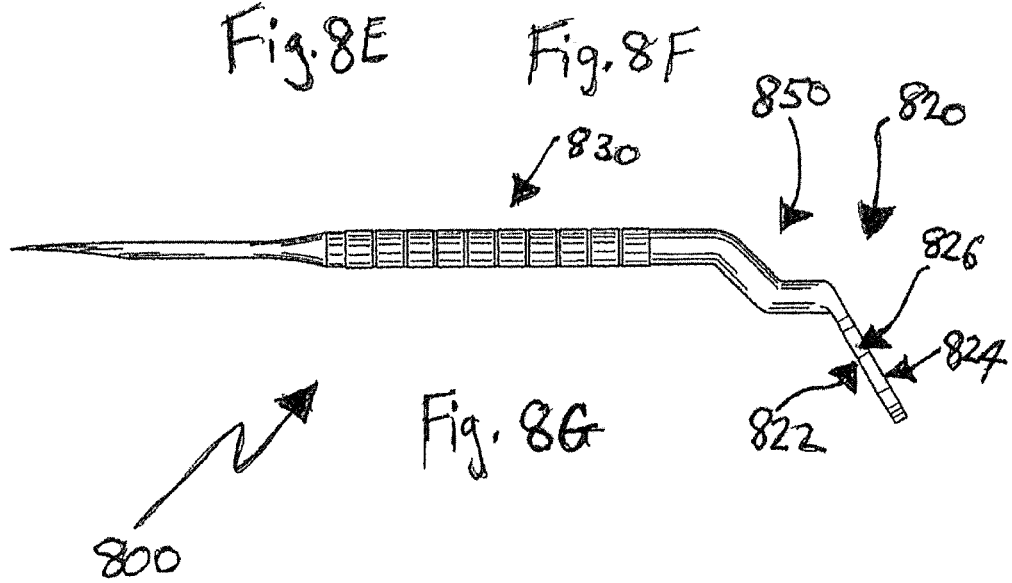
FIG. 8G is a right side view of the dental tool of FIG. 8A.
Figure 9A:
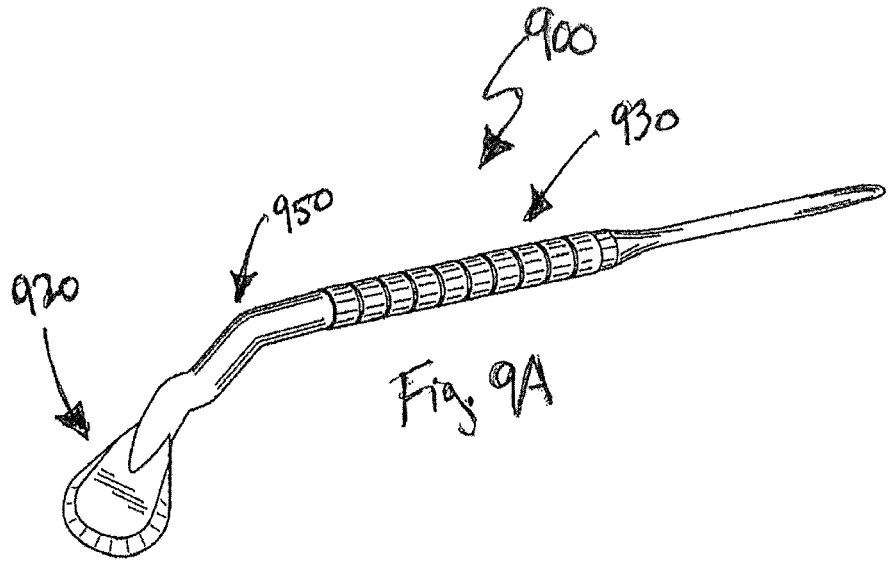
FIG. 9A is a perspective view of a ninth embodiment dental tool.
Figure 9B:
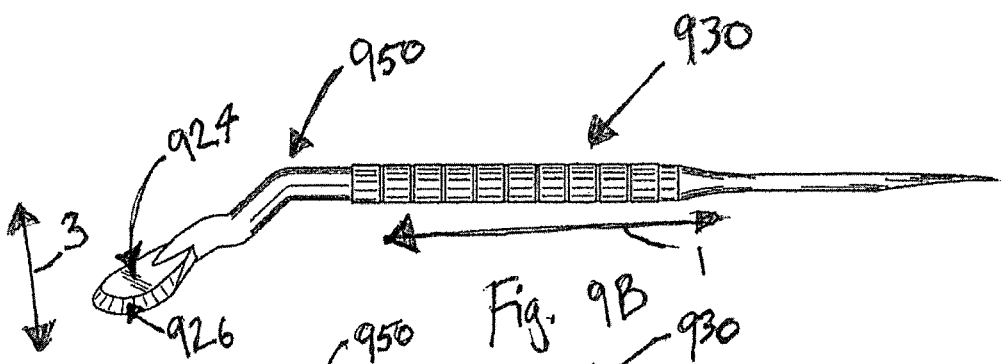
FIG. 9B is a side view of the dental tool of FIG. 9A.
Figure 9C:
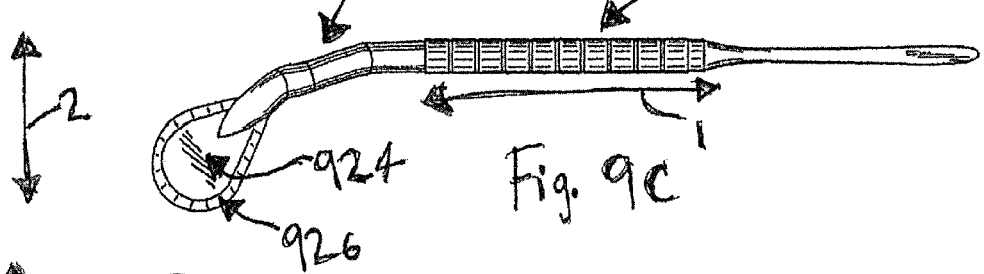
FIG. 9C is a top view of the dental tool of FIG. 9A.
Figure 9D:
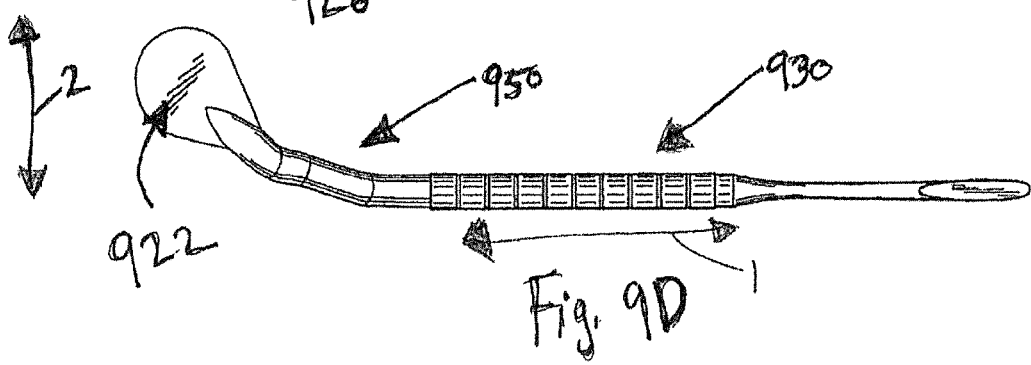
FIG. 9D is a bottom view of the dental tool of FIG. 9A.
Figure 9E:
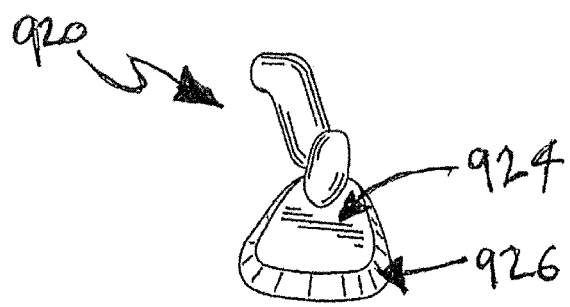
FIG. 9E is a top detailed view of a tongue and flap retractor portion of the dental tool shown in FIG. 9A.
Figure 9F:
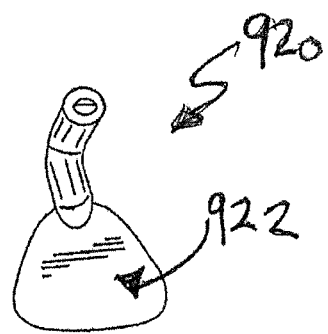
FIG. 9F is a bottom detailed view of a tongue and flap retractor portion of the dental tool shown in FIG. 9A.

FIGS. 8A-8G illustrate another embodiment tool 800, having an embodiment combined tongue and flap retractor 820, which is coupled to the handle region 830 by way of a neck region 850 that is S-shaped in the transverse plane (defined by the longitudinal direction 1 and the transverse direction 3, as shown in FIGS. 8B and 8G), and straight in the lateral plane (defined by the longitudinal direction 1 and the lateral direction 2, as shown in FIGS. 8C and 8D). The flap retractor 820 makes it useful for reflecting a soft tissue flap, such as the gingiva and/or gingival mucosa and/or connective tissue that has been raised as a surgical flap on the lingual aspect of the mandible. However, the exceptional thickness of the working end of the tool also makes it suitable for use as a tongue retractor, providing the sturdiness needed to reflect the relatively strong muscle of the tongue. The flap retractor 820 has a top face 824 that is substantially parallel to a bottom face 822, in which these faces 822, 824 are separated from each other by a lateral sidewall 826 providing a uniform thickness of from 0.1 mm to 5 mm, more preferably still from 2 mm to 4 mm, and more preferably about 3 mm. It is this unconventional thickness that gives the tool 800 its unexpected tongue-retracting abilities. In some other embodiments, at its most distal edge, this thickness may taper, such as to about 0.1 mm in thickness. Alternatively, the top face 824 and bottom face 822 may not be parallel to each other, but instead angled to provide a gentle tapering from the proximal end to the distal end. The lateral sidewall 826 extends around the sides and distal end of the flap retractor 820 and is substantially perpendicular to the top and bottom faces 822, 824. The distal end 802 of the flap retractor 820 is semicircular in shape, and preferably has extents along the lateral direction 2 from 5 to 30 mm, more preferably 10 mm to 20 mm, more preferably still about 15 mm. The ventral surface of the combined tongue and flap retractor 820 preferably has extents along the longitudinal direction 1 of from 5 mm to 40 mm, preferably from 10 mm to 30 mm, more preferably still about 28 mm. The embodiment flap retractor 820 is shown having a flat distal surface; it will be appreciated, however, that the distal edge of flap retractor 820 may also be curved.

FIGS. 9A-9F illustrate another embodiment tool 900, having a combined tongue and flap retractor 920. In the embodiment tool 900 the neck region 950 is S-shaped in the transverse plane (defined by longitudinal direction 1 and transverse direction 3 and best shown in FIG. 9B) and is C-shaped in the lateral plane (defined by longitudinal direction 1 and lateral direction 2 and best shown in FIGS. 9C and 9D). Hence, the retractor 920 is laterally offset from the handle region 930, both spatially and angularly, such as by about 25 to 40 degrees transversely, preferably about 30 degrees, and 30 degrees laterally, or more preferably 22 or 33 degrees laterally, with a corresponding transverse spatial displacement and a lateral spatial displacement as discussed in reference to earlier embodiments. In shape the embodiment tongue and flap retractor 920 is similar to the embodiment tongue and flap retractor 820. However, unlike the earlier embodiment flap refractor 820, the lateral sidewall 926 between the top surface 924 and bottom surface 922 is not substantially perpendicular to these surfaces 922, 924. Instead, the sidewall 926 is angled or beveled, such as by 1 to 60 degrees to the bottom surface 922, more preferably by 10 to 60 degrees, more preferably still by 15 to 45 degrees, yet more preferably still by about 33 degrees. Also, the length of the ventral surface of combined tongue and flap retractor 920 along the longitudinal direction 1 may be from 15 mm to 30 mm, more preferably 18 to 25 mm, more preferably still 20 mm. The dorsal surface 924 is thus slightly smaller in area than the ventral surface 922, and the sidewall 926 forms a beveled surface that makes it easier for the Dentist to insert the flap retractor 920 into an incision to hold the flap of soft tissue (such as gingiva, gingival mucosa and/or connective tissue) away from the treatment area. As in the above embodiment 800, it will be appreciated that the lateral sidewall 926 may also be curved.

FIGS. 10A-10F illustrate another embodiment tool 1000, having an embodiment tongue and flap retractor 1020. In the embodiment tool 1000 the neck region 1050 is S-shaped in the transverse plane (defined by longitudinal direction 1 and transverse direction 3 and best shown in FIG. 10B) and is straight in the lateral plane (defined by longitudinal direction 1 and lateral direction 2 and best shown in FIGS. 10C and 10D), although it will be appreciated that bends in the lateral direction are also contemplated. In shape the embodiment tongue and flap refractor 1020 is similar to the earlier embodiment flap retractor 920. However, the spacing between the dorsal surface 1024 and the ventral surface 1022 is less than that in the earlier embodiment flap retractors 820, 920. For this embodiment flap retractor 1020, the distance between the dorsal surface 1024 and the ventral surface 1022 is from 0.5 mm to 2.0 mm, more preferably from 0.8 mm to 1.5 mm, more preferably still about 1.0 mm. Because of its thinner aspect, the beveling of the sidewall 1026 may be steeper than in the second embodiment tongue and flap refractor 920. For example, the sidewall 1026 can be angled by about 45 degrees. The tool 1000 may be configured to have a smaller profile along the lateral 2 and longitudinal 1 extents for negotiating small anatomies, such as in children. Also, the tool 1000 may be well adapted for working in the lingual anterior region where the soft tissue is thin. The distal end of the flap retractor 1020 is semicircular or flat in shape, and preferably has extents along the lateral direction 2 from 3 to 24 mm, more preferably 5 mm to 18 mm, more preferably still about 12 mm. The ventral surface of the flap retractor 1020 preferably has extents along the longitudinal direction 1 of from 5 mm to 36 mm, preferably from 8 mm to 24 mm, more preferably still about 18 mm. As in the above embodiments 800, 900, it will be appreciated that the lateral sidewall 1026 may also be curved.

Figure 11A:
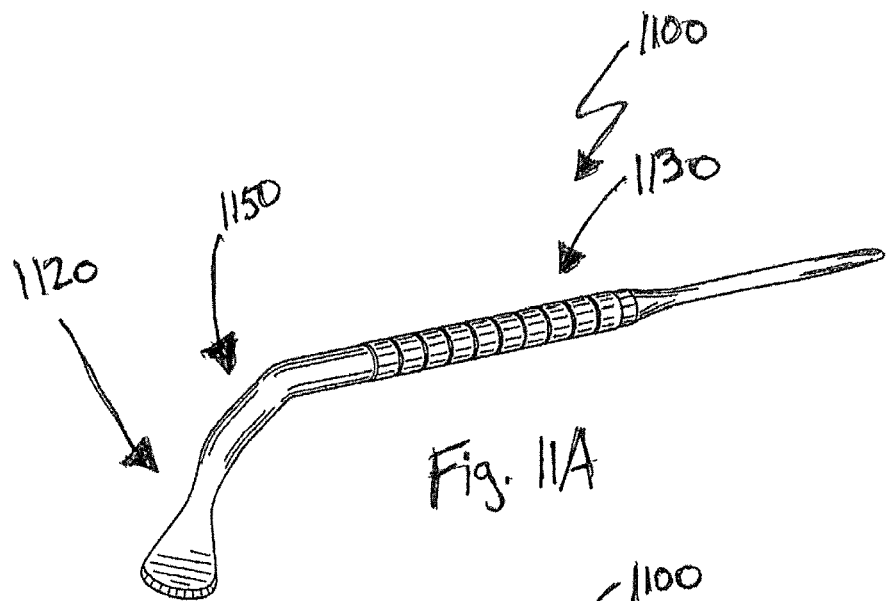
FIG. 11A is a perspective view of an eleventh embodiment dental tool.
Figure 11B:
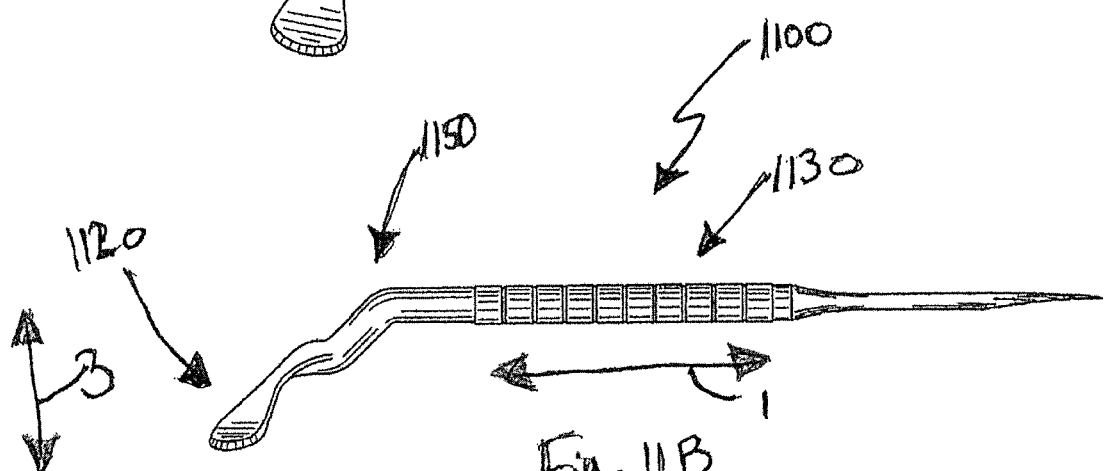
FIG. 11B is a left side view of the dental tool of FIG. 11A.
Figure 11C:
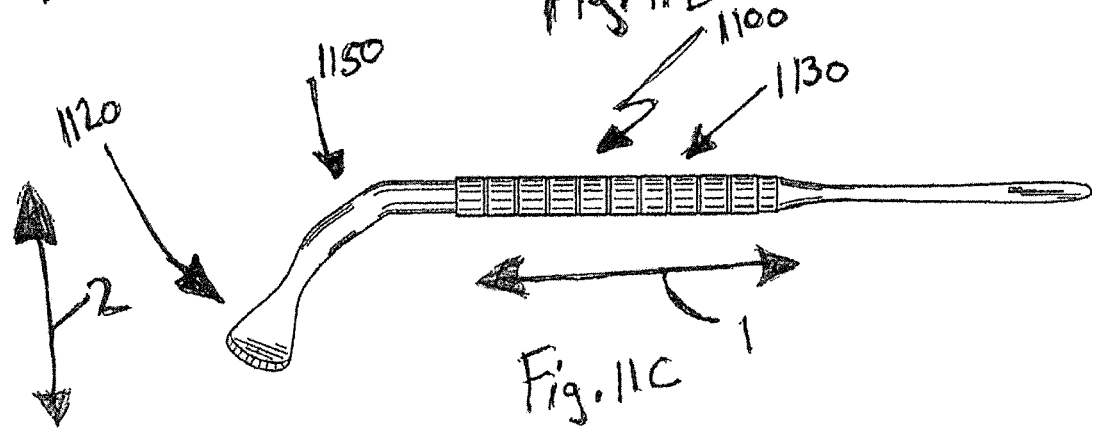
FIG. 11C is a top view of the dental tool of FIG. 11A.
Figure 11D:
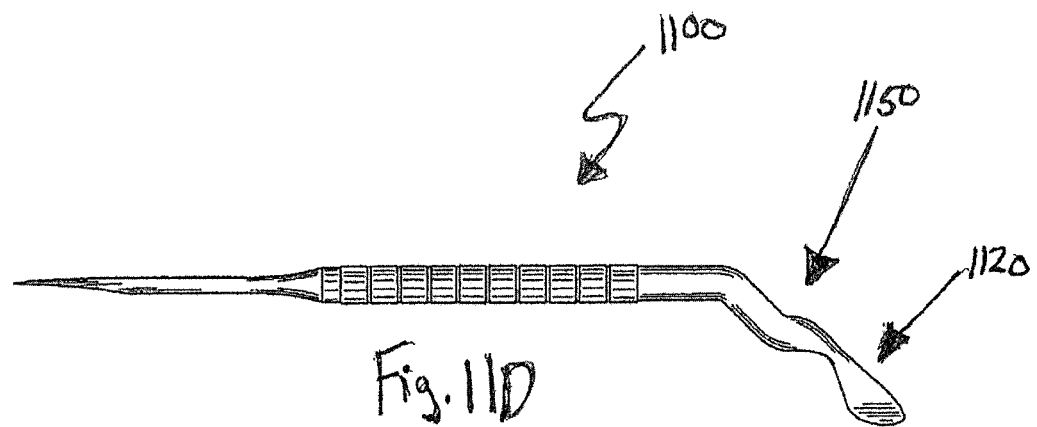
FIG. 11D is a right side view of the dental tool of FIG. 11A.
Figure 11E:
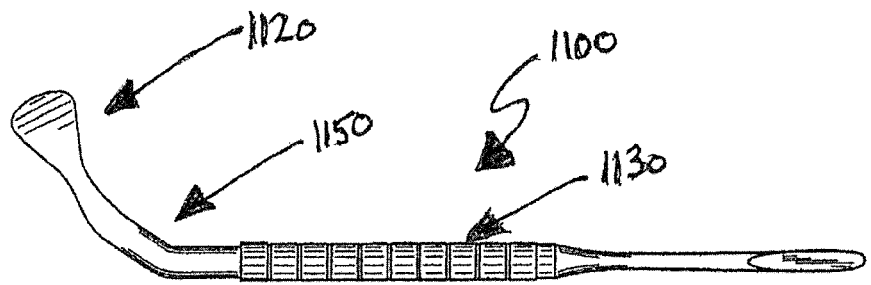
FIG. 11E is a bottom view of the dental tool of FIG. 11A.
Figure 11F:
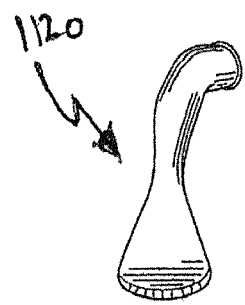
FIG. 11F is a top detailed view of a flap retractor portion of the dental tool shown in FIG. 11A.
Figure 11G:
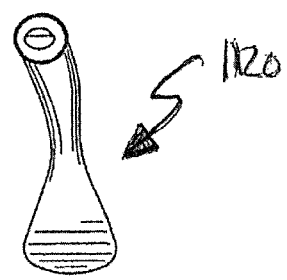
FIG. 11G is a bottom detailed view of a flap retractor portion of the dental tool shown in FIG. 11A.
Figures 12A, 12B, 12C, 12D, 12E:
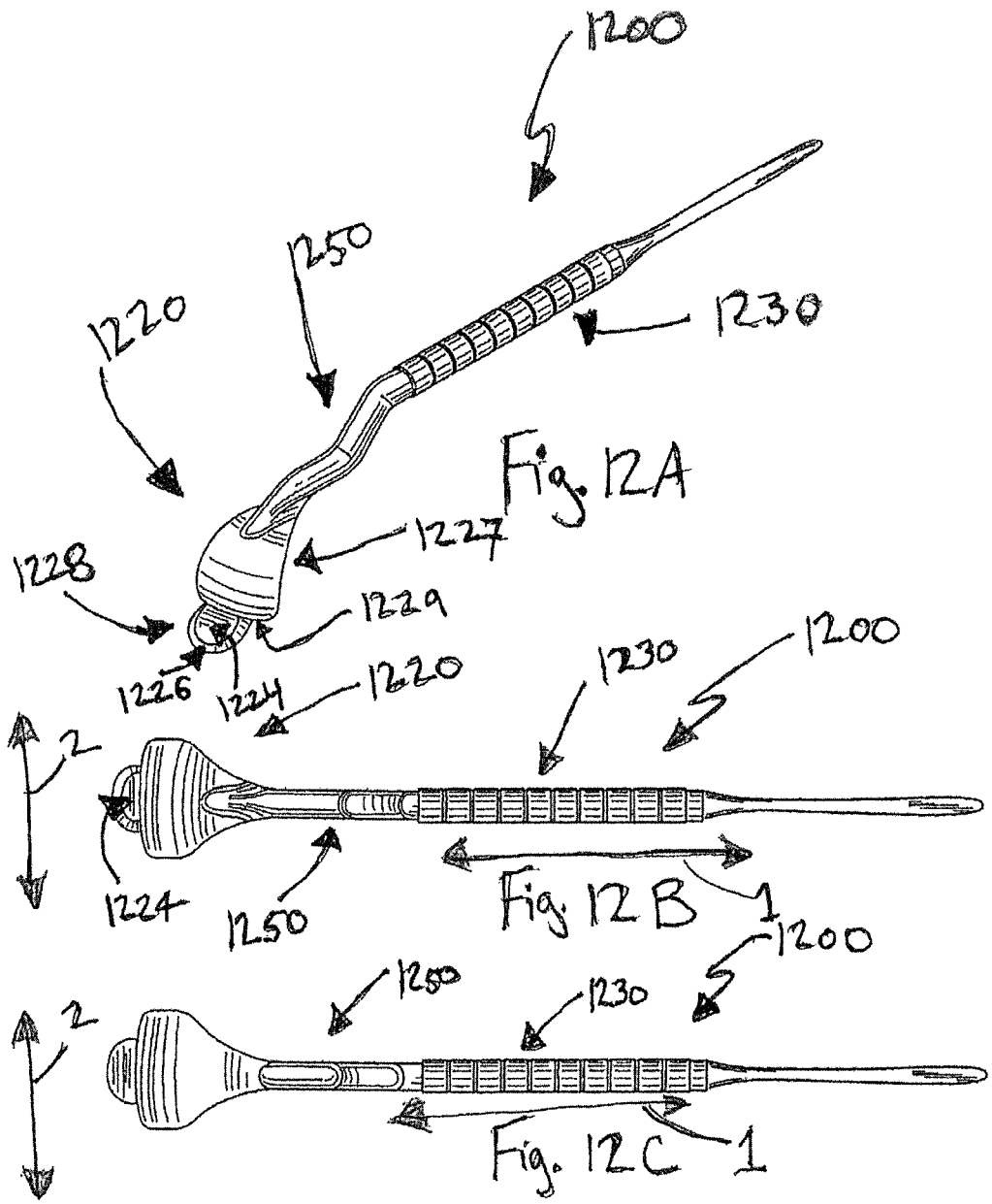
FIG. 12A is a perspective view of a twelfth embodiment dental tool.
FIG. 12B is a top view of the dental tool of FIG. 12A.
FIG. 12C is a bottom view of the dental tool of FIG. 12A.
FIG. 12D is a top detailed view of a combined tongue and flap retractor portion of the dental tool shown in FIG. 12A.
FIG. 12E is a bottom detailed view of a combined tongue and flap retractor portion of the dental tool shown in FIG. 12A.

FIGS. 11A-11G illustrate another embodiment tool 1100, having a tongue and flap retractor 1120 similar to the tongue and flap retractor 1020, which is coupled to the handle region 1130 by way of a neck region 1150 that is S-shaped in the transverse plane (defined by the longitudinal direction 1 and the transverse direction 3, as shown in FIG. 11B), and C-shaped in the lateral plane (defined by the longitudinal direction 1 and the lateral direction 2, as shown in FIG. 11C). The lateral and transverse angular and spatial displacements may be as described in relation to the earlier embodiments; preferred bends, however, are 22 to 33 degrees in the left or right lateral directions based upon the working location on the mandible.

FIGS. 12A-12E Figs. illustrate another embodiment tool 1200, having an embodiment combined tongue and flap retractor 1220, which is coupled to a distal end of the handle region 1230 by way of a neck region 1250 that is S-shaped in the transverse plane. The combined tongue and flap retractor 1220 has a tongue retractor portion 1227 that is shaped substantially similarly to the first embodiment tongue retractor 120. However, a flap refractor portion 1228 extends distally, substantially along the longitudinal direction 1, from the distal end 1229 of the tongue retractor portion 1227. The tongue retractor portion 1227 is thus disposed proximal to the flap retractor portion 1228, with the flap retractor portion 1228 being located at a most distal region of the device 1200. The flap retractor portion 1228 may be centrally aligned with the tongue retractor portion 1227, and can include a beveled edge 1226 to facilitate insertion of the flap retractor portion 1228 into an incision in order to reflect a soft tissue flap (e.g., gingiva, gingival mucosa and/or connective tissue). The flap retractor portion 1228 may have a lateral width 2 and thickness (which beveled surface 1226 extends through) similar to other embodiment flap retractors disclosed herein, but preferably from about 0.3 to 1 mm, and a longitudinal length 1 (as measured from the connection location with the tongue retractor portion 1227 to the most distal end of the flap retractor portion 1228) of from 1 mm to 15 mm, preferably from 2 mm to 10 mm, more preferably still about 6 to 7 mm. The width 2 is preferably about 5 to 20 mm, more preferably 10 mm to 15 mm, more preferably still about 13 mm. Any suitable angle, for example as discussed in certain embodiments above, may be used for the angle of the beveled edge 1226. Sidewalls as disclosed with reference to the first embodiment flap retractor 800 may also be employed rather than beveled edges 1226. In some embodiments the dorsal surface 1224 (or ventral surface) of the flap retractor portion 1228 is parallel with the lateral plane defined by the longitudinal direction 1 and the lateral direction 2 (i.e., a planar surface perpendicular to the transverse direction). However, in preferred embodiments the dorsal surface 1224 (or ventral surface) is at an angle, in the ventral, transverse direction, to the lateral plane, such as from 0 degrees to 75 degrees, more preferably from 5 to 60 degrees, more preferably still from 5 degrees to 45 degrees, and yet more preferably still at about 15 degrees to the longitudinal axis 1 of the handle region. The combined tongue and flap retractor 1220 may be used to perform both functions (tongue retraction and flap retraction) simultaneously or separately depending on the Dentist's needs. Combining these functions into a single device 1200 eliminates the need for two separate devices in the oral cavity during procedures, frees up a hand of the Dentist for other potential uses or eliminates the need to have an assistant's hand in the treatment area, shortening the time of operation. In some embodiments a shortened flap retractor portion 1228 may be provided, which may be useful if the anatomy is small, i.e., children or small adults, such as a retractor that is 1 mm to 4 mm in length, more preferably about 2 mm in length.

Figure 13F:
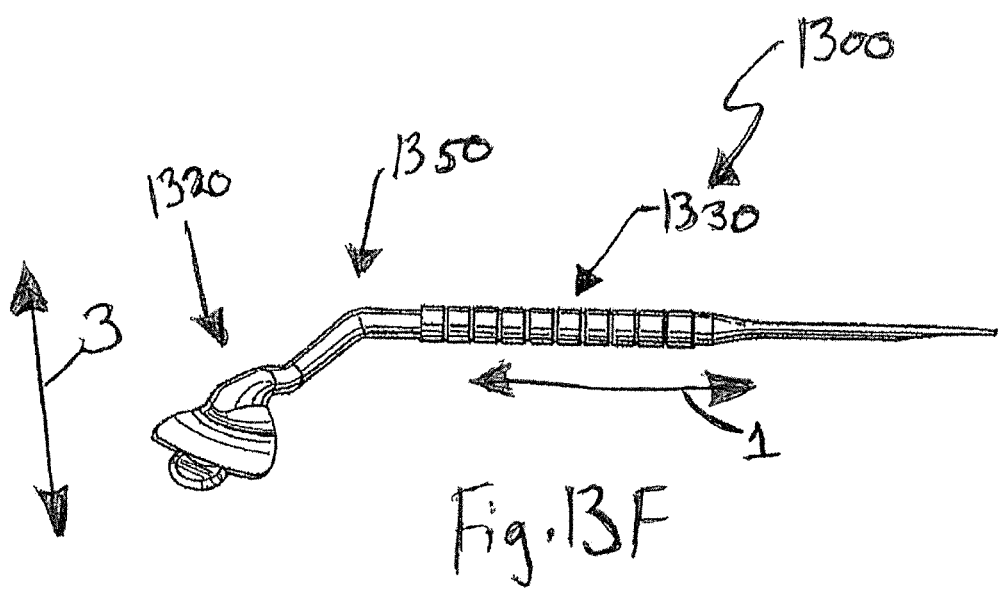
FIG. 13F is a side view of the dental tool of FIG. 13A.

FIGS. 13A-13F illustrate another embodiment tool 1300, having a combined tongue and flap retractor 1320 similar to the embodiment tongue and flap retractor 1220, which is coupled to the handle region 1330 by way of a neck region 1350 that is S-shaped in the transverse plane (defined by the longitudinal direction 1 and the transverse direction 3, as shown in FIG. 13F), but which is C-shaped in the lateral plane (defined by the longitudinal direction 1 and the lateral direction 2, as shown in FIGS. 13B and 13C). Any suitable angular and spatial offsets may be used, as discussed in the earlier embodiment tools.

Figures 14A, 14B, 14C, 14D, 14E, 14F:
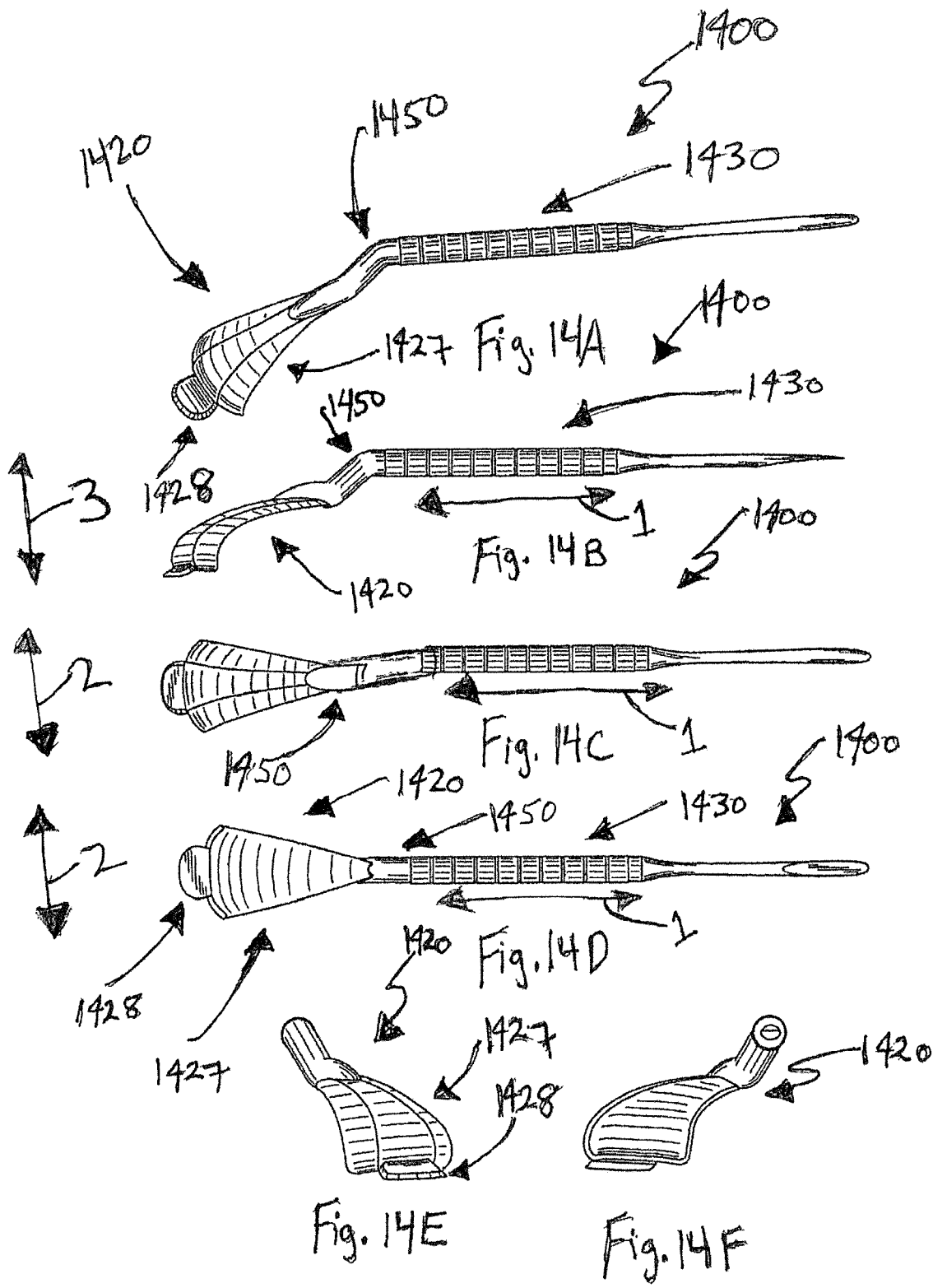
FIG. 14A is a perspective view of a fourteenth embodiment dental tool.
FIG. 14B is a side view of the dental tool of FIG. 14A.
FIG. 14C is a top view of the dental tool of FIG. 14A.
FIG. 14D is a bottom view of the dental tool of FIG. 14A.
FIG. 14E is a top detailed view of a combined tongue and flap retractor portion of the dental tool shown in FIG. 14A.
FIG. 14F is a bottom detailed view of a combined tongue and flap retractor portion of the dental tool shown in FIG. 14A.

FIGS. 14A-14F illustrate another embodiment tool 1400, having an embodiment combined tongue and flap retractor 1420 that is similar to the earlier embodiment combined tongue and flap retractor 1220 but in which the tongue retractor portion 1427 is shaped similarly to the embodiment tongue retractor 420 to provide an exaggerated cavity to retract the patient's tongue. The combined tongue and flap retractor 1420 is coupled to the handle region 1430 by way of a neck region 1450 that is S-shaped in the transverse plane (defined by the longitudinal direction 1 and the transverse direction 3, as shown in FIG. 14B), and straight in the lateral plane (defined by the longitudinal direction 1 and the lateral direction 2, as shown in FIGS. 14C and 14D).

FIGS. 15A-15F illustrate another embodiment tool 1500, having a combined tongue and flap retractor 1520 similar to the embodiment tongue and flap retractor 1420, which is coupled to the handle region 1530 by way of a neck region 1550 that is S-shaped in the transverse plane (defined by the longitudinal direction 1 and the transverse direction 3, as shown in FIG. 15B), but which is L-shaped in the lateral plane (defined by the longitudinal direction 1 and the lateral direction 2, as shown in FIGS. 15C and 15D). The lateral angular displacement of the combined tongue and flap retractor 1520 may be as discussed in earlier embodiment tools, for example, from 0 degrees to 180 degrees, but preferably from 20 degrees to 35 degrees, more preferably 22 degrees or 33 degrees. As best shown in FIG. 15B, the plane of the dorsal surface 1524 of the flap retractor portion 1528 may be parallel or substantially parallel to the lateral plane of the tool 1500. However, in particularly preferred embodiments the dorsal surface 1524 is angled ventrally in the transverse direction 3 by about 0 degrees to 90 degrees, more preferably from 0 to 30 degrees and more preferably still by about 15 degrees.

FIGS. 16A-16G illustrate another embodiment tool 1600, having an embodiment combined tongue and flap retractor 1620 coupled to the handle region 1630 by way of a neck region 1650 that is S-shaped in the transverse plane (defined by the longitudinal direction 1 and the transverse direction 3, as shown in FIGS. 16B and 16G), and straight in the lateral plane (defined by the longitudinal direction 1 and the lateral direction 2, as shown in FIGS. 16C and 16D). It will be appreciated, however, that lateral bends to the right or left are also possible. As best shown in FIG. 16B, the tongue refractor portion 1627 is substantially flat and due to the S-shaped neck region 1650 is at an angle of about 10 degrees to 90 degrees, and preferably about 45 degrees relative to the longitudinal length 1 of the handle portion 1630 (i.e., to the lateral plane of the tool 1600). The distal end 1629 of the tongue retractor portion 1627 may have a lateral width 2 as discussed in previous embodiment tongue refractors, and preferably about 27 mm, while the tongue retractor portion 1627 may have a length of from 10 mm to 50 mm, and preferably about 30 mm. The flap refractor portion 1628 is coupled to the dorsal surface 1621 of the tongue retractor portion 1627 and extends beyond the distal end 1629 of the tongue retractor portion 1627. The distal end 1602 of the flap retractor portion 1628 may have a width in the lateral direction 2 of about 5 mm to 20 mm, more preferably 10 mm to 15 mm, more preferably still about 13 mm, while the flap retractor portion 1628 may extend from the distal end 1629 of the tongue retractor portion 1627 by 1 mm to 15 mm, preferably from 2 mm to 10 mm, more preferably still about 6 mm. The top surface 1624 of the flap retractor portion 1628 may be substantially parallel to the top surface 1621 of the tongue retractor portion 1627. In other embodiments the top surface 1624 of the flap retractor portion 1628 may have a transverse angular displacement with respect to the lateral plane of the device by 0 degrees to 90 degrees, more preferably from 5 degrees to 30 degrees, with about 15 degrees being particularly preferred. The flap retractor portion 1628 may directly extend from a most distal edge 1629 of the tongue retractor portion 1627, or may instead extend out from a top surface 1621 of the tongue retractor portion 1627.

Figure 17E:
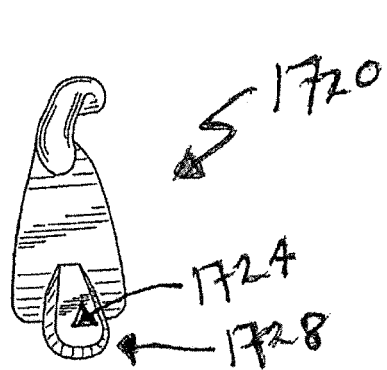
FIG. 17E is a top detailed view of a combined tongue and flap retractor portion of the dental tool shown in FIG. 17A.
Figure 17F:
FIG. 17F is a bottom detailed view of a combined tongue and flap retractor portion of the dental tool shown in FIG. 17A.

FIGS. 17A-17F illustrate another embodiment tool 1700, having a combined tongue and flap retractor 1720 similar to the embodiment tongue and flap retractor 1620, which is coupled to the handle region 1730 by way of a neck region 1750 that is S-shaped in the transverse plane (defined by the longitudinal direction 1 and the transverse direction 3, as shown in FIG. 17B), and C-shaped in the lateral plane (defined by the longitudinal direction 1 and the lateral direction 2, as shown in FIGS. 17C and 17D). The lateral angular displacement of the combined tongue and flap retractor 1520 may be, for example, about 22 or 33 degrees, either to the right or to the left. The plane of the dorsal surface 1724 of the flap retractor portion 1728 may be angled ventrally in the transverse direction 3 with respect to the lateral plane of the tool 1700 by about 5 to 30 degrees, and more preferably by about 15 degrees.

Figure 18D:
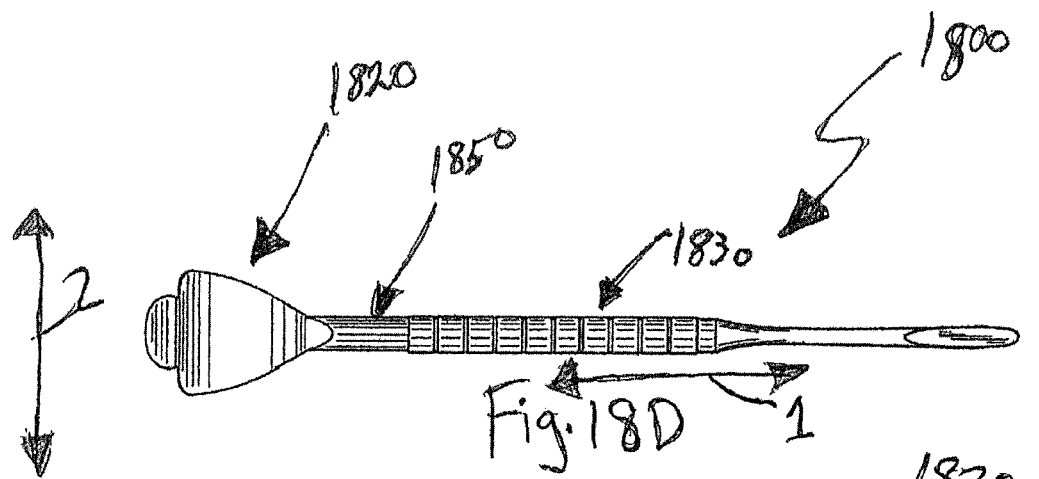
FIG. 18D is a bottom view of the dental tool of FIG. 18A.
Figures 18E, 18F:
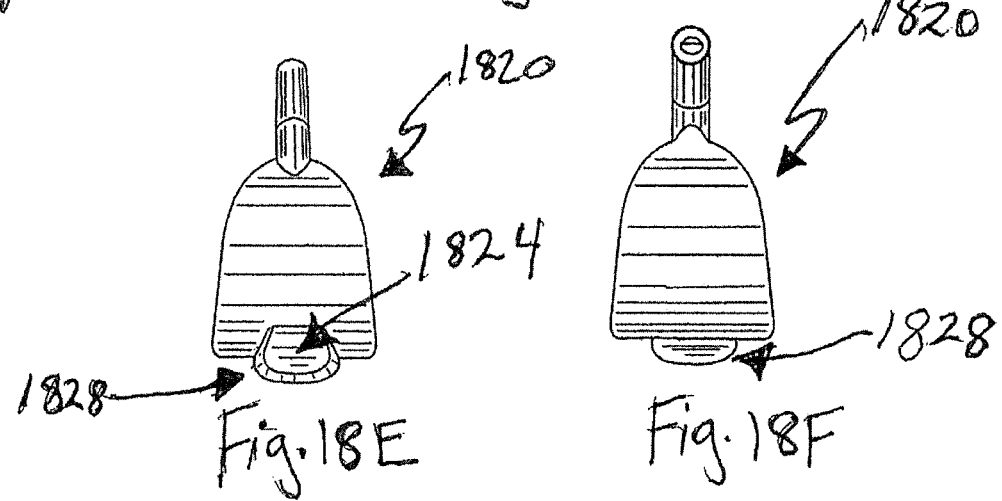
FIG. 18E is a top detailed view of a combined tongue and flap retractor portion of the dental tool shown in FIG. 18A.
FIG. 18F is a bottom detailed view of a combined tongue and flap retractor portion of the dental tool shown in FIG. 18A.
Figure 18G:
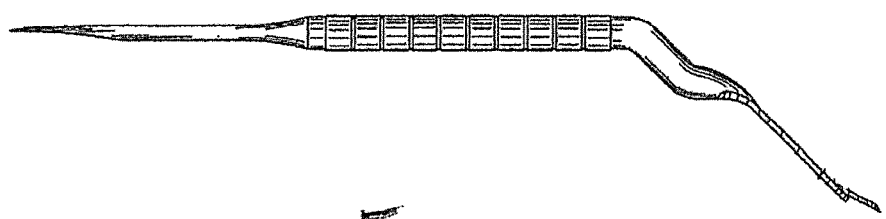
FIG. 18G is a right side view of the dental tool of FIG. 18A.

FIGS. 18A-18G illustrate another embodiment tool 1800, having a combined tongue and flap retractor 1820 similar to the embodiment tool 1600, but for which the tongue retractor portion has an extended width, and may have a most distal width 1829 along lateral direction 2, for example, about 26 mm to 35 mm, preferably about 32 mm. The width of flap retractor portion 1828 preferably has a width of about 5 mm to 20 mm, more preferably 10 mm to 15 mm, more preferably still about 15 mm. The working element 1820 is coupled to the handle region 1830 by way of a neck region 1850 that is S-shaped in the transverse plane (defined by the longitudinal direction 1 and the transverse direction 3, as shown in FIGS. 18B and 18G), and straight in the lateral plane (defined by the longitudinal direction 1 and the lateral direction 2, as shown in FIGS. 18C and 18D). The plane of the dorsal surface 1824 of the flap retractor portion 1828 may be angled ventrally in the transverse direction 3 with respect to the lateral plane of the tool 1800 by about 5 to 30 degrees, more preferably by about 15 degrees.

FIGS. 19A-19G illustrate another embodiment tool 1900 that is substantially similar to the embodiment tool 1600. However, the tongue retractor 1920 that is substantially similar to the embodiment tongue and flap retractor 1620 does not include a flap retractor portion. Hence, the embodiment tool 1900 provides only the functionality of a tongue retractor, in addition to the other functionality provided by first operational unit 1910.

FIGS. 20A-20F illustrate another embodiment tool 2000, having a tongue retractor 2020 similar to the embodiment tongue retractor 1920, which is coupled to the handle region 2030 by way of a neck region 2050 that is S-shaped in the transverse plane (defined by the longitudinal direction 1 and the transverse direction 3, as shown in FIG. 20B), and C-shaped in the lateral plane (defined by the longitudinal direction 1 and the lateral direction 2, as shown in FIGS. 20C and 20D). The lateral angular displacement of the tongue retractor 2020 may be, for example, about 22 or 33 degrees, which may be in either the right or left direction depending upon the working area in the mandible.

FIGS. 21A-21F illustrate another embodiment tool 2100, having a tongue retractor 2120 similar to the embodiment tongue refractor 700. However, as best shown in FIG. 21E, the most distal edge 2129 is not level with, or parallel to, the lateral plane of the device 2100 defined by the longitudinal direction 1 and the lateral direction 2. The lateral plane is shown in FIG. 21E as dotted line 2101. An inclination angle 2103 exists between the inferior border of the device 2120 and the lateral plane 2101, and as a result a first lateral edge 2121 of the tongue retractor 2120 is longer than its opposing second lateral edge 2122. The inclination angle 2103 is preferably from 5 degrees to 30 degrees, more preferably still from 8 degrees to 20 degrees, with 8 degrees and 10 degrees being particularly preferred. It will be appreciated that providing an inclination angle to the most distal edge of the second operational unit, such as tongue retractors and flap retractors, or combinations thereof, may be implemented in all of the embodiments discussed herein. The tool 2100 provides yet another way to negotiate the anatomy of the mouth where one side is naturally lower as the Dentist moves in the posterior direction within the mouth, providing improved tongue retraction capabilities. Hence, it will be understood that the first lateral edge 2121 and the second lateral edge 2122 may be on left or right sides based upon the working region in mouth.

FIGS. 22A-22F illustrate another embodiment tool 2200, having a combined tongue and flap retractor 2220 similar to the earlier embodiment tongue and flap retractor 1500. However, the working end of the tool 2200 is rotated to obtain an effect similar to earlier embodiment tools. With reference to FIG. 22A, the working end of the tool 2200 may have a neck region that is, for example, S-shaped in the transverse plane and L-shaped in the lateral plane, provided by a first bend 2222 and a more distal second bend 2224. The lateral angular displacement may be, for example, from 5 degrees to 90 degrees, more preferably from 15 degrees to 45 degrees, more preferably still 22 degrees or 33 degrees, and provided completely by the second bend 2224. The ventral, transverse angular displacement may be, for example, from 0 to 90 degrees, preferably from 20 to 60 degrees, and more preferably about 33 or 45 degrees in total as provided by both bends 2222, 2224. More generally, the various angular extents of these bends 2222, 2224 may be as in any of the embodiments described herein, and may be exclusively within the lateral planes and the transverse planes. It will be appreciated, however, that an L-shaped or C-shaped bend in the lateral plane is not required to provide rotational offsets as discussed herein; that is, the instruments may also be straight along the longitudinal direction 1, while also having a rotational offset of the working end. Further, it will be appreciated that such rotations of the working end may be applied to any tool discussed herein. These bends 2222, 2224 may define axes; for example, a first axis 2226 may be defined as running along a line connecting the first bend 2222 to the second bend 2224, while a second axis 2228 may be defined as running along a line connecting the second bend 2224 to the midline of the working end of the tool 2200. In addition to spatial displacements provided by these bends 2222, 2224, the working end 2220 may also undergo rotational displacements, and in particular rotational displacements along the second axis 2228 that directly couples to the working end 2220 of the tool 2200. For example, the working end may be rotated by 5 degrees to 90 degrees, more preferably from 20 degrees to 45 degrees, more preferably still by 25 degrees or 35 degrees, around the second axis 2228. Hence, the rotational orientation of the working end 2220 of the tool 2200 (which may be defined by the longitudinal and lateral extents of the working end 2220) may be offset from that of the handle and neck regions, and in particular may be offset from (i.e., form an angle with respect to) the lateral plane. This rotation of the working end (i.e., tongue and flap refractor 2220) of the tool 2200 may be anywhere along the axes 2228, 2226; in a preferred embodiment the rotation is imparted at bend 2224. Such rotational offsets of the working end of the tool 2200, or any other embodiment retractor discussed herein, provides the heretofore unappreciated benefit of allowing greater ease of access to the target tissue area, and thus reduces strain upon the Dentist. In particular, such rotational offsets may help to better align the working end of the tool with the target anatomy within the patient's mouth, and thus require less readjusting and manipulating by the Dentist to achieve the desired objective. Rotational offsets of from 5 to 45 degrees may be particularly beneficial in this regard.

FIGS. 23A-23F illustrate another embodiment tool 2700, a first embodiment multi-purpose tool 2700 that combines tongue and flap retraction with a suction device. Preferably the device 2700 is integrally formed from any suitable material, such as plastic, and is disposable. The multi-purpose tool 2700 includes a hollow, tubular portion 2704 that terminates in a distal end 2702 with a combined tongue and flap retractor 2720. The tubular section 2704 may have any suitable cross-sectional shape, such as rectangular, elliptical, hexagonal, octagonal or, as shown in FIGS. 23A-23F, substantially round; this cross-sectional shape may change from the proximal end 2701 to the distal end 2702. The proximal end 2701 of the tubular section 2704 is preferably round to accept a standard vacuum-providing hose and includes a stop ring 2705. A neck region 2750 of the tubular section 2704 connects the distal end 2702, and in particular the combined tongue and flap refractor 2720, to a handle region 2730. As shown in FIG. 23C, the neck region 2750 may be S-shaped in the transverse plane (defined by the longitudinal direction 1 and the transverse direction 3), and straight in the lateral plane (defined by the longitudinal direction and the transverse direction 2).

The combined tongue and flap retractor 2720 may include a tongue retractor portion 2727 and a flap retractor portion 2728 as previously described in relation to other embodiment devices. For example, the tongue retractor portion 2727 may have dimensions that are similar to other embodiment tongue retractors disclosed herein, such as the tongue retractor portion 1627 discussed in relation to FIGS. 16A-16G. A flap retractor portion 2728, centrally aligned with the tongue retractor portion 2727, extends from the distal end 2729 of the tongue retractor portion 2727. The flap retractor portion 2728 may have dimensions as disclosed herein with respect to other embodiment flap retractors and flap retractor portions. In the embodiment shown, for example, in FIG. 23C, the flap retractor portion 2728 is co-planar with the tongue retractor portion 2727, but, as previously disclosed, the flap retractor portion 2728 may have a different angle with respect to the plane of the tongue retractor portion 2727.

A ventral surface 2722 of the tongue retractor portion 2727 is used to directly contact the tongue of the patient. A distal end region of tubular section 2704 is wholly disposed on top of and coupled to the dorsal surface 2721 of the tongue retractor portion 2727, with the opening 2709 of the distal end 2702 terminating at the distal edge 2729 of the tongue retractor portion 2727, and thus, in certain embodiments, proximally to the flap retractor 2728. The opening 2709 may be, for example, from 5 mm to 15 mm, preferably about 12 mm wide, with the height of the opening 2709 being from 5 to 15 mm, preferably about 10 mm.

FIGS. 24A-24G illustrate a second embodiment multi-purpose tool 2800, having a combined tongue and flap retractor 2820 similar to the first embodiment multi-purpose tool 2700 above but which is slightly curved rather than flat, which is coupled to the handle region 2830 by way of a neck region 2850 that is S-shaped in the transverse plane (defined by the longitudinal direction 1 and the transverse direction 3, as shown in FIG. 24C), but which is L-shaped in the lateral plane (defined by the longitudinal direction 1 and the lateral direction 2, as shown in FIG. 24B). This lateral displacement may be either to the right or to the left based upon the working area in the mandible, and the lateral angular offset is preferably 22 degrees or 33 degrees from the longitudinal axis.

FIGS. 25A-25F illustrate a third embodiment multi-purpose tool 2900 that is similar to the first embodiment multi-purpose tool 2700 above. However, the tongue retractor portion may be wider in the lateral direction, such as from about 26 mm to 35 mm, preferably about 32 mm.

FIGS. 26A-26G illustrate a fourth embodiment multi-purpose tool 3000, having a combined tongue and flap retractor 3020 similar to the multi-purpose tool 2800 above but with a norrower tongue retractor portion 3020, which is coupled to the handle region 3030 by way of a neck region 3050 that is S-shaped in the transverse plane (defined by the longitudinal direction 1 and the transverse direction 3, as shown in FIG. 26C), and L-shaped in the lateral plane (defined by the longitudinal direction 1 and the lateral direction 2, as shown in FIG. 26B).

FIGS. 27A-27G illustrate a first embodiment combined tongue retractor with suction tool 3100, which combines tongue retraction with a suction device. Preferably the device 3100 is integrally formed from any suitable material, such as plastic, and is disposable, as with the above multi-purpose devices. However, non-disposable devices are also contemplated, such as devices made from stainless steel or any other suitable material. The tool 3100 includes a hollow, tubular portion 3104 similar to the tubular portions discussed above. The neck region 3150 may be S-shaped in the transverse plane (defined by the longitudinal direction 1 and the transverse direction 3), C-shaped in the lateral plane (defined by the longitudinal direction 1 and the transverse direction 2), and connects the operational unit 3120 on the distal end to the handle region 3130. It will be appreciated, however, that the device could also be straight in the lateral plane. The operational unit 3120 is a tongue retractor 3124 in combination with a suction opening 3109. The tongue retractor 3124 may have a shape that is similar to the tongue retractor 400 discussed in relation to FIGS. 4A-4F, and thus has an exaggerated concavity, with the majority (i.e., 50% or more) of the curvature in the transverse direction 3 defining the cavity being within the last third or less of the longitudinal length of the retractor 3124. A lower lip 3110 of the distal end region of tubular section 3104 is disposed on top of and coupled to the dorsal surface of the tongue retractor 3124, so that opening 3109 is disposed just above the region in which the majority of the curvature occurs in the refractor 3124—i.e., just above the most distal third of the retractor 3124 and so is substantially aligned with the most distal extents of the tongue retractor 3124.

FIGS. 28A-28G illustrate a second embodiment combined tongue retractor with suction tool 3200, which is similar to the tool 3100 discussed above, but which has a lateral bend in the neck region. Furthermore, in the embodiment 3200, a most distal edge 3209 of distal opening 3202 extends beyond the most distal edge 3221 of tongue retractor 3220. The additional distal extension of the suction tube 3204 may be provided, for example, by a lower lip or the like. A distance of extension 3206 of the distal edge 3209 of suction tube 3204 with respect to the distal edge 3221 of tongue retractor 3220 may be from 0 mm to 10 mm, preferably about 6 mm. By way of example, the tool 3200 illustrates an embodiment having a 2 mm distance of extension 3206, whereas the tool 3400 shown in FIG. 30 and discussed in more detail below illustrates an embodiment having a 6 mm distance of extension 3499. With specific reference to FIG. 28B, the lip or extension 3209 may serve as a flap retractor. It will be appreciated that this distance of extension 3209 may also be zero, as in the embodiment 3100 discussed above, or even negative. Similarly, it should be appreciated that in the embodiment 3100 discussed above, the lower lip of the distal end region of tubular section 3104 may extend beyond the most distal extents of the tongue retractor 3120, similar to the distance of extension 3206 present in the this embodiment 3200.

FIGS. 29A-29F illustrate a third embodiment combined tongue retractor with suction tool 3300. In the tool 3300, the tubular body 3304 terminates at its distal end with an S-shaped region 3302, so that the distal opening 3306 of the tubular body 3304 is offset in the transverse direction 3 from the handle portion 3330. Opening 3306 may have any suitable dimensions, such as those set forth above for opening 2709. This transverse offset distance 3399 may be from 15 mm to 40 mm, more preferably from 20 mm to 30 mm, more preferably still about 28 mm. A tongue retractor 3320, similar to the tongue retractor 620 discussed in reference to FIGS. 6A-6G, is superimposed over the distal S-shaped portion 3302 of suction tube 3304. However, it will be appreciated that other types of tongue retractors as disclosed herein could also be used for this embodiment. A bottom 3309 of distal opening 3306 is substantially aligned with (i.e., within 2 mm of) the distal bottom 3329 of tongue retractor 3320. This bottom portion 3309 of opening 3306 may extend from 0 mm to 10 mm, preferably about 2 mm, beyond the distal extents of tongue refractor 3320. Because of the S-shaped curvature 3302 of the distal section of suction tube 3304, a region of the tube 3304 just proximal to the distal opening 3306 lies completely under the dorsal side 3324 of the tongue retractor 3320. Hence, the suction provided by the tube 3304 actually comes out through the distal end of the tongue retractor 3320, coming from the ventral side 3322 of the tongue retractor 3320 to the dorsal side 3324 of the tongue retractor 3320. This configuration permits the working end 3306 of the suction tube 3304 to get closer to the target site. By way of example of possible alternative embodiments, a tool similar to the tool 3300 may further include a lateral bend in the neck region, a rotational offset of the working end, or both.

FIGS. 30A-30F illustrate a fourth embodiment combined tongue retractor with suction tool 3400, which is similar to the tool 3300. However, in the tool 3400, the bottom extension 3409 of the distal end opening 3406 of suction tube 3404 has increased distal extents that can serve as a flap retractor. That is, the suction opening 3406 has a lower lip 3409 that extends further beyond the tongue retractor 3420. The length 3499 of this flap retractor 3409 from the top surface 3424 of the tongue retractor 3420 may be from 0 mm to 10 mm, more preferably about 6 mm. Lateral bends in the neck region, and rotational offsets of the working end are also possible. Also, it will be appreciated that other tongue retractor designs as disclosed herein may also be employed.

FIGS. 31A-31F illustrate a fifth embodiment combined tongue retractor with suction tool 3500, which is similar to the tool 3100. However, in contrast to the tool 3100, the suction opening 3509 is disposed proximally to the most distal extents of tongue retractor 3520, and so has a proximal offset 3599 with respect to the most distal extents of the tongue retractor 3520. The proximal offset 3599 may be from 1 mm to 30 mm, more preferably from 10 mm to 20 mm, more preferably still about 11 mm. Such a design may be beneficial as occasionally suction is better if the opening of the suction tube is slightly spaced from the actual working area; for example, the tool 3500 may suction spray from a hand piece better.

Reference is drawn to FIGS. 32A-32C, which present various views of a handle 3600 that may be utilized for the handle region of various of the above-described embodiment tools. Handle 3600 is substantially straight and made from a contiguous piece of material, which is preferably stainless steel, although other materials may also be used, such as plastic. Each end 3602 of handle 3600 may connect to a corresponding operational end and, as discussed in various of the embodiments above, and optional intervening neck region. These may be integrally formed with handle 3600, or may be attached to handle 3600, such as with a threaded connection or the like.

The exterior surface of handle 3600 comprises a plurality of surface features 3610 sequentially arrayed along a longitudinal length 3601 of handle 3600, which are separated from each other by corresponding dividers 3612. Preferably, each surface feature 3610 has a substantially identical length along longitudinal direction 3601 as every other surface feature 3610. Similarly, each divider 3612 has a substantially identical length along longitudinal direction 3601 as every other divider 3612. In this manner, the sequential array of surface features 3610 and corresponding dividers 3612 provides a visual cue of distance from an end 3602 of handle 3600; that is, the dividers 3612 function much like tick marks of a ruler, indicating distance from a corresponding end 3602 of handle 3600.

Each surface feature 3610 comprises knurling, which extends around the entire outer circumference of handle 3600 within the region of that surface feature 3610. This knurling provides a superior gripping surface for the Dentist. Each surface feature 3610 preferably has a length along longitudinal direction 3601 from about 3 mm to about 15 mm, more preferably from 3 mm to 10 mm, and more preferably still about 4 mm to 6 mm, or about 5 mm.

Each divider 3612 completely encircles handle 3600, and is preferably formed as a depression or recess in the outer surface of handle 3600, having a bottom surface that lies below the top surface of the knurling of the adjacent surface features 3610. This recess provides a convenient tactile reference for the Dentist when gripping handle 3600, and also serves to increase the gripping characteristics of handle 3600. To enhance the visual distinction between surface features 3610 and dividers 3612, the bottom surfaces of dividers 3612 may be smooth or polished, which visually contrasts with the relatively matte knurling of surface features 3610. Each divider 3612 preferably has a width along longitudinal direction 3601 of 0.3 mm to 2 mm, more preferably from 0.5 mm to 1 mm, more preferably still about 0.7 or 0.8 mm. Each divider 3612 preferably has a depth (which may be measured from the top or exterior surface of the adjacent surface feature 3610 knurling) of about 0.3 to 2 mm, more preferably about 0.3 to 1 mm, more preferably still about 0.5 to 0.7 mm.

The surface features 3610 and dividers 3612 provided by handle 3600 not only improve the grip of a Dentist upon handle 3600, but also provide both tactile and visual cues of distance from the working end of a tool that embodies handle 3600, which improves ease-of-use of such a tool.

Those skilled in the art will recognize that the present invention has many applications, may be implemented in various manners and, as such is not to be limited by the foregoing embodiments and examples. Any number of the features of the different embodiments described herein may be combined into a single embodiment, the locations of particular elements can be altered and alternate embodiments having fewer than or more than all of the features herein described are possible. For example, the neck region of a tool may include one or more of an S-shaped bend, a lateral bend to provide a lateral displacement of the working end, and a rotational displacement of the working end. The lateral displacement may be to the left or right of the longitudinal axis of the handle, and the rotational offset may be either clockwise or counter-clockwise. Functionality may also be, in whole or in part, distributed among multiple components, in manners now known or to become known.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention. While there has been shown and described fundamental features of the invention as applied to being exemplary embodiments thereof, it will be understood that omissions and substitutions and changes in the form and details of the disclosed invention may be made by those skilled in the art without departing from the spirit of the invention. Moreover, the scope of the present invention covers conventionally known, future developed variations and modifications to the components described herein as would be understood by those skilled in the art.

What is claimed is:

1. A dental tool, comprising:
   a handle region having a distal end and a proximal end, a longitudinal axis of the handle region extending within a lateral plane;
   a neck region connected to said distal end of the handle region and located downward from said lateral plane, said neck region comprising a first downward bend with respect to the longitudinal axis of the handle, a second upward bend with respect to the first downward bend, a distal end and a proximal end, said distal end of the neck region located further downward from said lateral plane than said proximal end of the neck region, said neck region extending in a downward and distal direction continuously from its proximal end to its distal end with respect to the axis of the handle;
   an operational unit connected to said distal end of the neck region and located entirely downward from said neck region, said operational unit comprising a downward surface configured to contact a patient, an opposing upward surface, a proximal end and a distal end, said distal end of the operational unit is located further downward from said lateral plane than said proximal end of the operational unit and is located further longitudinally from said distal end of the handle region than the longitudinal separation between said distal end of the neck region and the distal end of the handle region, wherein the dental tool is configured to be inserted into a patient's mouth such that the downward surface of the operational unit is configured to contact and depress or retract the patient's tongue or oral soft tissue.

2. The dental tool of claim 1, wherein the neck region further comprises:
   a first portion including said proximal end of the neck region and extending downward from said lateral plane;
   a second portion including said distal end of the neck region and extending away from said distal end of the handle region; and
   an area at which said first and second portions of the neck region meet, and
   at least a bend towards a lateral axis, the lateral axis being perpendicular to a transverse axis and the longitudinal axis of the handle, said transverse axis being perpendicular to the longitudinal axis.

3. The dental tool of claim 1, wherein the neck region comprises:
   a first portion including said proximal end of the neck region and extending downward from said lateral plane;
   a second portion including said distal end of the neck region and extending away from said distal end of the handle region;
   an area at which said first and second portions of the neck region meet, and
   at least one of the first portion, the second portion or the operational unit comprises a rotational offset with respect to another of the first portion, the second portion or the operational unit.

4. The dental tool of claim 1 wherein the operational unit comprises a tongue retractor.

5. The dental tool of claim 4 wherein the tongue retractor has an arcuate cross-section in a plane perpendicular to a transverse axis, said transverse axis being perpendicular to the longitudinal axis, said plane extending in the longitudinal and lateral directions.

6. The dental tool of claim 4 wherein the tongue retractor has a curved cross-section in a plane defined by a transverse axis and the longitudinal axis of the handle region, said transverse axis being perpendicular to the longitudinal axis, and wherein at least 50% of the angular curvature of the curved cross-section occurs in the most distal third of the tongue retractor.

7. The dental tool of claim 4 wherein the tongue retractor comprises a central bend that provides at least 50% of a transverse bend of the tongue retractor so that the tongue retractor has a substantially L-shaped cross-section in a plane defined by a transverse axis and the longitudinal axis of the handle region, said transverse axis being perpendicular to the longitudinal axis.

8. The dental tool of claim 4 wherein the tongue retractor includes a planar surface extending from the distal end of the neck region.

9. The dental tool of claim 4 wherein a most distal edge of the tongue retractor is non-parallel with respect to a plane that is perpendicular to a transverse axis, such that a first lateral edge of the tongue retractor is longer than an opposite second lateral edge of the tongue retractor, said transverse axis perpendicular to the longitudinal axis.

10. The dental tool of claim 1 wherein the handle region comprises a plurality of surface features sequentially disposed along a longitudinal length of the handle region, adjacent surface features being separated by a respective divider, each surface feature comprising knurling and each divider comprising a recess or a protrusion that extends below or above a top surface of the adjacent knurling.

11. The dental tool of claim 10 wherein the surface features have respective longitudinal lengths that are substantially equal to each other, and the dividers have respective longitudinal lengths that are substantially equal to each other.

12. A dental tool, comprising:
   a handle region having a distal end and a proximal end, longitudinal axis of the handle region extending within a lateral plane;
   a neck region connected to said distal end of the handle region and located downward from said lateral plane, said neck region comprising a first downward bend with respect to the longitudinal axis of the handle, a second upward bend with respect to the first downward bend, a distal end and a proximal end, said distal end of the neck region located further downward from said lateral plane than said proximal end of the neck region, said neck region extending in a downward and distal direction continuously from its proximal end to its distal end with respect to the axis of the handle; and
   a tongue retractor comprising a downward surface configured to contact a patient, an opposing upward surface, and a distal end located further longitudinally from said distal end of the handle region than the longitudinal separation between said distal end of the neck region and the distal end of the handle region:
   said neck region connected to said tongue retractor at a proximal end of said tongue retractor, said tongue retractor located entirely downward from said neck region;
   said first downward bend including said proximal end of the neck region and extending downward from said lateral plane, said second upward bend including said distal end of the neck region and extending away from said distal end of the handle region, and an area at which said first downward bend and said second upward bend of the neck region meet, said distal end of the neck region located at least as downward from said lateral plane as said area of the neck region so that the tongue retractor is downwardly offset with respect to the longitudinal axis of the handle region and directed from the longitudinal axis;
   wherein the tongue retractor comprises a central bend that provides at least 50% of a transverse bend of the tongue retractor so that the tongue retractor has a substantially L-shaped cross-section in a plane perpendicular to the lateral plane and aligned with the longitudinal axis of the handle region, wherein the dental tool is configured to be inserted into a patient's mouth such that the downward surface of the tongue retractor is configured to contact and depress or retract the patient's tongue or oral soft tissue.

13. The dental tool of claim 12 wherein a most distal edge of the tongue retractor is non-parallel with respect to a plane that is perpendicular to a transverse axis, such that a first lateral edge of the tongue retractor is longer than an opposite second lateral edge of the tongue retractor, said transverse axis being perpendicular to the longitudinal axis of the handle region.

14. The dental tool of claim 12 wherein the neck region further comprises at least a bend towards a lateral axis, the lateral axis being perpendicular to the transverse axis and the longitudinal axis of the handle region, so that the tongue retractor is laterally offset from the longitudinal axis of the handle region.

15. The dental tool of claim 12 wherein at least one of the first portion, the second portion or the tongue retractor comprises a rotational offset with respect to another of the first portion, the second portion or the tongue retractor.

16. A dental tool, comprising:
a handle region having a distal end and a proximal end, a longitudinal axis of the handle region extending within a lateral plane;
a neck region connected to said distal end of the handle region and located downward from said lateral plane, said neck region comprising a first downward bend with respect to the longitudinal axis of the handle, a second upward bend with respect to the first downward bend, a distal end and a proximal end, said distal end of the neck region located further downward from said lateral plane than said proximal end of the neck region, said neck region extending in a downward and distal direction continuously from its proximal end to its distal end with respect to the axis of the handle; and
a tongue retractor comprising a downward surface configured to contact a patient, an opposing upward surface, and a distal end located further longitudinally from said distal end of the handle region than the longitudinal separation between said distal end of the neck region and the distal end of the handle region;
said neck region connected to said tongue retractor at a proximal end of said tongue retractor, said tongue retractor located entirely downward from said neck region;
wherein the neck region first downward bend includes said proximal end of the neck region and extending downward from said lateral plane, said second upward bend includes said distal end of the neck region and extending away from said distal end of the handle region, and an area at which said first downward bend and second upward bend of the neck region meet, said distal end of the neck region located at least as downward from said lateral plane as said area of the neck region so that the tongue retractor is downwardly offset with respect to the longitudinal axis of the handle region and directed downward from the longitudinal axis of the handle region, wherein the dental tool is configured to be inserted into a patient's mouth such that the downward surface of the tongue retractor is configured to contact and depress or retract the patient's tongue or oral soft tissue; and
wherein the tongue retractor comprises a first planar surface extending from the distal end of the neck region.

17. The dental tool of claim 16 wherein the neck region further comprises at least a bend towards a lateral axis, the lateral axis being within the lateral plane and perpendicular to the longitudinal axis of the handle region, so that the tongue retractor is laterally offset from the longitudinal axis of the handle region.

18. The dental tool of claim 16 wherein at least one of the first portion, the second portion or the tongue retractor comprises a rotational offset of 5 to 45 degrees with respect to another of the first portion, the second portion or the tongue retractor.

19. A dental tool, comprising:
a handle region having a distal end and a proximal end, a longitudinal axis of the handle region extending within a lateral plane;
a neck region connected to said distal end of the handle region and located downward from said lateral plane, said neck region comprising a first downward bend with respect to the longitudinal axis of the handle, a second upward bend with respect to the first downward bend, a distal end and a proximal end, said distal end of the neck region located further downward from said lateral plane than said proximal end of the neck region, said neck region extending in a downward and distal direction continuously from its proximal end to its distal end with respect to the axis of the handle; and
a tongue retractor comprising a downward surface configured to contact a patient, an opposing upward surface, and a distal end located further longitudinally from said distal end of the handle region than the longitudinal separation between said distal end of the neck region and the distal end of the handle region; and
said neck region connected to said tongue retractor at a proximal end of said tongue retractor, said tongue retractor located entirely downward from said neck region;
wherein the neck region first downward bend includes said proximal end of the neck region and extending downward from said lateral plane, said second upward bend includes said distal end of the neck region and extending away from said distal end of the handle region, so that the tongue retractor is downwardly offset with respect to the longitudinal axis of the handle region and directed downward from the longitudinal axis of the handle region, wherein the dental tool is configured to be inserted into a patient's mouth such that the downward surface of the tongue retractor is configured to contact and depress or retract the patient's tongue or oral soft tissue; and
wherein the tongue retractor has a curved cross-section in a plane perpendicular to the lateral plane and aligned with the longitudinal axis of the handle region, at least 50% of the angular curvature of the tongue retractor in the plane occurring in the most distal third of the tongue retractor.

20. The dental tool of claim 19 wherein the neck region further comprises at least a bend towards a lateral axis, the lateral axis being within the lateral plane and perpendicular to the longitudinal axis of the handle region, so that the tongue retractor is laterally offset from the longitudinal axis of the handle region.

21. The dental tool of claim 19 wherein at least one of the first portion, the second portion or the tongue retractor comprises a rotational offset of 5 to 45 degrees with respect to another of the first portion, the second portion or the tongue retractor.

22. The dental tool of claim 1 wherein the neck region first downward bend includes said proximal end of the neck region and extends downward from said lateral plane, said second upward bend includes said distal end of the neck region and extends away from said distal end of the handle region, and an area at which said first downward bend and second upward bend of the neck region meet.

23. The dental tool of claim 22 wherein said distal end of the neck region is located at least as downward from said lateral plane as said area of the neck region.

* * * * *